US012714785B2

(12) United States Patent
Zade et al.

(10) Patent No.: US 12,714,785 B2
(45) Date of Patent: Aug. 25, 2026

(54) TECHNIQUES FOR IMPROVED AUTOMATIC DRUG DELIVERY PERFORMANCE USING DELIVERY TENDENCIES FROM PAST DELIVERY HISTORY AND USE PATTERNS

(71) Applicant: Insulet Corporation, Acton, MA (US)

(72) Inventors: Ashutosh Zade, San Diego, CA (US); Joon Bok Lee, Acton, MA (US); Yibin Zheng, Hartland, WI (US); Jason O'Connor, Acton, MA (US)

(73) Assignee: INSULET CORPORATION, Acton, MA (US)

( * ) Notice: Subject to any disclaimer, the term of this patent is extended or adjusted under 35 U.S.C. 154(b) by 1173 days.

(21) Appl. No.: 17/123,378

(22) Filed: Dec. 16, 2020

(65) Prior Publication Data

US 2021/0187197 A1 Jun. 24, 2021

Related U.S. Application Data

(60) Provisional application No. 63/049,653, filed on Jul. 9, 2020, provisional application No. 62/951,384, filed on Dec. 20, 2019.

(51) Int. Cl.

| | |
|---|---|
| ***G16H 20/17*** | (2018.01) |
| ***A61M 5/142*** | (2006.01) |
| ***A61M 5/172*** | (2006.01) |

(52) U.S. Cl.

CPC .......... *A61M 5/1723* (2013.01); *A61M 5/142* (2013.01); *G16H 20/17* (2018.01); (Continued)

(58) Field of Classification Search

CPC .................................................. A61M 5/1723

See application file for complete search history.

(56) References Cited

U.S. PATENT DOCUMENTS

| | | | |
|---|---|---|---|
| 303,013 | A | 8/1884 | Horton |
| 2,797,149 | A | 6/1957 | Skeggs |

(Continued)

FOREIGN PATENT DOCUMENTS

| | | | |
|---|---|---|---|
| AU | 2015200834 | A1 | 3/2015 |
| AU | 2015301146 | A1 | 3/2017 |

(Continued)

OTHER PUBLICATIONS

US 5,954,699 A, 09/1999, Jost et al. (withdrawn)

(Continued)

*Primary Examiner* — Bhisma Mehta
*Assistant Examiner* — Haden Matthew Ritchie
(74) *Attorney, Agent, or Firm* — Goodwin Procter LLP

(57) ABSTRACT

Disclosed are devices, a system, methods and computer-readable medium products that provide techniques to implement functionality to determine when to softened upper bounds of drug delivery and how much to soften the upper bound. Future blood glucose measurement values may be predicted by calculating deviations between predicted blood glucose measurement values and additional blood glucose measurement values. A gain parameter may be determined for use with a model of predicting a user's blood glucose measurement values and determining future drug dosages. Safety constraints may be determined based on an evaluation of missing blood glucose measurement values. In addition, safety constraints may be determined based on an evaluation of a user's increased interaction with an automatic drug delivery device. A bolus uncertainty metric to determine an amount of insulin to be provided in a bolus dosage in response to a bolus request may be calculated.

7 Claims, 14 Drawing Sheets

(52) U.S. Cl.
CPC ............. *A61M 2005/14208* (2013.01); *A61M 2005/1726* (2013.01); *A61M 2205/52* (2013.01)

(56) References Cited

U.S. PATENT DOCUMENTS 3,631,847 A 1/1972 Hobbs
3,634,039 A 1/1972 Brondy
3,812,843 A 5/1974 Wootten et al.
3,841,328 A 10/1974 Jensen
3,963,380 A 6/1976 Thomas, Jr. et al.
4,055,175 A 10/1977 Clemens et al.
4,146,029 A 3/1979 Ellinwood, Jr.
4,151,845 A 5/1979 Clemens
4,245,634 A 1/1981 Albisser et al.
4,368,980 A 1/1983 Aldred et al.
4,373,527 A 2/1983 Fischell
4,403,984 A 9/1983 Ash et al.
4,464,170 A 8/1984 Clemens et al.
4,469,481 A 9/1984 Kobayashi
4,475,901 A 10/1984 Kraegen et al.
4,526,568 A 7/1985 Clemens et al.
4,526,569 A 7/1985 Bernardi
4,529,401 A 7/1985 Leslie et al.
4,559,033 A 12/1985 Stephen et al.
4,559,037 A 12/1985 Franetzki et al.
4,573,968 A 3/1986 Parker
4,624,661 A 11/1986 Arimond
4,633,878 A 1/1987 Bombardieri
4,657,529 A 4/1987 Prince et al.
4,685,903 A 8/1987 Cable et al.
4,731,726 A 3/1988 Allen, III
4,743,243 A 5/1988 Vaillancourt
4,755,173 A 7/1988 Konopka et al.
4,781,688 A 11/1988 Thoma et al.
4,781,693 A 11/1988 Martinez et al.
4,808,161 A 2/1989 Kamen
4,854,170 A 8/1989 Brimhall et al.
4,886,499 A 12/1989 Cirelli et al.
4,900,292 A 2/1990 Berry et al.
4,919,596 A 4/1990 Slate et al.
4,925,444 A 5/1990 Orkin et al.
4,940,527 A 7/1990 Kazlauskas et al.
4,975,581 A 12/1990 Robinson et al.
4,976,720 A 12/1990 Machold et al.
4,981,140 A 1/1991 Wyatt
4,994,047 A 2/1991 Walker et al.
5,007,286 A 4/1991 Malcolm et al.
5,097,834 A 3/1992 Skrabal
5,102,406 A 4/1992 Arnold
5,109,850 A 5/1992 Blanco et al.
5,125,415 A 6/1992 Bell
5,134,079 A 7/1992 Cusack et al.
5,153,827 A 10/1992 Coutre et al.
5,165,406 A 11/1992 Wong
5,176,662 A 1/1993 Bartholomew et al.
5,178,609 A 1/1993 Ishikawa
5,207,642 A 5/1993 Orkin et al.
5,232,439 A 8/1993 Campbell et al.
5,237,993 A 8/1993 Skrabal
5,244,463 A 9/1993 Cordner, Jr. et al.
5,257,980 A 11/1993 Van Antwerp et al.
5,273,517 A 12/1993 Barone et al.
5,281,808 A 1/1994 Kunkel
5,299,571 A 4/1994 Mastrototaro
5,308,982 A 5/1994 Ivaldi et al.
5,342,298 A 8/1994 Michaels et al.
5,377,674 A 1/1995 Kuestner
5,380,665 A 1/1995 Cusack et al.
5,385,539 A 1/1995 Maynard
5,389,078 A 2/1995 Zalesky
5,411,889 A 5/1995 Hoots et al.
5,421,812 A 6/1995 Langley et al.
5,468,727 A 11/1995 Phillips et al.
5,505,709 A 4/1996 Funderburk et al.
5,505,828 A 4/1996 Wong et al.
5,507,288 A 4/1996 Bocker et al.
5,533,389 A 7/1996 Kamen et al.
5,558,640 A 9/1996 Pfeiler et al.
5,569,186 A 10/1996 Lord et al.
5,584,813 A 12/1996 Livingston et al.
5,609,572 A 3/1997 Lang
5,665,065 A 9/1997 Colman et al.
5,678,539 A 10/1997 Schubert et al.
5,685,844 A 11/1997 Marttila
5,685,859 A 11/1997 Kornerup
5,693,018 A 12/1997 Kriesel et al.
5,697,899 A 12/1997 Hillman et al.
5,700,695 A 12/1997 Yassinzadeh et al.
5,703,364 A 12/1997 Rosenthal
5,714,123 A 2/1998 Sohrab
5,716,343 A 2/1998 Kriesel et al.
5,722,397 A 3/1998 Eppstein
5,741,228 A 4/1998 Lambrecht et al.
5,746,217 A 5/1998 Erickson et al.
5,755,682 A 5/1998 Knudson et al.
5,758,643 A 6/1998 Wong et al.
5,800,405 A 9/1998 McPhee
5,800,420 A 9/1998 Gross et al.
5,801,057 A 9/1998 Smart et al.
5,804,048 A 9/1998 Wong et al.
5,817,007 A 10/1998 Fodgaard et al.
5,820,622 A 10/1998 Gross et al.
5,823,951 A 10/1998 Messerschmidt
5,840,020 A 11/1998 Heinonen et al.
5,848,991 A 12/1998 Gross et al.
5,851,197 A 12/1998 Marano et al.
5,858,005 A 1/1999 Kriesel
5,865,806 A 2/1999 Howell
5,871,470 A 2/1999 McWha
5,879,310 A 3/1999 Sopp et al.
5,902,253 A 5/1999 Pfeiffer et al.
5,931,814 A 8/1999 Alex et al.
5,932,175 A 8/1999 Knute et al.
5,935,099 A 8/1999 Peterson et al.
5,947,911 A 9/1999 Wong et al.
5,971,941 A 10/1999 Simons et al.
5,993,423 A 11/1999 Choi
5,997,501 A 12/1999 Gross et al.
6,017,318 A 1/2000 Gauthier et al.
6,024,539 A 2/2000 Blomquist
6,032,059 A 2/2000 Henning et al.
6,036,924 A 3/2000 Simons et al.
6,040,578 A 3/2000 Malin et al.
6,049,727 A 4/2000 Crothall
6,050,978 A 4/2000 Orr et al.
6,058,934 A 5/2000 Sullivan
6,066,103 A 5/2000 Duchon et al.
6,071,292 A 6/2000 Makower et al.
6,072,180 A 6/2000 Kramer et al.
6,077,055 A 6/2000 Vilks
6,090,092 A 7/2000 Fowles et al.
6,101,406 A 8/2000 Hacker et al.
6,102,872 A 8/2000 Doneen et al.
6,115,673 A 9/2000 Malin et al.
6,123,827 A 9/2000 Wong et al.
6,124,134 A 9/2000 Stark
6,126,637 A 10/2000 Kriesel et al.
6,128,519 A 10/2000 Say
6,142,939 A 11/2000 Eppstein et al.
6,143,164 A 11/2000 Heller et al.
6,157,041 A 12/2000 Thomas et al.
6,161,028 A 12/2000 Braig et al.
6,162,639 A 12/2000 Douglas
6,196,046 B1 3/2001 Braig et al.
6,200,287 B1 3/2001 Keller et al.
6,200,338 B1 3/2001 Solomon et al.
6,214,629 B1 4/2001 Freitag et al.
6,226,082 B1 5/2001 Roe
6,244,776 B1 6/2001 Wiley
6,261,065 B1 7/2001 Nayak et al.
6,262,798 B1 7/2001 Shepherd et al.
6,270,455 B1 8/2001 Brown
6,271,045 B1 8/2001 Douglas et al.

(56) References Cited

U.S. PATENT DOCUMENTS 6,280,381 B1 8/2001 Malin et al.
6,285,448 B1 9/2001 Kuenstner
6,309,370 B1 10/2001 Haim et al.
6,312,888 B1 11/2001 Wong et al.
6,334,851 B1 1/2002 Hayes et al.
6,375,627 B1 4/2002 Mauze et al.
6,379,301 B1 4/2002 Worthington et al.
6,402,689 B1 6/2002 Scarantino et al.
6,470,279 B1 10/2002 Samsoondar
6,475,196 B1 11/2002 Vachon
6,477,901 B1 11/2002 Tadigadapa et al.
6,484,044 B1 11/2002 Lilienfeld-Toal
6,491,656 B1 12/2002 Morris
6,512,937 B2 1/2003 Blank et al.
6,525,509 B1 2/2003 Petersson et al.
6,528,809 B1 3/2003 Thomas et al.
6,540,672 B1 4/2003 Simonsen et al.
6,544,212 B2 4/2003 Galley et al.
6,546,268 B1 4/2003 Ishikawa et al.
6,546,269 B1 4/2003 Kurnik
6,553,841 B1 4/2003 Blouch
6,554,798 B1 4/2003 Mann et al.
6,556,850 B1 4/2003 Braig et al.
6,558,351 B1 5/2003 Steil et al.
6,560,471 B1 5/2003 Heller et al.
6,561,978 B1 5/2003 Conn et al.
6,562,001 B2 5/2003 Lebel et al.
6,562,014 B2 5/2003 Lin et al.
6,569,125 B2 5/2003 Jepson et al.
6,572,542 B1 6/2003 Houben et al.
6,572,545 B2 6/2003 Knobbe et al.
6,574,490 B2 6/2003 Abbink et al.
6,575,905 B2 6/2003 Knobbe et al.
6,580,934 B1 6/2003 Braig et al.
6,618,603 B2 9/2003 Varalli et al.
6,633,772 B2 10/2003 Ford et al.
6,645,142 B2 11/2003 Braig et al.
6,653,091 B1 11/2003 Dunn et al.
6,662,030 B2 12/2003 Khalil et al.
6,669,663 B1 12/2003 Thompson
6,678,542 B2 1/2004 Braig et al.
6,699,221 B2 3/2004 Vaillancourt
6,718,189 B2 4/2004 Rohrscheib et al.
6,721,582 B2 4/2004 Trepagnier et al.
6,728,560 B2 4/2004 Kollias et al.
6,740,059 B2 5/2004 Flaherty
6,740,072 B2 5/2004 Starkweather et al.
6,751,490 B2 6/2004 Esenaliev et al.
6,758,835 B2 7/2004 Close et al.
6,780,156 B2 8/2004 Haueter et al.
6,810,290 B2 10/2004 Lebel et al.
6,837,858 B2 1/2005 Cunningham et al.
6,837,988 B2 1/2005 Leong et al.
6,846,288 B2 1/2005 Nagar et al.
6,862,534 B2 3/2005 Sterling et al.
6,865,408 B1 3/2005 Abbink et al.
6,890,291 B2 5/2005 Robinson et al.
6,936,029 B2 8/2005 Mann et al.
6,949,081 B1 9/2005 Chance
6,958,809 B2 10/2005 Sterling et al.
6,989,891 B2 1/2006 Braig et al.
6,990,366 B2 1/2006 Say et al.
7,008,404 B2 3/2006 Nakajima
7,009,180 B2 3/2006 Sterling et al.
7,016,713 B2 3/2006 Gardner et al.
7,018,360 B2 3/2006 Flaherty et al.
7,025,743 B2 4/2006 Mann et al.
7,025,744 B2 4/2006 Utterberg et al.
7,027,848 B2 4/2006 Robinson et al.
7,043,288 B2 5/2006 Davis, III et al.
7,060,059 B2 6/2006 Keith et al.
7,061,593 B2 6/2006 Braig et al.
7,096,124 B2 8/2006 Sterling et al.
7,115,205 B2 10/2006 Robinson et al.
7,128,727 B2 10/2006 Flaherty et al.
7,139,598 B2 11/2006 Hull et al.
7,144,384 B2 12/2006 Gorman et al.
7,171,252 B1 1/2007 Scarantino et al.
7,190,988 B2 3/2007 Say et al.
7,204,823 B2 4/2007 Estes et al.
7,248,912 B2 7/2007 Gough et al.
7,267,665 B2 9/2007 Steil et al.
7,271,912 B2 9/2007 Sterling et al.
7,278,983 B2 10/2007 Ireland et al.
7,291,107 B2 11/2007 Hellwig et al.
7,291,497 B2 11/2007 Holmes et al.
7,303,549 B2 12/2007 Flaherty et al.
7,303,622 B2 12/2007 Loch et al.
7,303,922 B2 12/2007 Jeng et al.
7,354,420 B2 4/2008 Steil et al.
7,388,202 B2 6/2008 Sterling et al.
7,402,153 B2 7/2008 Steil et al.
7,404,796 B2 7/2008 Ginsberg
7,429,255 B2 9/2008 Thompson
7,460,130 B2 12/2008 Salganicoff
7,481,787 B2 1/2009 Gable et al.
7,491,187 B2 2/2009 Van Den Berghe et al.
7,500,949 B2 3/2009 Gottlieb et al.
7,509,156 B2 3/2009 Flanders
7,547,281 B2 6/2009 Hayes et al.
7,569,030 B2 8/2009 Lebel et al.
7,608,042 B2 10/2009 Goldberger et al.
7,651,845 B2 1/2010 Doyle, III et al.
7,680,529 B2 3/2010 Kroll
7,734,323 B2 6/2010 Blomquist et al.
7,766,829 B2 8/2010 Sloan et al.
7,785,258 B2 8/2010 Braig et al.
7,806,854 B2 10/2010 Damiano et al.
7,806,886 B2 10/2010 Kanderian, Jr. et al.
7,918,825 B2 4/2011 OConnor et al.
7,946,985 B2 5/2011 Mastrototaro et al.
7,972,296 B2 7/2011 Braig et al.
8,221,345 B2 7/2012 Blomquist
8,251,907 B2 8/2012 Sterling et al.
8,449,524 B2 5/2013 Braig et al.
8,452,359 B2 5/2013 Rebec et al.
8,454,576 B2 6/2013 Mastrototaro et al.
8,467,980 B2 6/2013 Campbell et al.
8,478,557 B2 7/2013 Hayter et al.
8,547,239 B2 10/2013 Peatfield et al.
8,597,274 B2 12/2013 Sloan et al.
8,622,988 B2 1/2014 Hayter
8,810,394 B2 8/2014 Kalpin
9,061,097 B2 6/2015 Holt et al.
9,171,343 B1 10/2015 Fischell et al.
9,233,204 B2 1/2016 Booth et al.
9,486,571 B2 11/2016 Rosinko
9,579,456 B2 2/2017 Budiman et al.
9,597,451 B2 3/2017 Yodfat
9,743,224 B2 8/2017 San Vicente et al.
9,798,859 B2 10/2017 Yodfat
9,907,515 B2 3/2018 Doyle, III et al.
9,980,140 B1 5/2018 Spencer et al.
9,984,773 B2 5/2018 Gondhalekar et al.
10,248,839 B2 4/2019 Levy et al.
10,335,464 B1 7/2019 Michelich et al.
10,543,313 B2 1/2020 Damiano
10,583,250 B2 3/2020 Mazlish et al.
10,737,024 B2 8/2020 Schmid
10,987,468 B2 4/2021 Mazlish et al.
11,197,964 B2 12/2021 Sjolund et al.
11,260,169 B2 3/2022 Estes
2001/0021803 A1 9/2001 Blank et al.
2001/0034023 A1 10/2001 Stanton, Jr. et al.
2001/0034502 A1 10/2001 Moberg et al.
2001/0051377 A1 12/2001 Hammer et al.
2001/0053895 A1 12/2001 Vaillancourt
2002/0010401 A1 1/2002 Bushmakin et al.
2002/0010423 A1 1/2002 Gross et al.
2002/0016568 A1 2/2002 Lebel et al.
2002/0040208 A1 4/2002 Flaherty et al.
2002/0123740 A1 9/2002 Flaherty et al.
2002/0128543 A1 9/2002 Leonhardt
2002/0147423 A1 10/2002 Burbank et al.

(56) References Cited

U.S. PATENT DOCUMENTS

2002/0155425 A1 10/2002 Han et al.
2002/0161288 A1 10/2002 Shin et al.
2003/0023148 A1 1/2003 Lorenz et al.
2003/0050621 A1 3/2003 Lebel et al.
2003/0060692 A1 3/2003 Ruchti et al.
2003/0086074 A1 5/2003 Braig et al.
2003/0086075 A1 5/2003 Braig et al.
2003/0090649 A1 5/2003 Sterling et al.
2003/0100040 A1 5/2003 Bonnecaze et al.
2003/0130616 A1 7/2003 Steil et al.
2003/0135388 A1 7/2003 Martucci et al.
2003/0144582 A1 7/2003 Cohen et al.
2003/0163097 A1 8/2003 Fleury et al.
2003/0195404 A1 10/2003 Knobbe et al.
2003/0208113 A1 11/2003 Mault et al.
2003/0208154 A1 11/2003 Close et al.
2003/0212379 A1 11/2003 Bylund et al.
2003/0216627 A1 11/2003 Lorenz et al.
2003/0220605 A1 11/2003 Bowman, Jr. et al.
2004/0010207 A1 1/2004 Flaherty et al.
2004/0034295 A1 2/2004 Salganicoff
2004/0045879 A1 3/2004 Shults et al.
2004/0051368 A1 3/2004 Caputo et al.
2004/0064259 A1 4/2004 Haaland et al.
2004/0097796 A1 5/2004 Berman et al.
2004/0116847 A1 6/2004 Wall
2004/0122353 A1 6/2004 Shahmirian et al.
2004/0133166 A1 7/2004 Moberg et al.
2004/0147034 A1 7/2004 Gore et al.
2004/0171983 A1 9/2004 Sparks et al.
2004/0203357 A1 10/2004 Nassimi
2004/0204868 A1 10/2004 Maynard et al.
2004/0215492 A1 10/2004 Choi
2004/0220517 A1 11/2004 Starkweather et al.
2004/0241736 A1 12/2004 Hendee et al.
2004/0249308 A1 12/2004 Forssell
2005/0003470 A1 1/2005 Nelson et al.
2005/0020980 A1 1/2005 Inoue et al.
2005/0022274 A1 1/2005 Campbell et al.
2005/0033148 A1 2/2005 Haueter et al.
2005/0049179 A1 3/2005 Davidson et al.
2005/0065464 A1 3/2005 Talbot et al.
2005/0065465 A1 3/2005 Lebel et al.
2005/0075624 A1 4/2005 Miesel
2005/0105095 A1 5/2005 Pesach et al.
2005/0137573 A1 6/2005 McLaughlin
2005/0171503 A1 8/2005 Van Den Berghe et al.
2005/0182306 A1 8/2005 Sloan
2005/0192494 A1 9/2005 Ginsberg
2005/0192557 A1 9/2005 Brauker et al.
2005/0197621 A1 9/2005 Poulsen et al.
2005/0203360 A1 9/2005 Brauker et al.
2005/0203461 A1 9/2005 Flaherty et al.
2005/0238507 A1 10/2005 Dilanni et al.
2005/0261660 A1 11/2005 Choi
2005/0272640 A1 12/2005 Doyle, III et al.
2005/0277912 A1 12/2005 John
2006/0009727 A1 1/2006 OMahony et al.
2006/0079809 A1 4/2006 Goldberger et al.
2006/0100494 A1 5/2006 Kroll
2006/0134323 A1 6/2006 OBrien
2006/0167350 A1 7/2006 Monfre et al.
2006/0173406 A1 8/2006 Hayes et al.
2006/0189925 A1 8/2006 Gable et al.
2006/0189926 A1 8/2006 Hall et al.
2006/0197015 A1 9/2006 Sterling et al.
2006/0200070 A1 9/2006 Callicoat et al.
2006/0204535 A1 9/2006 Johnson
2006/0229531 A1 10/2006 Goldberger et al.
2006/0253085 A1 11/2006 Geismar et al.
2006/0264895 A1 11/2006 Flanders
2006/0270983 A1 11/2006 Lord et al.
2006/0276771 A1 12/2006 Galley et al.
2006/0282290 A1 12/2006 Flaherty et al.
2007/0016127 A1 1/2007 Staib et al.
2007/0060796 A1 3/2007 Kim
2007/0060869 A1 3/2007 Tolle et al.
2007/0060872 A1 3/2007 Hall et al.
2007/0083160 A1 4/2007 Hall et al.
2007/0106135 A1 5/2007 Sloan et al.
2007/0116601 A1 5/2007 Patton
2007/0118405 A1 5/2007 Campbell et al.
2007/0129690 A1 6/2007 Rosenblatt et al.
2007/0142720 A1 6/2007 Ridder et al.
2007/0173761 A1 7/2007 Kanderian et al.
2007/0173974 A1 7/2007 Lin et al.
2007/0179352 A1 8/2007 Randlov et al.
2007/0191716 A1 8/2007 Goldberger et al.
2007/0197163 A1 8/2007 Robertson
2007/0225675 A1 9/2007 Robinson et al.
2007/0244381 A1 10/2007 Robinson et al.
2007/0249007 A1 10/2007 Rosero
2007/0264707 A1 11/2007 Liederman et al.
2007/0282269 A1 12/2007 Carter et al.
2007/0287985 A1 12/2007 Estes et al.
2007/0293843 A1 12/2007 Ireland et al.
2008/0033272 A1 2/2008 Gough et al.
2008/0051764 A1 2/2008 Dent et al.
2008/0058625 A1 3/2008 McGarraugh et al.
2008/0065050 A1 3/2008 Sparks et al.
2008/0071157 A1 3/2008 McGarraugh et al.
2008/0071158 A1 3/2008 McGarraugh et al.
2008/0078400 A1 4/2008 Martens et al.
2008/0097289 A1 4/2008 Steil et al.
2008/0132880 A1 6/2008 Buchman
2008/0161664 A1 7/2008 Mastrototaro et al.
2008/0172026 A1 7/2008 Blomquist
2008/0177165 A1 7/2008 Blomquist et al.
2008/0188796 A1 8/2008 Steil et al.
2008/0200838 A1 8/2008 Goldberger et al.
2008/0206067 A1 8/2008 De Corral et al.
2008/0208113 A1 8/2008 Damiano et al.
2008/0214919 A1 9/2008 Harmon et al.
2008/0228056 A1 9/2008 Blomquist et al.
2008/0249386 A1 10/2008 Besterman et al.
2008/0269585 A1 10/2008 Ginsberg
2008/0269714 A1 10/2008 Mastrototaro et al.
2008/0269723 A1 10/2008 Mastrototaro et al.
2008/0287906 A1 11/2008 Burkholz et al.
2009/0006061 A1 1/2009 Thukral et al.
2009/0018406 A1 1/2009 Yodfat et al.
2009/0030398 A1 1/2009 Yodfat et al.
2009/0036753 A1 2/2009 King
2009/0043240 A1 2/2009 Robinson et al.
2009/0054753 A1 2/2009 Robinson et al.
2009/0069743 A1 3/2009 Krishnamoorthy et al.
2009/0069745 A1 3/2009 Estes et al.
2009/0069787 A1 3/2009 Estes et al.
2009/0099521 A1 4/2009 Gravesen et al.
2009/0105573 A1 4/2009 Malecha
2009/0131861 A1 5/2009 Braig et al.
2009/0156922 A1 6/2009 Goldberger et al.
2009/0156924 A1 6/2009 Shariati et al.
2009/0163781 A1 6/2009 Say et al.
2009/0198350 A1 8/2009 Thiele
2009/0221890 A1 9/2009 Saffer et al.
2009/0228214 A1 9/2009 Say et al.
2009/0318791 A1 12/2009 Kaastrup
2009/0326343 A1 12/2009 Gable et al.
2010/0057042 A1 3/2010 Hayter
2010/0114026 A1 5/2010 Karratt et al.
2010/0121170 A1 5/2010 Rule
2010/0137784 A1 6/2010 Cefai et al.
2010/0152658 A1 6/2010 Hanson et al.
2010/0174228 A1 7/2010 Buckingham et al.
2010/0211003 A1 8/2010 Sundar et al.
2010/0228110 A1 9/2010 Tsoukalis
2010/0262117 A1* 10/2010 Magni .................... G16H 20/17 604/504
2010/0262434 A1 10/2010 Shaya
2010/0295686 A1 11/2010 Sloan et al.
2010/0298765 A1 11/2010 Budiman et al.
2011/0021584 A1 1/2011 Berggren et al.
2011/0028817 A1 2/2011 Jin et al.

(56) References Cited

U.S. PATENT DOCUMENTS

2011/0054390 A1 3/2011 Searle et al.
2011/0054399 A1 3/2011 Chong et al.
2011/0124996 A1 5/2011 Reinke et al.
2011/0144586 A1 6/2011 Michaud et al.
2011/0160652 A1 6/2011 Yodfat et al.
2011/0178472 A1 7/2011 Cabiri
2011/0190694 A1 8/2011 Lanier, Jr. et al.
2011/0202005 A1 8/2011 Yodfat et al.
2011/0218495 A1 9/2011 Remde
2011/0230833 A1 9/2011 Landman et al.
2011/0251509 A1 10/2011 Beyhan et al.
2011/0313680 A1 12/2011 Doyle et al.
2011/0316562 A1 12/2011 Cefai et al.
2012/0003935 A1 1/2012 Lydon et al.
2012/0010594 A1 1/2012 Holt et al.
2012/0030393 A1 2/2012 Ganesh et al.
2012/0053556 A1 3/2012 Lee
2012/0078067 A1 3/2012 Kovatchev et al.
2012/0078161 A1 3/2012 Masterson et al.
2012/0078181 A1 3/2012 Smith et al.
2012/0101451 A1 4/2012 Boit et al.
2012/0123234 A1 5/2012 Atlas et al.
2012/0136336 A1 5/2012 Mastrototaro et al.
2012/0190955 A1 7/2012 Rao et al.
2012/0203085 A1 8/2012 Rebec
2012/0203178 A1 8/2012 Tverskoy
2012/0215087 A1 8/2012 Cobelli et al.
2012/0225134 A1 9/2012 Komorowski
2012/0226259 A1 9/2012 Yodfat et al.
2012/0232520 A1 9/2012 Sloan et al.
2012/0238851 A1 9/2012 Kamen et al.
2012/0271655 A1 10/2012 Knobel et al.
2012/0277668 A1 11/2012 Chawla
2012/0282111 A1 11/2012 Nip et al.
2012/0295550 A1 11/2012 Wilson et al.
2013/0030358 A1 1/2013 Yodfat et al.
2013/0158503 A1 6/2013 Kanderian, Jr. et al.
2013/0178791 A1 7/2013 Javitt
2013/0231642 A1 9/2013 Doyle et al.
2013/0253472 A1 9/2013 Cabiri
2013/0261406 A1 10/2013 Rebec et al.
2013/0296823 A1 11/2013 Melker et al.
2013/0317753 A1 11/2013 Kamen et al.
2013/0338576 A1 12/2013 OConnor et al.
2014/0005633 A1 1/2014 Finan
2014/0066886 A1 3/2014 Roy et al.
2014/0074033 A1 3/2014 Sonderegger et al.
2014/0121635 A1 5/2014 Hayter
2014/0128839 A1 5/2014 Dilanni et al.
2014/0135880 A1 5/2014 Baumgartner et al.
2014/0146202 A1 5/2014 Boss et al.
2014/0180203 A1 6/2014 Budiman et al.
2014/0180240 A1 6/2014 Finan et al.
2014/0200426 A1 7/2014 Taub et al.
2014/0200559 A1 7/2014 Doyle et al.
2014/0230021 A1 8/2014 Birthwhistle et al.
2014/0276554 A1 9/2014 Finan et al.
2014/0276556 A1 9/2014 Saint et al.
2014/0278123 A1 9/2014 Prodhom et al.
2014/0309615 A1 10/2014 Mazlish
2014/0316379 A1 10/2014 Sonderegger et al.
2014/0325065 A1 10/2014 Birtwhistle et al.
2015/0018633 A1 1/2015 Kovachev et al.
2015/0025329 A1 1/2015 Amarasingham et al.
2015/0025495 A1 1/2015 Peyser
2015/0073337 A1* 3/2015 Saint .................... G16H 40/67 604/66
2015/0120317 A1 4/2015 Mayou et al.
2015/0134265 A1 5/2015 Kohlbrecher et al.
2015/0165119 A1 6/2015 Palerm et al.
2015/0173674 A1 6/2015 Hayes et al.
2015/0213217 A1 7/2015 Amarasingham et al.
2015/0217052 A1 8/2015 Keenan et al.
2015/0217053 A1 8/2015 Booth et al.
2015/0265767 A1 9/2015 Vazquez et al.
2015/0306314 A1 10/2015 Doyle et al.
2015/0351671 A1 12/2015 Vanslyke et al.
2015/0366945 A1 12/2015 Greene
2016/0015891 A1 1/2016 Papiorek
2016/0038673 A1 2/2016 Morales
2016/0038689 A1 2/2016 Lee et al.
2016/0051749 A1 2/2016 Istoc
2016/0082187 A1 3/2016 Schaible et al.
2016/0089494 A1 3/2016 Guerrini
2016/0175520 A1 6/2016 Palerm et al.
2016/0228641 A1 8/2016 Gescheit et al.
2016/0243318 A1 8/2016 Despa et al.
2016/0256087 A1 9/2016 Doyle et al.
2016/0287512 A1 10/2016 Cooper et al.
2016/0302054 A1 10/2016 Kimura et al.
2016/0331310 A1 11/2016 Kovatchev
2016/0354543 A1 12/2016 Cinar et al.
2017/0049386 A1 2/2017 Abraham et al.
2017/0143899 A1 5/2017 Gondhalekar et al.
2017/0143900 A1 5/2017 Rioux et al.
2017/0156682 A1 6/2017 Doyle et al.
2017/0172473 A1* 6/2017 Wedekind .............. A61B 5/002
2017/0173261 A1 6/2017 OConnor et al.
2017/0189625 A1 7/2017 Cirillo et al.
2017/0281877 A1 10/2017 Marlin et al.
2017/0296746 A1 10/2017 Chen et al.
2017/0311903 A1 11/2017 Davis et al.
2017/0348482 A1 12/2017 Duke et al.
2018/0036495 A1 2/2018 Searle et al.
2018/0040255 A1 2/2018 Freeman et al.
2018/0075200 A1 3/2018 Davis et al.
2018/0075201 A1 3/2018 Davis et al.
2018/0075202 A1 3/2018 Davis et al.
2018/0092576 A1 4/2018 O'Connor et al.
2018/0126073 A1 5/2018 Wu et al.
2018/0169334 A1 6/2018 Grosman et al.
2018/0200434 A1 7/2018 Mazlish et al.
2018/0200438 A1 7/2018 Mazlish et al.
2018/0200441 A1 7/2018 Desborough et al.
2018/0204636 A1 7/2018 Edwards et al.
2018/0277253 A1 9/2018 Gondhalekar et al.
2018/0289891 A1 10/2018 Finan et al.
2018/0296757 A1 10/2018 Finan et al.
2018/0342317 A1 11/2018 Skirble et al.
2018/0369479 A1 12/2018 Hayter et al.
2019/0076600 A1 3/2019 Grosman et al.
2019/0240403 A1 8/2019 Palerm et al.
2019/0290844 A1 9/2019 Monirabbasi et al.
2019/0336683 A1 11/2019 O'Connor et al.
2019/0336684 A1 11/2019 O'Connor et al.
2019/0348157 A1 11/2019 Booth et al.
2020/0046268 A1 2/2020 Patek et al.
2020/0101222 A1 4/2020 Lintereur et al.
2020/0101223 A1 4/2020 Lintereur et al.
2020/0101225 A1 4/2020 O'Connor et al.
2020/0197605 A1* 6/2020 Haidar .................. G16H 50/50
2020/0219625 A1 7/2020 Kahlbaugh
2020/0342974 A1 10/2020 Chen et al.
2021/0050085 A1 2/2021 Hayter et al.
2021/0098105 A1 4/2021 Lee et al.
2022/0023536 A1 1/2022 Graham et al.

FOREIGN PATENT DOCUMENTS

CN 1297140 A 5/2001
DE 19756872 A1 7/1999
EP 0341049 A2 11/1989
EP 0496305 A2 7/1992
EP 0549341 A1 6/1993
EP 1491144 A1 12/2004
EP 0801578 B1 7/2006
EP 2666520 A1 10/2009
EP 2139382 A1 1/2010
EP 2397181 A1 12/2011
EP 2695573 A2 2/2014
EP 2830499 A1 2/2015
EP 2943149 A1 11/2015
EP 3177344 A1 6/2017
EP 3314548 A1 5/2018

(56) References Cited

FOREIGN PATENT DOCUMENTS

| | | | |
|---|---|---|---|
| EP | 1571582 | B1 | 4/2019 |
| EP | 2897071 | B1 | 5/2019 |
| EP | 3607985 | A1 | 2/2020 |
| GB | 2443261 | A | 4/2008 |
| JP | 51125993 | A | 11/1976 |
| JP | 851125993 | A | 11/1976 |
| JP | 02131777 | A | 5/1990 |
| JP | 2004283378 | A | 10/2007 |
| JP | 2017525451 | A | 9/2017 |
| JP | 2018153569 | A | 10/2018 |
| JP | 2019525276 | A | 9/2019 |
| TW | 200740148 | A | 10/2007 |
| TW | M452390 | U | 5/2013 |
| WO | 9800193 | A1 | 1/1998 |
| WO | 9956803 | A1 | 11/1999 |
| WO | 0030705 | A1 | 6/2000 |
| WO | 0032258 | A1 | 6/2000 |
| WO | 0172354 | A2 | 10/2001 |
| WO | 2002015954 | A1 | 2/2002 |
| WO | 0243866 | A2 | 6/2002 |
| WO | 02082990 | A1 | 10/2002 |
| WO | 03016882 | A1 | 2/2003 |
| WO | 03039362 | A1 | 5/2003 |
| WO | 03045233 | A1 | 6/2003 |
| WO | 05110601 | A1 | 5/2004 |
| WO | 2004043250 | A1 | 5/2004 |
| WO | 04092715 | A1 | 10/2004 |
| WO | 2005051170 | A2 | 6/2005 |
| WO | 2005082436 | A1 | 9/2005 |
| WO | 2005113036 | A1 | 12/2005 |
| WO | 2006053007 | A2 | 5/2006 |
| WO | 2007064835 | A2 | 6/2007 |
| WO | 2007078937 | A1 | 7/2007 |
| WO | 2008024810 | A2 | 2/2008 |
| WO | 2008029403 | A1 | 3/2008 |
| WO | 2008133702 | A1 | 11/2008 |
| WO | 2009045462 | A1 | 4/2009 |
| WO | 2009049252 | A1 | 4/2009 |
| WO | 2009066287 | A3 | 5/2009 |
| WO | 2009066288 | A1 | 5/2009 |
| WO | 2009098648 | A2 | 8/2009 |
| WO | 2009134380 | A2 | 11/2009 |
| WO | 2010053702 | A1 | 5/2010 |
| WO | 2010132077 | A1 | 11/2010 |
| WO | 2010138848 | A1 | 12/2010 |
| WO | 2010147659 | A2 | 12/2010 |
| WO | 2011095483 | A1 | 8/2011 |
| WO | 2012045667 | A2 | 4/2012 |
| WO | 2012108959 | A1 | 8/2012 |
| WO | 2012134588 | A1 | 10/2012 |
| WO | 2012177353 | A1 | 12/2012 |
| WO | 2012178134 | A2 | 12/2012 |
| WO | 2013078200 | A1 | 5/2013 |
| WO | 2013134486 | A2 | 9/2013 |
| WO | 20130149186 | A1 | 10/2013 |
| WO | 2013177565 | A1 | 11/2013 |
| WO | 2013182321 | A1 | 12/2013 |
| WO | 2014109898 | A1 | 7/2014 |
| WO | 2014110538 | A1 | 7/2014 |
| WO | 2014194183 | A2 | 12/2014 |
| WO | 2015056259 | A1 | 4/2015 |
| WO | 2015061493 | A1 | 4/2015 |
| WO | 2015073211 | A1 | 5/2015 |
| WO | 2015081337 | A2 | 6/2015 |
| WO | 2015187366 | A1 | 12/2015 |
| WO | 2016004088 | A1 | 1/2016 |
| WO | 2016022650 | A1 | 2/2016 |
| WO | 2016041873 | A1 | 3/2016 |
| WO | 2016089702 | A1 | 6/2016 |
| WO | 2016141082 | A1 | 9/2016 |
| WO | 2016161254 | A1 | 10/2016 |
| WO | 2017004278 | A1 | 1/2017 |
| WO | 2017091624 | A1 | 6/2017 |
| WO | 2017105600 | A1 | 6/2017 |
| WO | 2017184988 | A1 | 10/2017 |
| WO | 2017205816 | A1 | 11/2017 |
| WO | 2018009614 | A1 | 1/2018 |
| WO | 2018067748 | A1 | 4/2018 |
| WO | 2018120104 | A1 | 7/2018 |
| WO | 2018136799 | A1 | 7/2018 |
| WO | 2018204568 | A1 | 11/2018 |
| WO | 2019077482 | A1 | 4/2019 |
| WO | 2019094440 | A1 | 5/2019 |
| WO | 2019213493 | A1 | 11/2019 |
| WO | 2019246381 | A1 | 12/2019 |
| WO | 2020081393 | A1 | 4/2020 |
| WO | 2021011738 | A1 | 1/2021 |

OTHER PUBLICATIONS

"Understanding Insulin On Board (IOB)", Alberta Diabetes Link (Year: 2016).*

International Search Report and Written Opinion for the International Patent Application No. PCT/US2022/013470, mailed May 6, 2022, 14 pages.

International Search Report and Written Opinion for the International Patent Application No. PCT/US2022/013473, mailed May 6, 2022, 13 pages.

International Search Report and Written Opinion for the International Patent Application No. PCT/US2022/019079, mailed Jun. 2, 2022, 14 pages.

International Search Report and Written Opinion for the International Patent Application No. PCT/US2022/018453, mailed Jun. 2, 2022, 13 pages.

International Search Report and Written Opinion for the International Patent Application No. PCT/US22/018700, mailed Jun. 7, 2022, 13 pages.

International Search Report and Written Opinion for the International Patent Application No. PCT/US22/019080, mailed Jun. 7, 2022, 14 pages.

International Search Report and Written Opinion for the International Patent Application No. PCT/US22/019664, mailed Jun. 7, 2022, 14 pages.

International Search Report and Written Opinion for the International Patent Application No. PCT/US21/060618, mailed Mar. 21, 2022, 15 pages.

Herrero Pau et al: "Enhancing automatic closed-loop glucose control in type 1 diabetes with an adaptive meal bolus calculator -in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.

Marie Aude Qemerais: "Preliminary Evaluation of a New Semi-Closed-Loop Insulin Therapy System over the prandial beriod in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.

Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].

Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/ master/lib/determine-basal/determine-basal.js [retrieved on Jun. 6, 2022] line 116-line 118, line 439-line 446.

Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].

Kozak Milos et al: "Issue #2473 of AndroidAPS", MilosKozak / AndroidAPS Public repository, Mar. 4, 2020 (Mar. 4, 2020), pp. 1-4,

(56) References Cited

OTHER PUBLICATIONS

XP055900328, Retrieved from the Internet: URL:https://github.com/MilosKozak/AndroidAPS/issues/2473 [retrieved on Jun. 6, 2022].
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.
Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.
Fox, Ian G.; Machine Learning for Physiological Time Series: Representing and Controlling Blood Glucose for Diabetes Management; University of Michigan. ProQuest Dissertations Publishing, 2020. 28240142. (Year: 2020).
International Search Report and Written Opinion for the International Patent Application No. PCT/US2022/012896, mailed Apr. 22, 2022, 15 pages.
Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".
Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).
Dassau et al., "Real-Time Hypoglycemia Prediction Suite Using Contineous Glucose Monitoring," Diabetes Care, vol. 33, No. 6, 1249-1254 (2010).
International Search Report and Written Opinion for International Patent Application No. PCT/US17/53262, mailed on Dec. 13, 2017, 8 pages.
Van Heusden et al., "Control-Relevant Models for Glucose Control using A Priori Patient Characteristics", IEEE Transactions on Biomedical Engineering, vol. 59, No. 7, (Jul. 1, 2012) pp. 1839-1849.
Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).
Bequette, B.W., and Desemone, J., "Intelligent Dosing Systems": Need for Design and Analysis Based on Control Theory, Diabetes Technology and Therapeutics 9(6): 868-873 (2004).
Parker et al., "A Model-Based Agorithm for Blood Gucose Control in Type 1 Diabetic Patients." IEEE Transactions on Biomedical Engineering, 46 (2) 148-147 (1999).
International Search Report and Written Opinion for International Patent Application No. PCT/US2017/015601, mailed May 16, 2017, 12 pages.
International Search Report and Written Opinion for the International Patent Application No. PCT/US2018/018901, mailed on Aug. 6, 2018, 12 pages.
International Search Report and Written Opinion for International Patent Application No. PCT/US2018/052467, mailed Jan. 4, 2019, 13 pages.
"How to Create a QR Code that Deep Links to Your Mobile App", Pure Oxygen Labs, web<https://pureoxygenlabs.com/how-to-create-a-qr-codes-that-deep-link-to-your-mobile-app/>. Year:2017.
"Read NFC Tags with an iPHone App on iOS 11", GoToTags, Sep. 11, 2017, web <https://gototags.com/blog/read-nfc-tags-with-an-iphone-app-on-ios-11/> (Year:2017).
International Search Report and Written Opinion for International Patent Application No. PCT/US2016/063350, mailed on Mar. 27, 2017, 9 pages.
Extended Search Report mailed Aug. 13, 2018, issued in European Patent Application No. 16753053.4, 9 pages.
International Search Report and Written Opinion for International Patent Application No. PCT/US16/18452, mailed on Apr. 29, 2015, 9 pages.
International Preliminary Report on Patentability mailed Aug. 31, 2017, issued in PCT Patent Application No. PCT/US2016/018452, 7 pages.
International Search Report and Written Opinion for International Patent Application No. PCT/US2019/055862, mailed on Mar. 11, 2020.
International Search Report and Written Opinion for Application No. PCT/US2019/030652, Sep. 25, 2019, 19 bages.
Unger, Jeff, et al., "Glucose Control in the Hospitalized Patient," Emerg. Med 36(9):12-18 (2004).
"Glucommander FAQ" downloaded from https://adaendo.com/GlucommanderFAQ.html on Mar. 16, 2009.
Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.
Letters to the Editor regarding "Glucose Control in Critically Ill Patients," N Engl J Med 361: 1, Jul. 2, 2009.
"Medtronic is Leading a Highly Attractive Growth Market," Jun. 2, 2009.
Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.
Davidson, Paul C., et al. "Pumpmaster and Glucommander," presented at the MiniMed Symposium, Atlanta GA, Dec. 13, 2003.
Kanji S., et al. "Reliability of point-of-care testing for glucose measurement in critically ill adults," Critical Care Med, vol. 33, No. 12, pp. 2778-2785, 2005.
Krinsley James S., "Severe hypoglycemia in critically ill patients: Risk factors and outcomes," Critical Care Med, vol. 35, No. 10, pp. 1-6, 2007.
International Search Report and Written Opinion for the International Patent Application No. PCT/US2021/016283, mailed Jun. 2, 2021, 15 pages.
Farkas et al. ""Single-Versus Triple-Lumen Central Catheter-Related Sepsis: A Prospective Randomized Study in a Critically Ill Population"" The American Journal of Medicine Sep. 1992vol. 93 p. 277-282.
Davidson, Paul C., et al., A computer-directed intravenous insulin system shown to be safe, simple,and effective in 120,618 h of operation, Diabetes Care, vol. 28, No. 10, Oct. 2005, pp. 2418-2423.
R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.
Gorke, A ""Microbial Contamination Of Haemodialysis Catheter Connections"" Journal of Renal Care, European Dialysis & Transplant Nurses Association.
Lovich et al. "Central venous catheter infusions: A laboratory model shows large differences in drug delivery dynamics related to catheter dead volume" Critical Care Med 2007 vol. 35, No. 12.
Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.
Schlegel et al, "Multilumen Central Venous Catheters Increase Risk for Catheter-Related Bloodstream Infection: Prospective Surveillance Study".
Wilson, George S., et al., Progress toward the Development of an Implantable Sensor for Glucose, Clin. Chem., vol. 38, No. 9, 1992, pp. 1613-1617.
Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.
International Search Report and Written Opinion, International Application No. PCT/US2010/033794 mailed Jul. 16, 2010 (OPTIS.247VPC).
International Search Report and Written Opinion in PCT/US2008/079641 (Optis.203VPC) dated Feb. 25, 2009.

(56) References Cited

OTHER PUBLICATIONS

Berger, ""Measurement of Analytes in Human Serum and Whole Blood Samples by Near-Infrared Raman Spectroscopy,"" Ph.D. Thesis, Massachusetts Institute of Technology, Chapter 4, pp. 50-73, 1998.
Berger, "An Enhanced Algorithm for Linear Multivariate Calibration," Analytical Chemistry, vol. 70, No. 3, pp. 623-627, Feb. 1, 1998.
Billman et al., "Clinical Performance of an In line Ex-Vivo Point of Care Monitor: A Multicenter Study," Clinical Chemistry 48: 11, pp. 2030-2043, 2002.
Widness et al., "Clinical Performance on an In-Line Point-of-Care Monitor in Neonates"; Pediatrics, vol. 106, No. 3, pp. 497-504, Sep. 2000.
Finkielman et al., "Agreement Between Bedside Blood and Plasma Glucose Measurement in the ICU Setting"; retrieved from http://www.chestjournal.org; CHEST/127/5/May 2005.
Glucon Critical Care Blood Glucose Monitor; Glucon; retrieved from http://www.glucon.com.
Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.
Vonach et al., "Application of Mid-Infrared Transmission Spectrometry to the Direct Determination of Glucose in Whole Blood," Applied Spectroscopy, vol. 52, No. 6, 1998, pp. 820-822.
Muniyappa et al., "Current Approaches for assessing insulin sensitivity and resistance in vivo: advantages, imitations, and appropriate usage," AJP-Endocrinol Metab, vol. 294, E15-E26, first published Oct. 23, 2007.
International Preliminary Report on Patentability for the International Patent Application No. PCT/US2019/053603, mailed Apr. 8, 2021, 9 pages.
International Search Report and Written Opinion for the International Patent Application No. PCT/US2019/053603, mailed Jan. 7, 2020, 16 pages.
Dassau et al., "Detection of a meal using continuous glucose monitoring: Implications for an artificial [beta]-cell." Diabetes Care, American Diabetes Association, Alexandria, VA, US, 31(2):295-300 (2008).
Cameron et al., "Probabilistic Evolving Meal Detection and Estimation of Meal Total Glucose Appearance Author Affiliations", J Diabetes Sci and Tech,Vol., Diabetes Technology Society ;(5):1022-1030 (2009).
Lee et al., "A closed-loop artificial pancreas based on model predictive control: Human-friendly identification and automatic meal disturbance rejection", Biomedical Signal Processing and Control, Elsevier, Amsterdam, NL, 4(4):1746-8094 (2009).
Anonymous: "Fuzzy control system", Wikipedia, Jan. 10, 2020. URL: https://en.wikipedia.org/w/index.php?title=Fuzzy_control_system&oldid=935091190.
An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.
International Search Report and Written Opinion for the InternationalPatent Application No. PCT/US2021/017441, mailed May 25, 2021, 12 pages.
Mirko Messori et al: "Individualized model predictive control for the artificial pancreas: In silico evaluation of closed-loop glucose control", IEEE Control Systems, vol. 38, No. 1, Feb. 1, 2018, pp. 86-104.
International Search Report and Written Opinion for the International Patent Application No. PCT/US2021/017662, mailed May 26, 2021, 14 pages.
Anonymous: "Reservoir Best Practice and Top Tips" Feb. 7, 2016, URL: https://www.medtronic-diabetes.co.uk/blog/reservoir-best-practice-and-top-tips, p. 1.
Gildon Bradford: "InPen Smart Insulin Pen System: Product Review and User Experience" Diabetes Spectrum, vol. 31, No. 4, Nov. 15, 2018, pp. 354-358.
International Search Report and Written Opinion for the International Patent Application No. PCT/US2021/016050, mailed May 27, 2021, 16 pages.
International Search Report and Written Opinion for the International Patent Application No. PCT/US2020/065226, mailed May 31, 2021, 18 pages.
International Search Report and Written Opinion for the International Patent Application No. PCT/US2021/017659, mailed May 31, 2021, 13 pages.
Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.
Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.
Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.
Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.
E. Atlas et al., "MD-Logic Artificial Pancreas System: A pilot study in adults with type 1 diabetes", Diabetes Care, vol. 33, No. 5, Feb. 11, 2010, pp. 1071-1076.
European Search Report for the European Patent Application No. 21168591.2, mailed Oct. 13, 2021, 151 pages.
International Search Report and Written Opinion for the International Patent Application No. PCT/US2021/041954, mailed Oct. 25, 2021, 13 pages.
International Search Report and Written Opinion for the International Patent Application No. PCT/US2021/047771, mailed Dec. 22, 2021, 11 pages.
International Search Report and Written Opinion for the International Patent Application No. PCT/US2021/052855, mailed Dec. 22, 2021, 11 pages.
International Search Report and Written Opinion for International Patent Application No. PCT/US2021/051027, mailed on Jan. 7, 2022, 16 pages.
International Search Report and Written Opinion for International Patent Application No. PCT/US2021/052372, mailed Jan. 26, 2022, 15 pages.
International Search Report and Written Opinion for the International Patent Application No. PCT/US2021/046607, mailed Jan. 31, 2022, 20 pages.
International Search Report and Written Opinion for the International Patent Application No. PCT/US2021/055745, mailed Feb. 14, 2022, 13 pages.
International Search Report and Written Opinion for the International Patent Application No. PCT/US2020/052125, mailed Aug. 12, 2020, 15 pages.
International Search Report and Written Opinion for the International Patent Application No. PCT/US2020/050332, mailed Sep. 12, 2020, 12 pages.
European Patent Office, "Notification of Transmittal of the ISR and the Written Opinion of the International Searching Authority, or the Declaration," in PCT Application No. PCT/GB2015/050248, Jun. 23, 2015, 12 pages.
International Search Report and Written Opinion for the International Patent Application No. PCT/US2021/022694, mailed Jun. 25, 2021, 13 pages.
International Searching Authority, Invitation to Pay Additional Fees, International Application No. PCT/US2006/004929, mailed Jul. 27, 2006.
International Search Report and Written Opinion for Application No. PCT/US2019/030652, Sep. 25, 2019, 19 pages.

* cited by examiner

TECHNIQUES FOR IMPROVED AUTOMATIC DRUG DELIVERY PERFORMANCE USING DELIVERY TENDENCIES FROM PAST DELIVERY HISTORY AND USE PATTERNS

CROSS-REFERENCE TO RELATED APPLICATIONS

This application claims the benefit of the filing date of U.S. Provisional Application Ser. No. 62/951,384, filed Dec. 20, 2019, and U.S. Provisional Application Ser. No. 63/049,653, filed Jul. 9, 2020, the entire contents of which are incorporated herein by reference in their entirety.

BACKGROUND

Due to the complicated and dynamic nature of the human body's response to insulin, it is unfortunately common for patients to end up in a hypoglycemic or hyperglycemic state after being treated with insulin therapy. This outcome is undesirable for many reasons: hypoglycemia creates an immediate risk of a severe medical event (seizure, coma, death) while hyperglycemia creates long term negative health effects as well as the risk of ketoacidosis. Whether a person ends up in one of these states depends on a combination of data inputs and responses.

Some closed-loop insulin delivery systems operate on specific, hard safety constraints on insulin delivery that define fixed limits on insulin delivery. These hard safety constraints that may be universally applied to all users may unduly limit optimization of insulin delivery specific to each user.

Automatic insulin delivery systems when assessing the user's insulin needs incorporate models of blood glucose and insulin interactions to calculate its recommendations. The models may be too rigid and may also unduly limit the predictive capabilities of the automatic insulin delivery systems when evaluating the blood glucose and insulin interactions of a specific user.

The ability of closed-loop insulin delivery systems to adjust delivery based on user physiology is limited based on input parameters that do not accurately reflect specific user physiology in real time or substantially real time.

In addition to the models and input parameters being limited, some automated insulin delivery systems are limited to reliance on a single data stream (continuous glucose monitor (CGM) estimated glucose value (EGV) readings) to calculate the recommended insulin deliveries. There are other efforts to utilize additional sensors (such as heart rate, skin temperature, skin impedance, accelerometry) to gain more data streams, but these implementations require additional body real estate for the sensors and increased cost of the sensors.

In other areas, bolus estimation remains a challenge for diabetics despite various advances in bolus estimation methods in recent times. The challenge arises due to most bolus estimation methods focus on general estimates of carbohydrates and a food library that provide general guidelines. As a result, the carbohydrate estimates and the food library lack specifics on carbohydrate quality, protein to carbohydrate ratio, fibers and further sub-classification of fibers into soluble and insoluble fibers as well as other omissions.

It would be beneficial if techniques and systems were developed to address the above problems as well as others.

BRIEF DESCRIPTION OF THE DRAWINGS

FIG. 6B is a flow chart of a meal evaluation process that is operable to extract meal-related information from inputs received by an image-based bolus estimation application or plug-in.

DETAILED DESCRIPTION

Figure 1:
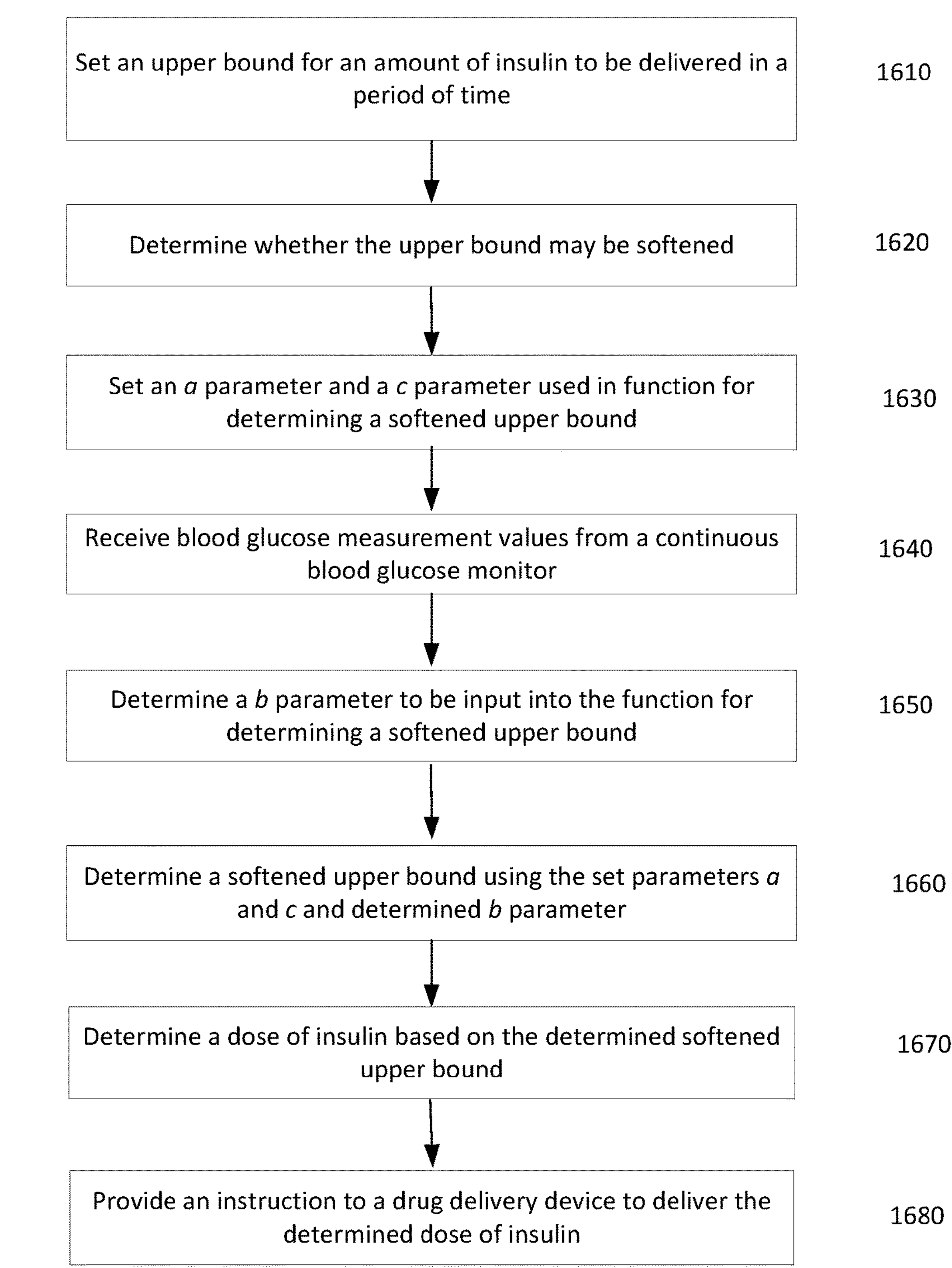
FIG. 1 shows a flow chart of an example of a process for determining a softened upper bound for delivery of insulin.

An example of a dynamic, personalized (control-outcome dependent) real-time softening of hard safety constraints in closed loop artificial pancreas systems generally relates to any closed loop insulin delivery system that operates on specific, hard safety constraints on insulin delivery to improve the closed loop insulin delivery system's robustness against hypoglycemia (i.e., low blood sugar). Closed loop artificial pancreas systems rely on blood glucose measurement values obtained by a continuous blood glucose monitor or the like that are evaluated by a personal diabetes management device to regulate a person's blood glucose. These specific, hard safety constraints are generally defined as fixed limits on insulin delivery at each actuation (e.g., delivery of insulin) and may be dependent on thresholds of blood glucose values or past insulin delivery histories. However, the interaction of blood glucose values and insulin deliveries in actual human bodies are never in stasis or equilibrium, and thus fixed safety constraints that are commonly implemented in these systems may be improved by implementing "soft" asymptotic limits instead, which may be dynamically personalized based on user-inputted clinical parameters, glucose variability, or real-time control outcomes. For instance, instead of incorporating a fixed limit on total insulin delivery for any given cycle (e.g., a measurement of blood glucose and a delivery of a dosage of insulin based on the blood glucose measurement), a parameterized threshold may be incorporated above which the penalization on insulin delivery may be proportionally increased. Both the value of this parametrized threshold as well as the "softness" or "permeability" of this threshold may be customized by a variety of factors individual to each person with type 1 diabetes mellitus (T1DM). This implementation reduces any closed loop insulin delivery system's dependence on ad hoc safety constraints and allows the safety of the system to adapt dynamically to the needs of each user.

In an example, the following describes advanced, on-line updates of glucose prediction models for optimum closed loop artificial pancreas algorithm performance with compatible architectural change generally relating to establishing a model of glucose and insulin interactions in a person with Type 1 Diabetes. The model may be used by an AP application to project what is going to happen with an automatic insulin delivery (AID) system with respect to the model. In an example, the model may be fixed. But in other examples, the model may be adjustable. While there may be efforts that are utilizing artificial intelligence and machine learning processes to provide a real-time adjustable model, these real-time artificial intelligence and machine learning processes require an amount of computational power that exceeds the capabilities of the wearable or portable sensors or device, such as diabetes management devices, continuous glucose monitoring devices, or drug delivery devices. Closed loop insulin delivery algorithms that automatically assess the user's insulin needs may incorporate these models of glucose and insulin interactions to calculate recommendations for timing and doses of insulin delivery. The following discloses examples of 1) Online updates of model parameters based on residuals between model predictions and actual glucose values, where residuals may be a difference between predictions and actual values; 2) Higher order models (incorporation of insulin deliveries from prior history) of glucose deliveries; 3) Inclusion of advanced insulin effects beyond simple insulin delivery; and 4) Inclusion of glucose rate of changes beyond auto-regressive model of glucose values only.

In an example of a hardware implementation of a real-time model adjustment, the example processes may be implemented on a blood glucose sensor. The blood glucose sensor may, for example, be a continuous blood glucose monitor (CGM) that may be operable to receive insulin delivery information from a personal diabetes management device and CGM, Rate of Change (RoC) values (e.g., rate of change of the blood glucose measurements over time) sent as part of the advertising packet in Bluetooth® Low-Energy (BLE) available for use by any insulin delivery pump.

The described process and hardware implementations provide improvements in the predictive capabilities of any model of glucose and insulin interactions in people with Type 1 Diabetes (T1D) or Type 1 Diabetes Mellitus (T1DM) and may improve the closed loop control outcomes in any algorithm, not just the AP application examples discussed herein that utilizes these models.

An example describes methods for continuous, personalized adjustment of automated insulin delivery in artificial pancreas systems for T1DM applications relating to adjustment of automated insulin delivery systems for people with type 1 diabetes, and specifically to Artificial Pancreas (AP) systems that execute automatic closed loop insulin delivery by linking a continuous glucose monitor (CGM) with an insulin pump. The algorithm to calculate the amount of insulin delivered based on the input continuous glucose monitor value must be robustly designed and capable of modifying its behavior depending on the user's physiology. This disclosure outlines novel methods for more accurate reflection of the user's changing insulin needs in real time within the closed loop algorithms by, for example, adjusting the input TDI clinical parameter based on mean glucose deviations from the target, and adjusting the gain of any algorithm's model based on actual clinical glucose trajectories.

An example describes methods of identification of improved automated insulin delivery performance through user insulin delivery tendencies from past delivery history and user insulin pump use patterns relates to solving a problem with automated insulin delivery systems that are limited to reliance on a single data stream, such as estimated glucose value (EGV) readings from a continuous glucose monitor (CGM), to calculate recommended insulin deliveries. There are other efforts to utilize additional sensors (such as heart rate, skin temperature, skin impedance, accelerometry, and the like) to gain more data streams, but these implementations require additional body real estate for the sensors and the increased cost of the respective sensors.

In an example, an automatic insulin delivery (AID) system may have several underutilized data streams that may be exploited for additional information on user interaction patterns and insulin delivery tendencies. This additional information may be utilized for improved glucose control performance beyond utilizing the EGV readings provided by the CGM. In this example, there may be at least 3 variants of these additional data streams: 1) Utilization of missing EGVs, pressure-induced sensor attenuation (PISA) events, significant jumps in EGVs through calibrations and other CGM characteristic error events to determine possible sensor or pump site issues; 2) Utilization of user interaction of the personal diabetes manager (PDM) or similar interface with the AID system to determine user's level of concern with the current life events; and 3) Utilization of user bolus patterns to estimate accuracy of user requested boluses. The algorithm behavior in response to using any of the at least three variants may enable the AID system to provide recommendations for the user's diabetes treatment.

One or more examples provide a process that may be used with any additional algorithms or computer applications, such as an AP application as described herein or a third-party artificial pancreas application, which may manage blood glucose levels and provide insulin therapy. Such algorithms may be referred to as an "artificial pancreas" algorithm-based system, or more generally, an artificial pancreas (AP) application, which provides automatic delivery of insulin based on a blood glucose sensor input, such as that received from a CGM or the like. In an example, the artificial pancreas (AP) application when executed by a processor may enable a system to monitor a user's glucose values, determine an appropriate level of insulin for the user based on the monitored glucose values (e.g., blood glucose concentrations or blood glucose measurement values) and other information, such as user-provided information, such as carbohydrate intake, exercise times, meal times or the like, and take actions to maintain a user's blood glucose value within an appropriate range. The appropriate blood glucose value range may be considered a target blood glucose value of the particular user. For example, a target blood glucose value may be acceptable if it falls within the range of 80 mg/dL to 120 mg/dL, which is a range satisfying the clinical standard of care for treatment of diabetes. However, an AP application as described herein may be able to establish a target blood glucose value more precisely and may set the target blood glucose value at, for example, 110 mg/dL, or the like. As described in more detail with reference to the examples of FIGS. 1-4C, the AP application may utilize the monitored blood glucose values and other information to generate and send a command to a medical device including, for example, a pump, to control delivery of insulin to the user, change the amount or timing of future doses, as well as to control other functions based on the profile of duration of insulin action.

An example implementation of parameterized safety limits in a closed loop system that is implemented with a permeability layer to allow a dynamic, personalized adaptation of generic, fixed insulin delivery safety constraints is provided. An upper boundary is set so the AP application does not over deliver insulin according to the automatic insulin delivery system. In some examples, the upper boundary does not prevent a user from manually instructing the automatic insulin delivery system to deliver a dose of insulin.

In this example, insulin deliveries in typical closed loop systems are often subject to a wide range of safety constraints. The results of applying these safety constraints may be combined into a fixed upper bound $I_{ub}$ which serves as a hard limit on insulin delivery. The fixed upper bound $L_{ub}$ may be based on a number of variables, such as past blood glucose measurements, past insulin deliveries, blood glucose measurement rate of change, and other factors as shown below. A process for implementing the parameterized safety limits is shown in FIG. 1. In the process 1600, an upper bound may be set for an amount of insulin to be delivered in a period of time (1610). A period of time may, for example, be a day, week, a month, or the like. In the example, the AP application may set the upper bound based on user input or based on a function that takes a number of parameters as inputs.

In an example, the AP application may establish an upper bound $I_{ub}$ that may not be exceeded by insulin delivery recommendations I(t) made by the AP application as shown in the functions below:

$$I(t) \leq I_{ub}(t)$$

$$I_{ub}(t) = f(I(t), G(t), IOB(t), ROC(t))$$

where $I_{ub}$ is a fixed upper bound of insulin that may be delivered over the period of time, and the function ƒ has parameters, where: I(t) is an amount of insulin to be delivered at an approximate given time t, G(t) is current blood glucose measurements at the approximate given time t, IOB(t) is an amount of insulin onboard at the approximate given time t, and ROC(t) is a rate of change of a user's blood glucose at the approximate given time t. In an example, the AP application may obtain blood glucose measurements at regular intervals, which may substantially coincide with the approximate given time. In addition, at or about the regular interval, the AP application may determine and/or calculate recommended insulin delivery (i.e., an amount or dose of insulin to be delivered at approximately the regular interval), insulin onboard and rate of change.

At 1620, the AP application may determine whether the upper bound may be parameterized or "softened." For example, the AP application may parameterize, or soften, these constraints based on known control outcomes. For instance, a soft constraint may be derived from the hard constraint $I_{ub}$ by incorporating an asymptotic approach to a value that is a certain proportion higher than $I_{ub}$:

$$I_{ub,soft}(t) = \frac{a \cdot \log(1+b)}{1 + a \cdot \log(1+b)} \cdot c \cdot I_{ub}(t)$$

the above parameterized version of the hard constraints can dynamically increase or reduce an actual upper bound on insulin delivery applied by an AP application using the algorithm once the hard upper constraint is derived from any control algorithm's standard implementation.

The parameters a, b, and c represent the following characteristics in the soft constraint:

| | |
|---|---|
| a | Rate of convergence of $I_{ub,soft}$ to $I_{ub}$ depending on the user dependent parameter b |
| b | Location on the soft constraint curve and may be user dependent |
| c | The threshold for which the soft constraint will asymptotically approach; can allow soft constraints to converge above the hard constraint |

The parameters a and c may be tuned based on inputs to the AP application and insulin the delivery history of the AP application to improve the constraint's robustness against outliers or allow the constraint to be more responsive to parameters set by a user. For example, the parameter b may be utilized to apply various characteristics of the user's current, real-time control outcomes.

In an example, the parameter a may be set to 1 and the parameter c may be set to 2 (1630). In this example, the parameter b may be made dependent on a mean summed square of glucose deviations below target within the past 3 hours, as follows:

$$b = \frac{10\sum_{i=0}^{35} \max(50, SP - G(t))^2}{36 \cdot 2500}$$

where, in the above example function, the parameter 10 represents the standard convergence to 130% of the original $I_{ub}(t)$ hard upper bound, and horizon for consideration (36 data points from the current cycle (e.g., 3 hours times 12 blood glucose measurements=36 data points), SP represents the current blood glucose setpoint (i.e., target glucose setpoint) for the user, 2500 represents the summed square of deviations if the measured blood glucose is always at 70 mg/dL and the current blood glucose setpoint (i.e., target glucose setpoint) is at 120 mg/dL, the 50 represents an expected difference between the lower boundary for hypoglycemic risk set at 70 mg/dL and a current blood glucose setpoint (SP—in this example is 120 mg/dL).

In the example, the AP application may, at 1640, receive blood glucose measurement values at given times. The given times may be a period of intervals, such as 5 minute intervals, which coincide with the output of blood glucose measurements from a continuous glucose monitor (shown in another example). The blood glucose measurement values may be received by the AP application over a period of time (e.g., 3 hours-36 data points (12 blood glucose measurements per hour for 3 hours)). In addition, the AP application may be operable to store the received blood glucose measurement values in a memory of a personal diabetes management device or the like (shown in another example) until a number (e.g., 36) of blood glucose measurements are received. Alternatively, the AP application may input the received blood glucose measurement values into the maximum function in real time so the parameter b may be determined in real time.

For example, at 1650, the AP application may further determine an actual difference between the measured blood glucose value (G(t)) at the given time and the SP (e.g., 120 mg/dL). After the AP application determines the actual difference between the measured blood glucose value (G(t)) at the given time and the SP (e.g., 120 mg/dL), the AP application in the execution of the max function may determine a final difference. The final difference may be the difference between the expected difference (e.g., 50) of the blood glucose measurement (G(t)) and the current blood glucose setpoint (SP) and the actual difference (SP-G(t)). This final difference may be squared and summed over the 36 data points (from each G(t)) and multiplied by 10 to obtain the numerator. The numerator may be divided by the denominator to obtain the value of parameter b for the period of time.

Upon receipt of the blood glucose measurement values, the AP application may determine the b parameter. In an example calculation of the parameter b, if the blood glucose measurements of a user are consistently below the user's blood glucose set point for the 36 data points, the parameter b is greater than 10, if the blood glucose measurements of the user are consistently equal to the user's blood glucose set point for the 36 data points, the parameter b is equal to 10; and if the blood glucose measurements are consistently above the user's blood glucose set point for the 36 data points, the parameter b is less than 10. In an example, the parameter b may be considered a rate at which the AP application permits the upper bound to be exceeded as the amount of insulin delivered approaches the softened upper bound.

After determination of the parameter b at 1650, the AP application may determine a softened upper bound using the set of parameters a and c and the determined parameter b (1660). Softening the upper bound means, for example, raising a threshold value of the upper bound to allow an amount of insulin to be delivered that is greater than the initially-set upper bound (as in step 1610). In the described specific example, the AP application allows the upper bound to be exceeded by up to, for example, approximately 30% of the user's total daily insulin, if the user did not experience a significant amount of time below 70 mg/dL in the preceding 3 hours (e.g., the user's blood glucose measurements were not below 70 mg/dL for more than 45 minutes out of the 3 hours, or the like). However, since the AP application may recalculate the parameter b and the softened upper bound upon receipt of another blood glucose measurement value, the AP application may rapidly reduce the softened upper bound if the user's blood glucose measurements does fall below 70 mg/dL, which indicates a possibility of hypoglycemic risk. Percentages in addition to 30%, such as 25%, 50% or the like may be used.

Based on the determined softened upper bound, the AP application may determine a dose of insulin to be delivered to a user (1670). The determined dose of insulin may be an amount of insulin between the set upper bound and the softened upper bound. The determined dose of insulin may cause the amount of insulin delivered in a day to exceed the upper bound set at 1610, but that may lead to the amount of insulin delivered to asymptotically approach the softened upper bound. The AP application may output a signal to a drug delivery device (not shown in this example) containing an instruction to deliver the determined dose of insulin (1680). In this example, the softened upper bound is not exceeded but may be set higher in a subsequent iteration of the process 1600.

This implementation example enables the AP application to dynamically personalize in real-time the upper bound safety constraint based on the user's current diabetes management and blood glucose control outcomes while also allowing a slight violation (i.e., softening) of the hard constraints if the control outcome has been favorable for a period of time, such as 24 hours, 48 hours, or longer.

In other examples, these safety constraints may be made dependent on run-to-run approaches, such as executing the adaptation of the safety constraints once every certain period of data is collected, as alternate forms of adaptivity instead of real time approaches. Prior examples were real-time modifications or updates, while the AP application may also be operable to make modifications and updates to the safety constraints over time.

In addition, the AP application may use total daily insulin (TDI) in the determination to make the modifications or updates instead of set point (SP). For example, in the function that determines parameter b, the 2500 in the denominator may be replaced with TDI while the maximum tolerance may be 10 units of insulin off from the TDI. Other examples may be for example, proportion of user bolus-to-basal in TDI may also be used.

In this example process of FIG. 1, clinical parameters may be determined with a high confidence of accuracy by the pump, such as total daily insulin (TDI), may be used to modulate the softness (a, c) of the constraints as well as the dependence of the constraint on the parameter (b).

The example of an advanced, on-line updates of glucose prediction models for optimum closed loop artificial pancreas algorithm performance with compatible architectural change that may be operable to improve the formulation of any generic model of insulin and glucose interactions in an insulin delivery system paired with a glucose sensor. A model is typically used to either provide a predicted glucose trajectory for the user, or are incorporated into closed loop insulin delivery algorithms, such as an AP application discussed herein as well as AP applications provided by others, to optimize glucose control outcomes for a respective user. Individual users may begin with a generic model that may be adjusted over time based on the respective individual user's physiology and participation in a diabetes treatment plan that utilizes an automatic insulin delivery (AID) system.

In an example, a standard glucose prediction model of $n^{th}$ order may be implemented to project future glucose values $G_{pred,m}$ from past glucose and insulin delivery values as:

$$G_{pred,m}(k) = b_1 G(k-1) + b_2 G(k-2) + \ldots b_n G(k-n) + a_1 I(k-1) + a_2 I(k-2) + \ldots a_n I(k-n)$$

Where G(k−i)=past blood glucose measurements, G(k)=present glucose measurements, and I(k−i)=past insulin deliveries, and i is 1 to n.

Figure 2:
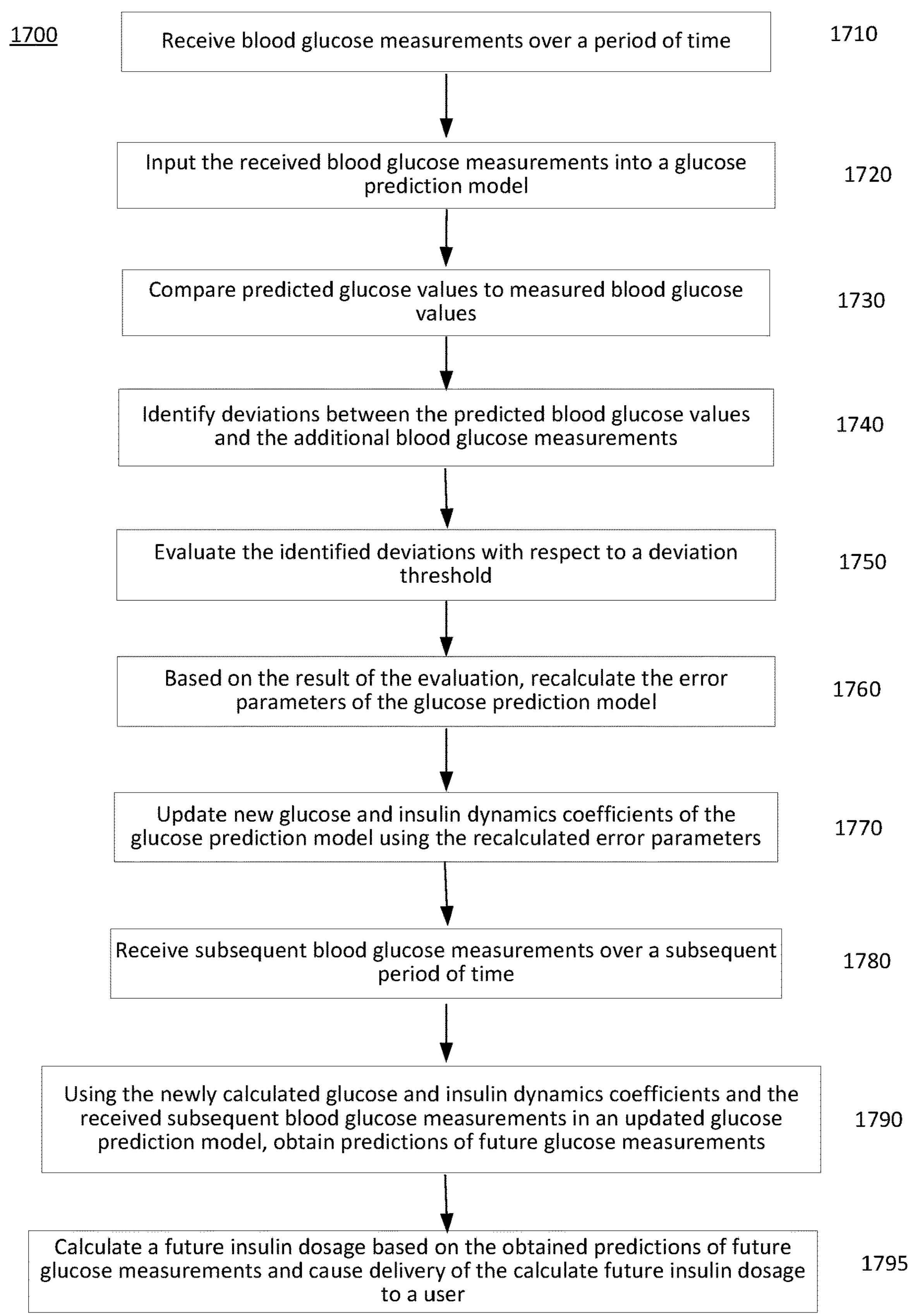
FIG. 2 shows a flow chart of an example of a process for adjustment of a critical parameters of any generic model of glucose and insulin dynamics.

In an example process, such as that shown in FIG. 2, the process 1700 may be implemented to augment or supplement an automatic insulin delivery system that is under control of an artificial pancreas (AP) application. Alternatively, a processor executing programming code may be operable to provide the process 1700 may be implemented on a continuous blood glucose monitor (CGM) or the like (shown in another example). A CGM may make blood glucose measurements approximately every 5 minutes. In an example, a processor executing an AP application on a personal diabetes management device or a processor executing programming code may be operable to implement the process 1700. In the example, the processor may be operable to receive blood glucose measurements over a period of time (1710). For example, the AP application may be executing on a personal diabetes management device may receive the blood glucose measurements via a wireless communication link between the device executing an AP application and a CGM. In the example, the period of time may be one hour, 4 hours, 24 hours, or the like.

At 1720, the received blood glucose measurements may be input into a glucose prediction model $G_{pred,m}(k)$, such as that shown above. The values generated by the glucose prediction model are predictions of future blood glucose values. For example, the predicted blood glucose values may be blood glucose values that are predicted to occur 5, 10, 15, 30, 45 minutes or the like in the future from when the received blood glucose measurements are input into the glucose prediction model. The predicted blood glucose values may be compared to additional blood glucose measurements provided by a CGM (1730). The additional blood glucose measurements may be obtained by a CGM at times that correspond to the times associated with the predicted blood glucose values.

The AP application, when utilizing the process 1700, may identify deviations between the predicted blood glucose values and the additional blood glucose measurements (1740). In an example, the AP application may evaluate the identified deviations with respect to a deviation threshold (1750). Based on the result of the evaluation, the AP application may either take no action or recalculate the error parameters of the glucose prediction model. For example, if the number of identified deviations that exceed the deviation threshold does not exceed a predetermined number, the AP application may take no action. Alternatively, if a predetermined number of identified deviations exceeds the deviation threshold, the process 1700 may recalculate error parameters of the glucose prediction model (1760).

The error parameters may be determined using various functions. For example, the error (E(k)) may be the estimated error between the past predictions of the process 1700 and current glucose values that may be assessed by the following estimated error parameter equation:

$$E(k) = \sum_{i=0}^{r} \sum_{m=0}^{p} \left( \frac{G(k-i) - G_{Pred,m}(k-i)}{G(k-i)} \right)^2$$

where r is the history horizon for which the error will be assessed, and p is the prediction horizon of the model that is being assessed. The first term G(k−i) may, for example, be a current glucose value and the second term ($G_{pred,m}(k-i)$) may be the predicted glucose value. In the estimated error parameter equation, the numerator dividing by the first term that forms the denominator to provide a proportional error for the current cycle. Summation over the prediction (i.e., the first summation of p) time period into the future enables the error to be extrapolated to a point in time in the future. However, p may not extend longer than several cycles into the future. Limiting the limit p in this manner allows the glucose prediction model to reveal any persistent error. In an example, over the last 5 predictions, the limit p may be fixed at 12, which may, for example, be 1 hour of CGM data. In some examples, the limit r may not exceed the value of the limit p. The second summation of r is how many cycles during which the model may make a predictive adjustment. A cycle may be a time period of 1 hour (e.g., 12 blood glucose measurements), 8 hours (e.g., 96 blood glucose measurements), 24 hours (e.g., 288 blood glucose measurements), or the like. For example, if the AP application is operable to adjust the glucose prediction model daily, the limit r may be set to 12 measurements/hour×24 hours=288 measurements, and the parameter k may be a 5 minute measurement interval or the like.

At 1770, the AP application or algorithm may update new glucose and insulin dynamics coefficients of the glucose prediction model using recalculated error parameters. For example, the glucose and insulin dynamics coefficients $b_1 \ldots b_n$ of the glucose prediction model may be updated based on the estimated error parameter E(k):

$$b_{m,new} = b_{m,old} \frac{E(k)}{rp} (\text{bias value})$$

where r is the history horizon for which the error may be assessed, p is the actual prediction horizon for which the model may predict into the future, and (bias value) is a tuning parameter that can be scaled against r and p to adjust how rapidly the model dynamics coefficients can be adjusted.

In this embodiment, the impact of previous glucose values on the model, i.e. the order of the model, may be discounted with increasing residuals, with a lower bound on the model as a zero-order hold from the most recent glucose value. This, for example, reduces the complexity and thus computational cost of the model, allowing for more efficient implementation in real life systems.

After the glucose and insulin dynamics coefficients $b_1 \ldots b_n$ of the glucose prediction model have been updated (1780), subsequent blood glucose measurements may be received over a subsequent period of time.

The AP application or another algorithm may use the newly calculated glucose and insulin dynamics coefficients $b_1 \ldots b_n$ and the received subsequent blood glucose measurements in an updated glucose prediction model, predictions of future glucose measurements may be obtained (1790).

The future glucose measurements may be used in a calculation of a future insulin dosage based on the obtained predictions of future glucose measurements, and, the AP application may cause delivery of the calculated future glucose measurements to a user (1795). The AP application may instruct a drug delivery device to deliver to a user based on a calculation of a future insulin dosage based on the obtained predictions of future glucose measurements.

Additionally, other metrics as the variability of glucose values and/or insulin deliveries above or below certain thresholds based on the user's clinical parameters can also be utilized to better inform the model. For example, frequency of calibration may indicate that the glucose readings were not as reliable as parameterized by the model. In the example, the indication of frequent calibration indicates a lack of confidence by the user because the user for some reason believes the model is not incorrect. As a result, the r parameter or history horizon may be reduced, or alternatively, adjust the bias value.

In other examples, higher order models may also be implemented. In another example, the glucose prediction model as described in the earlier example, may be updated to accommodate glucose and insulin interactions of $n^{th}$ order. The $n^{th}$-order glucose prediction model may be developed to have non-linear dependence depending on the stability characteristics:

$$G_{pred}(k) = b_1 G(k-1)^a + b_2 G(k-2)^b + \ldots\ b_n G(k-n)^c + a_1 I(k-1)^d + a_2 I(k-2)^e + \ldots\ a_n I(k-n)^z$$

Where G(k−i)=past blood glucose measurements, G(k)=present glucose measurements, I(k−i)=past insulin deliveries, and the exponentials a, b, c, . . . are arbitrary exponents that can also be identified through a similar online identification process as above and be modified in real time. The exponentials allow the incorporation of exponential considerations for indicating the likely greater impact that insulin delivered earlier is currently having on blood glucose measurements.

In further examples, additional insulin effects beyond direct insulin delivery entries may be accounted for by the AP application. In another example of a model of glucose and insulin interactions may be modified to include more advanced insulin effects such as insulin onboard (IOB). In this example, the glucose values may be more impacted by the user's insulin-on-board values (IOB) at each cycle. The resulting generalized equation may be expressed as:

$$G_{pred}(k) = b_1 G(k-1)^a + b_2 G(k-2)^b + \ldots\ b_n G(k-n)^c + a_1 IOB(k-1)^d + a_2 IOB(k-2)^e + \ldots\ a_n IOB(k-n)^z$$

Where G(k−i)=past blood glucose measurements, G(k)=present glucose measurements, I(k−i)=past insulin deliveries, IOB(k−i)=past IOB determinations, i is 1 to n, and the exponentials a, b, c, . . . are arbitrary exponents that can also be identified through a similar online identification process as above and be modified in real time.

Additional glucose effects beyond auto-regressive incorporation of raw glucose values may also be incorporated into the model. In another example, it is known that the raw blood glucose measurement values from available continuous blood glucose sensors are not as accurate as the rate of change (ROC) estimates of the continuous blood glucose sensors. While information may be gleaned from the raw blood glucose measurement values, a better indication of the effect of the delivered insulin is the rate of change of the raw blood glucose measurement values. Therefore, these models can incorporate the raw rate of change (RoC) values reported by glucose sensors directly to further augment the model:

$$G_{pred}(k) = b_1 ROC(k-1)^a + b_2 ROC(k-2)^b + \ldots\ b_n ROC(k-n)^c + a_1 IOB(k-1)^d + a_2 IOB(k-2)^e + \ldots\ a_n IOB(k-n)^z$$

Where IOB(k−i)=past insulin onboard determinations, ROC (k−i)=past rate of change of glucose, i is 1 to n, and the exponentials a, b, c, . . . are arbitrary exponents that can also be identified through a similar online identification process as above and be modified in real time.

In an example, the automatic insulin delivery algorithms implemented via an AP application or the like in an artificial pancreas system may reside on the insulin delivery vehicles and communicate with continuous glucose monitoring sensors using Bluetooth® Low-Energy protocols. Examples of BLE protocols may use multiple handshakes and points of error before the actual information is sent. By generating a glucose prediction using the above examples of a model, the AP application may be upgraded by implementing the improved model of glucose and insulin interactions as above directly on a continuous glucose monitor (CGM—shown in another example) to avoid the need for the multiple handshakes when providing measurement information. For example, the CGM may utilize the advertising calls available in the BLE protocol to enable insulin deliver by a drug delivery device. By generating the glucose prediction information at the CGM, the CGM may be compatible with multiple drug delivery devices rather than being exclusive to a single drug delivery device.

Further, the recent upgrades to BLE 5.0 means that the typical handshaking approach may be significantly simplified if the CGM may be made to directly advertise its CGM value and RoC values within the advertising packet, which will significantly reduce the points of failure in the communication pathway between a drug delivery device and the CGM thereby improving robustness of the overall diabetes management system. In one or more examples, a CGM may provide blood glucose measurement, estimated rate of change, confidence interval (e.g., how confident the CGM is that the blood glucose measurement is accurate expressed as a range, e.g., BG measurement may be 110, but confidence interval is 100-120) and noise levels.

There are additional inputs that may be implemented to improve the model of insulin/glucose interactions. For instance, clinical outcomes such as the percentage of times that the user spends in safe glycemic range (70-180) within their control may be made as an input to the algorithm. Based on this input, for example, the AP application may determine whether the model's gain (i.e., b coefficients) may be modulated. For example, in the last 24 hours, the user was within range, and as a result, the gain (i.e., b parameters) of the model may be adjusted to a higher value.

In another example, the model may also be extended to incorporate other additional inputs to the system that may be available. For example, inputs such as accelerometer positions (X, Y, Z accelerations), skin temperature, heart rate, pump back pressure (longer time period for insulin to be delivered), frequency of user calibrations of blood glucose measurements, how often a user checks status of system (indicating system is not working properly), and other entries. These may be added to the model to influence real time adjustment. In the example, an input from a skin temperature sensor may provide correlation with respect to determining whether a user is exercising. More specifically, a higher skin temperature at legs as compared to the skin temperature in the abdomen may indicate the user is running. Similarly, elevated inputs values or levels received from a heart rate monitor and an accelerometer (e.g., increased heart rate or increased instantaneous accelerometer values) may indicate exercise. In another example, pump back pressure may indicate that insulin delivery takes longer for the insulin to pass through the interstitial tissue and get into the bloodstream; therefore, the model may be adjusted to respond more slowly to account for the delay in insulin delivery. Meanwhile, an increased number of user status checks may indicate that the automatic insulin delivery (AID) system is not performing optimally and that the user lacks confidence in the AP application settings. As a result, the model parameters may be adjusted in response to the increased number of user status checks.

Figure 3:
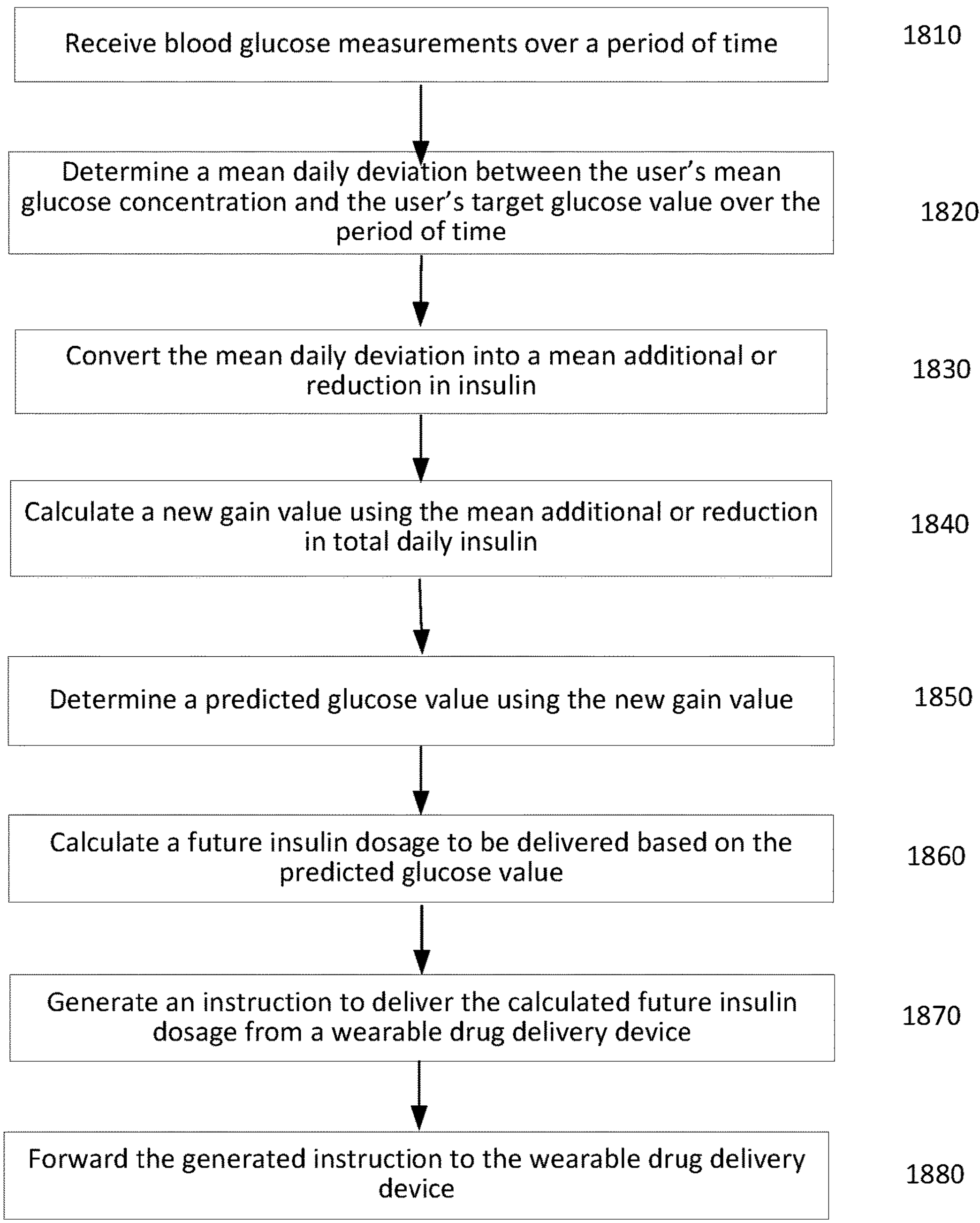
FIG. 3 shows a flow chart of another example of a process for adjustment of a critical parameters of any generic model of glucose and insulin dynamics.

The following example described with reference to FIG. 3 is an implementation of an automatic adjustment of critical parameters of any generic model of glucose and insulin dynamics that may be utilized in automatic insulin delivery systems for insulin pumps connected with glucose sensors. To accomplish an automatic adjustment of individual model parameters, a number of different parameters may be used, for example, TDI, basal delivery profile, correction factor (e.g., a parameter that represents how much the blood glucose of a user is dropping per 1 unit of insulin delivered to the user), insulin-to-carbohydrate, or other clinical parameters. In the particular example, blood glucose measurements made at different times and an amount of insulin delivered at, or near, the different times may be used as generalized or generic parameters in the determination of a predicted blood glucose value.

A process 1800 may be implemented by a processor or by an AP application. For example, an algorithm, which may be executed by an AP application, may receive blood glucose measurements over a period of time (1810). In the example, the blood glucose measurements may be received from a continuous glucose monitor or the like.

In the example, a model of glucose and insulin dynamics may be subject to a gain K, or a multiplier to the model, as follows:

$$K \cdot G_p(k) = b_1 G(k-1) + b_2 G(k-2) + \ldots b_n G(k-n) + a_1 I(k-1) + a_2 I(k-2) + \ldots a_n I(k-n)$$

Where K is a generalized gain of this generic model of glucose and insulin values, $G_p$ is a predicted blood glucose measurement, k is an iteration of the blood glucose measurement, $b_n$ are weightings based on estimated correlation between past glucose values and predicted glucose values, G is blood glucose measurement values, and I is an amount of insulin delivered.

In certain examples, the gain K of the model may be defined using various clinical parameters of the user that characterize the user's insulin needs. For example, an advanced TDI determination based on personalized adaptation and adjustment of model gain K may be used.

In the example, the generalized gain K may be dependent on the user's total daily insulin, or TDI parameter, as:

$$K = -c(1-p_1)(1-p_2) \ldots (1-p_n)\frac{A}{TDI}$$

Where c and A are constants unique to the generic glucose and insulin dynamics model and $p_{1-n}$ are poles of the generic glucose and insulin dynamics model. Values of c and A may be selected based on, for example, the conversion factors between units, insulin infusion rates, insulin infusions, insulin delivery methods, and others, and may have values of, for example, 0.05, 0.06, 0.07, and such for c, and 40, 50, 60, and such for A.

Thus, TDI may be a component of a model of glucose and insulin dynamics given that it represents the total insulin needs of the user.

In a further example, the total daily insulin (TDI) value that is incorporated into the generic glucose and insulin dynamics model may be adjusted in real time based on the user's daily mean blood glucose measurement values. For example, in the process 1800 at 1820, this adjustment may be conducted by calculating a mean daily deviation between the user's blood glucose measurement and the user's target blood glucose value (each at particular iteration i) as:

$$\overline{D} = \sum_{i=1}^{N} \frac{G(i) - \text{target }(i)}{288}$$

where N is the total number of available datapoints, i is the specific datapoint, G is the user's blood glucose measurement value and target is the user's target blood glucose value.

In the example, the mean daily deviation $\overline{D}$ provides the average deviation from the user's target glucose. The summation of the user's blood glucose measurement value and target is the user's target blood glucose value that provides a total average deviation over the amount of time (e.g., 288 based on N). For example, the mean daily deviation may be determined between a user's mean blood glucose values and the user's target glucose value over a period of time.

The mean daily deviation $\overline{D}$ may be converted into a mean addition to insulin or a mean reduction in insulin that may be needed to maintain glucose at the target glucose based on the user's correction factor parameter:

$$TDI_e = \frac{\overline{D}}{CF}$$

where $TDI_e$ is extra/reduced TDI (where extra refers to additional insulin and reduced refers to reduction in insulin), and CF is the correction factor parameter (1830).

In the process 1800, the mean extra or reduction in total daily insulin may be used to calculate a new gain value (1840). The calculated extra/reduced TDIe may be implemented into the generic glucose and insulin dynamics model by being used in a calculation of a new gain value Knew as:

$$K_{new} = -c(1-p_1)(1-p_2) \ldots (1-p_n)\frac{A}{TDI + TDI_e}$$

In a further example, the adjustment to the gain value may be made more conservative or aggressive based on a factor Q:

$$K_{new,2} = -c(1-p_1)(1-p_2) \ldots (1-p_n)\frac{A}{TDI + Q \cdot TDI_e}$$

where $K_{new,2}$ refers to the gain value calculated using the factor Q, where Q is a tuning factor that can determine how much the new TDI may be weighted as part of these adjustments.

For example, the Q factor may be adjusted by the percent number (%) of times a user is in the hypoglycemic range (e.g., the user's blood glucose measurement value is less than 70 mg/dL):

$$Q_{hypo} = Q\left(1 - \frac{N_{hypo}}{N}\right)$$

or by glucose variability (e.g., a value representative of how much a user's blood glucose measurements change over time):

$$Q_{var} = Q\left(1 - \frac{GV}{100}\right)$$

Where $Q_{var}$ may be used to increase the robustness of the glucose prediction $G_{pred}$.

The new gain value may be used to determine a predicted glucose value (1850).

The AP application or algorithm may be operable to calculate a future insulin dosage to be delivered based on the predicted glucose values determined using the new gain value (1860). In addition, at 1870, the AP application or algorithm may be operable to generate an instruction to deliver the calculated future insulin dosage from a wearable drug delivery device (not shown in this example). At 1880, the generated instruction may be forwarded by the AP application to the wearable drug delivery device.

In yet another example, an advanced model gain adaptivity of the model gain K may also be provided based on clinical traces which may be updated based on actual clinical outcomes. In the example, the gain K* may be a fixed value that is determined a priori.

For example, the glucose prediction portion of a general model of glucose-insulin dynamics above may be assessed versus known insulin delivery histories to minimize the least square outcomes:

$$K^* = \frac{\sum_{i=1}^{N} (b_1 G(i-1) + b_2 G(i-2) + \ldots\ b_n G(i-n))}{I(i)}$$

In another example, the insulin delivery and glucose histories of a user may be used to calculate an adapted model gain that enables the effects of prandial (meal) periods to be removed which minimizes the impact of carbohydrate ingestions on the predicted glucose measurements.

There are additional alternative examples that may be utilized to further adapt the response of the AP application or algorithm behavior. For instance, a linear incorporation of glucose variability and a percentage (%) of times a user's blood glucose measurements are in the hypoglycemic range (i.e., less than (<) 70 mg/dL) may instead be implemented, for example, by incorporating a weighted horizon approach that discounts periods of very high glucose variability more than periods of low variability.

Further, the incorporation of clinical traces based on model gain can incorporate an iterative optimization approach where areas without significant outside disturbances may be identified within the historical profiles. The values from the areas without significant outside disturbances may be utilized to derive a more accurate modified gain K*.

In an example of a system that utilizes additional sources of data, the additional data may be gleaned from the fact that the users of an automatic insulin delivery (AID) system, which may use an AP application, is a part of closed loop process, and may remain since a user may continuously interact with an AID system throughout their lives. For example, some continuous blood glucose monitors (CGM) may provide, in addition to blood glucose measurement values, blood glucose measurement rate of change values, a noise factor, and a confidence factor, or a combination thereof. The noise factor may be a setting of the sensor that indicates a level of confidence in the blood glucose measurements, and the confidence factor may be a range of confidence related to the provided blood glucose measurement. For example, the noise factor (which may, for example, be an integer value between 1-10 and where 1 may indicate high confidence and 10 may indicate low confidence) may cause the AP application to respond to a provided blood glucose measurement less aggressively. For example, if a blood glucose measurement was 150 mg/dL and the noise factor may indicate a confidence value of 9, the AP application or algorithm may modify the dose of insulin to be delivered based on the noise factor to be lower than expected, indicating a lower confidence in the glucose value due to the high level of noise. In contrast to the noise factor, the confidence factor is a tolerance level expressed as a range of the blood glucose measurement values. For example, the CGM may also provide a range of blood glucose measurement values, such as 115-130 mg/dL that indicate the confidence the CGM has in the current blood glucose measurement value.

In another example, the CGM may provide a measure (or indication) of pressure to an AP application. The provided pressure measurement may indicate that the system is experiencing pressure-induced sensor attenuation (PISA). The PISA may be caused by, for example, a user sleeping on the CGM, which may affect the ability of the CGM to accurately measure blood glucose. In the example, the AP application may evaluate the pressure measurements and determine whether the sensor is experiencing PISA and the extent to which the PISA is affecting a user's blood glucose measurement values.

In a further example, the CGM may occasionally fail to provide a blood glucose measurement to the AP application. The AP application may monitor the number of times that the CGM fails to deliver the blood glucose measurement (i.e., "missing blood glucose measurements"). In an example, the AP application may identify significant increases in missing blood glucose measurement values by tracking an increase in the frequency of calibrations and occurrences of other CGM characteristic error events. The AP application may use the identified increases in missing blood glucose measurements and occurrences of other CGM characteristic error events to determine possible CGM sensor or drug delivery device (i.e., pump) site issues (such as buildup of scar tissue or the like). In response to determining the possible CGM sensor or drug delivery device site issues, the AP application may respond accordingly. For example, the AP application may generate prompts requesting a user to relocate either the CGM sensor or drug delivery device to another site on the user's body.

In the example, the presence of faults within the available data themselves may be utilized as another source of data. For example, the faults may include missing EGV values, PISA events, and or non-physiological jumps in EGV values which can occur due to user calibrations or sensor noise. In response to the missing electronic glucose values (EGV), PISA events, and/or significant jumps in interaction with the AP application or CGM (for example, more frequent calibrations, other noise, or the like), the AP application may become more conservative in the delivery of insulin for the purpose of reducing blood glucose or allowing blood glucose to rise. In an example, the average rate of incidence of these faults may be characterized for each individual user over multiple usage sessions with an AID system managed by an AP application.

In another example, if faults occur more often compared to a standard rate of incidence (determined across a large number of users of the AID system), the high occurrence of faults may indicate an abnormal site issue or change in user behavior which may necessitate a more conservative automated insulin delivery behavior.

Figure 4A:
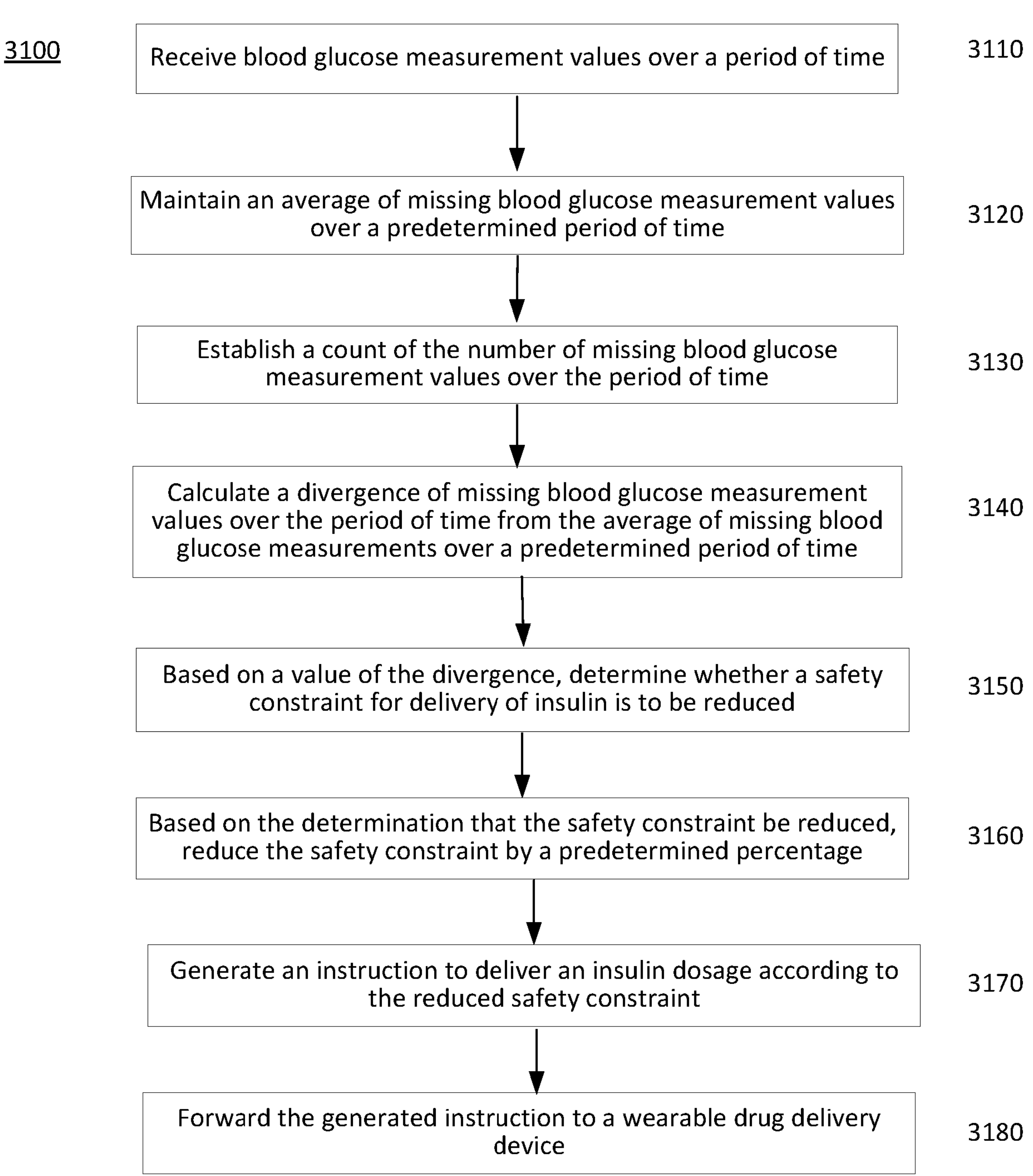
FIG. 4A illustrates a flow chart of another example of a process for adjusting a safety constraint based on missing blood glucose measurement.

An example of a process 3100 that accounts for the missing blood glucose measurements is illustrated in FIG. 4A. In the example of FIG. 4A, the AP application may receive an AP application or an algorithm executing on a processor may identify a blood glucose measurement as missing when the blood glucose measurement is not received at an expected time (e.g., every 5 minutes or the like), or within some time tolerance before or after the expected time. An AP application or an algorithm may be operable to receive blood glucose measurements from a blood glucose monitor over a period of time (3110). For example, the AP application may be executing on a personal diabetes management device or the algorithm may be executing on a drug delivery device. The respective AP application or algorithm may be further operable to maintain an average of missing blood glucose measurements over a predetermined time period (3120). The respective AP Application or algorithm may be operable to establish a count of the number of missing blood glucose measurements over the period of time (3130). For example, a predetermined number of blood glucose measurements (e.g., electronic glucose values (EGV)) are expected to be missing due to various reasons, such as loss of communication between the CGM and the AP application (or algorithm), noisy sensor site, sensor warmup, or the like.

At 3140, the AP application or algorithm may be operable to calculate a divergence of missing blood glucose measurements over the period of time from the average of missing blood glucose measurements over a predetermined time period. In an example, the divergence in missing blood glucose measurements $D_m$ may be calculated based on the following $$D_m(i) = \frac{M(i) - \overline{M}}{\overline{M}}$$

where M represents the number of missing blood glucose measurements values per a period of time, M.dash is an average number of missing blood glucose measurements values (EGV) per a predetermined time period, and (i) is each missing blood glucose measurements value (EGV) over the predetermined time period (which may equal the current cycle, such as 24 hours or the like).

Based on a value of the divergence, the AP application or algorithm may be operable to determine whether a safety constraint for delivery of insulin is to be reduced (3150). In the example, if a value of Dm is greater than, for example, approximately 1.5 (which may be tuned based on age, insulin sensitivity, activity such as swimming, or other activity), the AP application or algorithm may interpret a greater divergence as an indication that the user's pump or sensor insertion sites may be sub optimal for the current usage session, and thus may desire to modify its behavior.

In response, the AP application or algorithm controlling the automated insulin delivery system may reduce a safety constraint by a predetermined percentage due to the additional available information regarding the user's current system setup (3160). A safety constraint may, for example, be one or more of a maximum amount of total daily insulin to be delivered to a user, a limit on a basal rate of insulin to be delivered, a limit based on the user's insulin-on-board value, a limit based on the user's glucose concentration value, or the like. The predetermined percentage may be 3%, 10%, 15%, or the like.

The AP application or algorithm may generate an instruction to deliver an insulin dosage according to the reduced safety constraint (3170). At 3180, the AP application or algorithm may forward the generated instruction to a wearable drug delivery device.

In another example, the number of times the user may activate the system to view their current system status can indicate the user's level of concern, awareness of their metrics, and likelihood of addressing risk events. An ultimate goal of an AID system is to allow the users to minimize their need for checking the status of their diseases. Therefore, in the examples, the average user interaction rate with an external interface device to the system, such as the PDM, may be assessed. Then, if the user interacts with the system at a significant higher rate than this average interaction rate over a short period, the AID system may determine that the user feels they are in a state where there is a risk of sub optimal control (such as exercise, or large feasts), without the need for additional user interaction. Accordingly, in addition to the data streams that are directly related to current data streams available within the system (such as insulin delivery history, known EGV values, user requested boluses and the like), the occurrence of user interactions themselves can also be utilized to characterize the user's behavior, the implications of the user's behavior, and the AID systems performance.

Figure 4B:
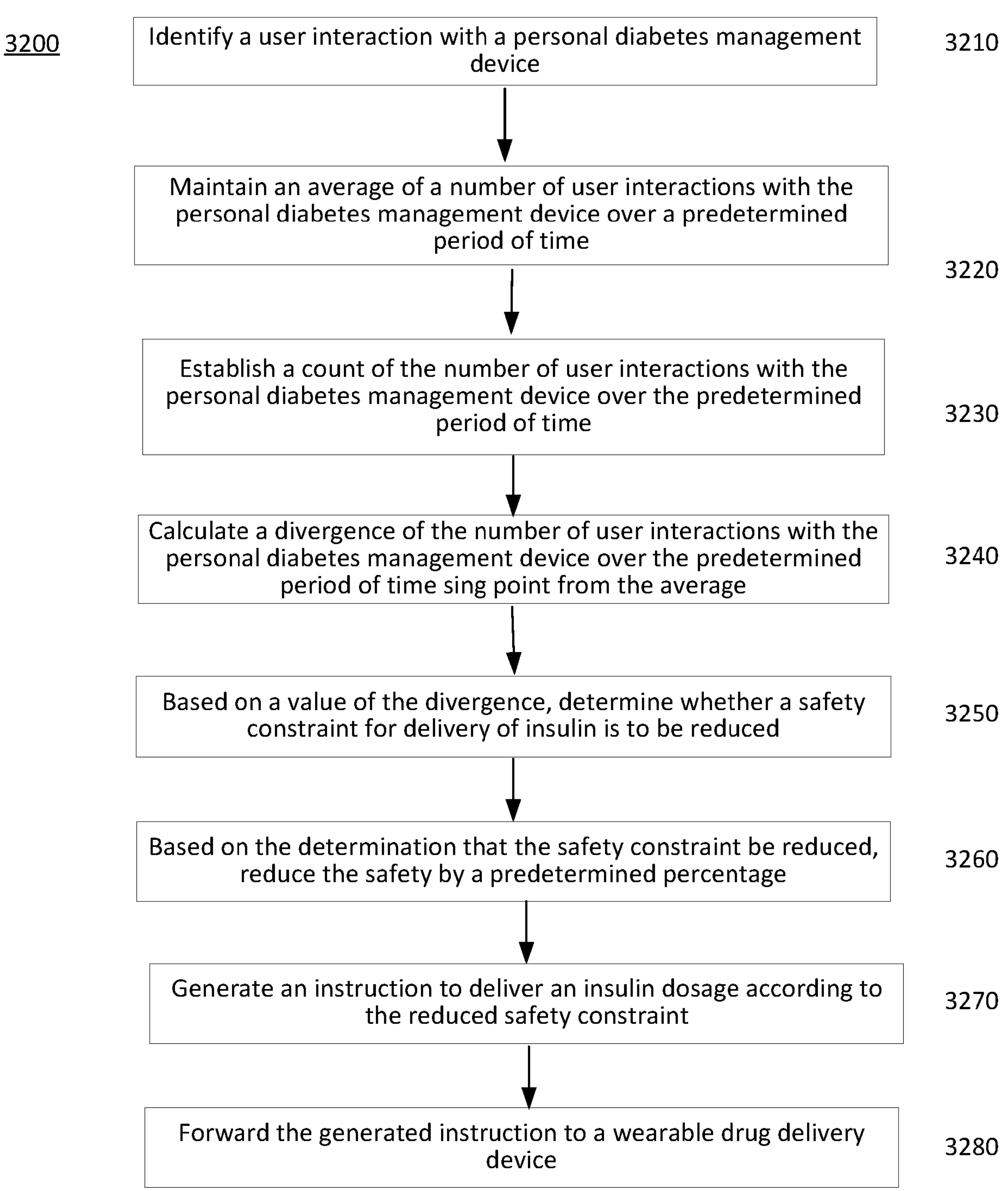
FIG. 4B illustrates a flow chart of another example of a process for adjusting a safety constraint based on user interactions with the system.

In another example as shown in FIG. 4B, the user interaction with an AID device interface, for example, on a personal diabetes management device may be utilized to determine a user's level of concern and likelihood of user intervention. FIG. 4B illustrates an example of a process that utilizes instances of user interaction with an AID device to make insulin dosing determinations.

In the example process 3200 of FIG. 4B, an AP application or algorithm executing on a PDM or drug delivery device, or both a PDM and a drug delivery device may be operable, at 3210, to identify a user interaction with a personal diabetes management device.

The AP application or algorithm executing on a PDM or drug delivery device, or both a PDM and a drug delivery device may be operable maintain an average of a number of user interactions with the personal diabetes management device over a predetermined time period (3220).

The AP application or algorithm may be further operable to establish a count of the number of user interactions with the personal diabetes management device over the predetermined time period (3230). Similar to the equation for determining the divergence of the number of missing EGVs from the average number of missing EGVs described above with respect to FIG. 4A, the divergence function may be used to calculate the divergence of the number of user interactions with the diabetes management system over a period of time from the average number of user interactions with the diabetes management system over the period of time (3240).

In an example, the divergence in user interactions $D_{UserInt}$ may be calculated as based on the following:

$$D_{UserInt}(i) = \frac{MUI(i) - \overline{MUI}}{\overline{MUI}}$$

where MUI represents the number of user interactions per a period of time, MUI.dash. is an average number of user interactions per a predetermined time period, and (i) is an occurrence of a user interaction over the predetermined time period (which may equal the current cycle, such 24 hours or the like).

Based on a value of the divergence, the AP application or algorithm may be operable to determine whether a safety constraint for delivery of insulin is to be reduced (3250). In the example, if a value of Dm is greater than, for example, approximately 1.5 (which may be tuned based on age, insulin sensitivity, activity such as swimming, or other activity), the AP application or algorithm may interpret a greater divergence as an indication that the user's pump or sensor insertion sites may be sub optimal for the current usage session.

In response, the AP application or algorithm controlling the automated insulin delivery system may reduce a safety constraint due to the additional available information regarding the user's current system setup (3260). A safety constraint may, for example, be one or more of a maximum amount of total daily insulin to be delivered to a user, a limit on a basal rate of insulin to be delivered, a limit based on the user's insulin-on-board value, a limit based on the user's glucose concentration value, or the like. The AP application or algorithm may generate an instruction to deliver an insulin dosage according to the reduced safety constraint (3270). At 3280, the AP application or algorithm may forward the generated instruction to a wearable drug delivery device.

Figure 4C:
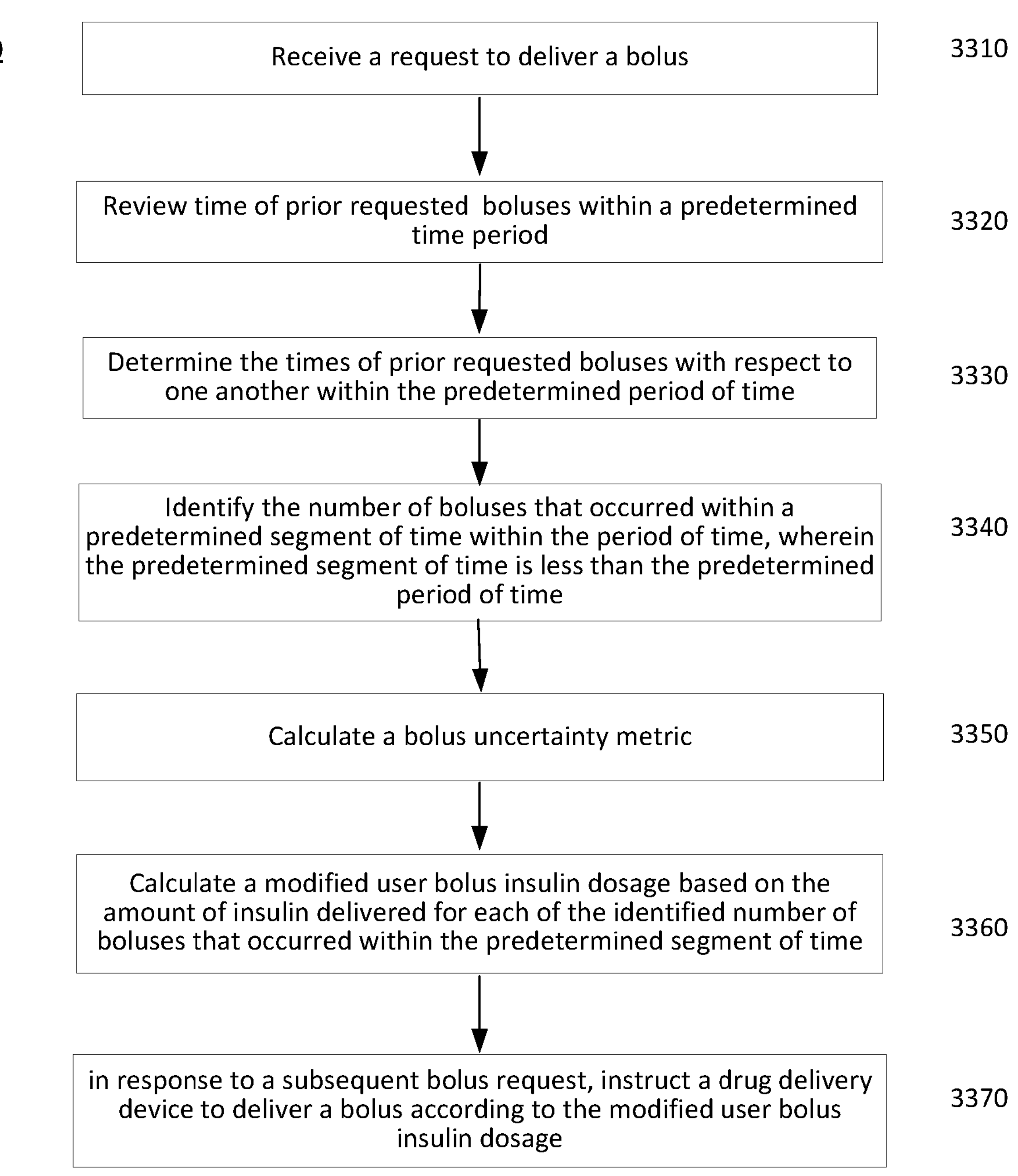
FIG. 4C illustrates a flow chart of another example of a process for adjusting a bolus uncertainty metric used in the calculation of a bolus insulin dose.

In another example, such as that shown in FIG. 4C, an AP application or algorithm may utilize user bolusing patterns to determine a relative accuracy of the user's bolusing needs. A bolus may be considered any dosage of insulin that is provided in response to a request by a user. FIG. 4C illustrates an example process for modifying a user's insulin bolus dosage. For example, a user may bolus multiple times within a short period of time rather than just once for each user interaction with the AP application or drug delivery device. For example, in the process 3300, an AP application or a drug delivery device may be operable to respond to a user's bolus request. In the process 3300, the AP application or an algorithm executing on the drug delivery device may receive a request to deliver a bolus (3310). The bolus request may be, for example, due to a user's desire to compensate for a mis-estimation of their insulin needs with their initial bolus, the user's desire to ingest snacks having additional carbohydrates beyond the user's original needs, exercise bolus, or any other reason that a user may want to receive a bolus dosage. In the example of the user's desire to ingest snacks with additional carbohydrates, the additional carbohydrates may be captured as an average bolus uncertainty metric. In the example process 3300, the AP application or algorithm may review, at 3320, a time that prior boluses were requested and whether any of the prior boluses were requested within a predetermined time period prior to the receipt of the request to deliver a bolus (at 3310). For example, the AP application or algorithm may consider a possibility that any boluses that occur within the expected insulin peak time of 90 minutes may be considered as a single bolus. In an example, the predetermined time period may be substantially equal to an expected insulin peak time, which may be 90 minutes, 105 minutes, or the like. The predetermined time period may be a number of set time windows of the same amount of time (e.g., 90 minutes, 105 minutes or the like), such as 8 am to 9:30 am, 12 pm to 1:30 pm, 1:30 pm to 3 pm, and so on. Alternatively, the predetermined time period may be a sliding window of a set time (e.g., 90 minutes, 105 minutes, or the like) that may begin at a particular time such as 6 am and continue to an expected bedtime for the user. The AP application or algorithm may determine the times of prior requested boluses with respect to one another within the predetermined period of time (3330).

The AP application or algorithm may identify the number of boluses that occurred within a predetermined segment of time within the period of time, wherein the predetermined segment of time is less than the predetermined time period (3340). Using the times of prior boluses and the number of boluses, the AP application or algorithm may calculate a bolus uncertainty metric (3350). The average bolus uncertainty metric may be used by the AP application (or algorithm) as a constraint or loosening in the evaluation of when to deliver insulin following these types of boluses (e.g., supplemental meal boluses, exercise boluses and the like).

In an example, an average bolus uncertainty metric $B_m$ may be calculated as:

$$B_{un} = \frac{\sum_{i=1}^{N_{bol,a}} N_{bol,un}}{N_{bol,a}}$$

where $N_{bol,un}$ may be characterized as a number of other bolus events that occurred within 90 minutes around any single bolus event, and $N_{bol,a}$ is an aggregate of the number of bolus events within the 90 minutes around the single bolus event. If $B_{un}$ is based on one bolus, $B_{un}$ may be called a bolus uncertainty metric.

In response to the calculated bolus uncertainty metric, the AP application or algorithm may calculate a modified user bolus insulin dosage based on the amount of insulin delivered for each of the identified number of boluses that occurred within the predetermined segment of time (3360). In response to the modified user bolus insulin dosage, at 3370, the AP application or algorithm, may generate commands for the drug delivery device to deliver the modified user bolus insulin dosage in response to a subsequent bolus request.

In a specific example, in the above formulation of $B_{un}$, the function double counts any one pair of boluses that occur within 90 minutes; therefore, a $B_{un}$ value of greater than 2 may be considered a high likelihood that the user's boluses generally are insufficient to cover the user's insulin needs. In response to the $B_{un}$ value being greater than 2, the AP application or algorithm that contributes to the management of the AID system may increase insulin deliveries based on the value of the $B_{un}$ parameter. For example, the modified user bolus insulin dosage calculated at 3360 may be increased based on the value of the $B_{un}$ parameter.

In another example, parameter identification techniques may be utilized to determine the importance of each additional parameter, and possibly generate a model of the user's behavior and their expected impact on AID outcomes. Further, the importance of each proposed data stream may be evaluated in real time to provide a broader overall picture of the user's diabetes care regimen beyond simple insulin delivery and glucose traces.

FIGS. 1-4C show a flowcharts of process examples for updating a duration of insulin action setting.

In the examples of FIGS. 1-4C, the example processes may be implemented by programming code, such as an AP application or an algorithm, which is executed by a processor. The AP application or algorithm when executed by a processor may utilize inputs and calculations as described with respect to the foregoing examples.

Figure 5:
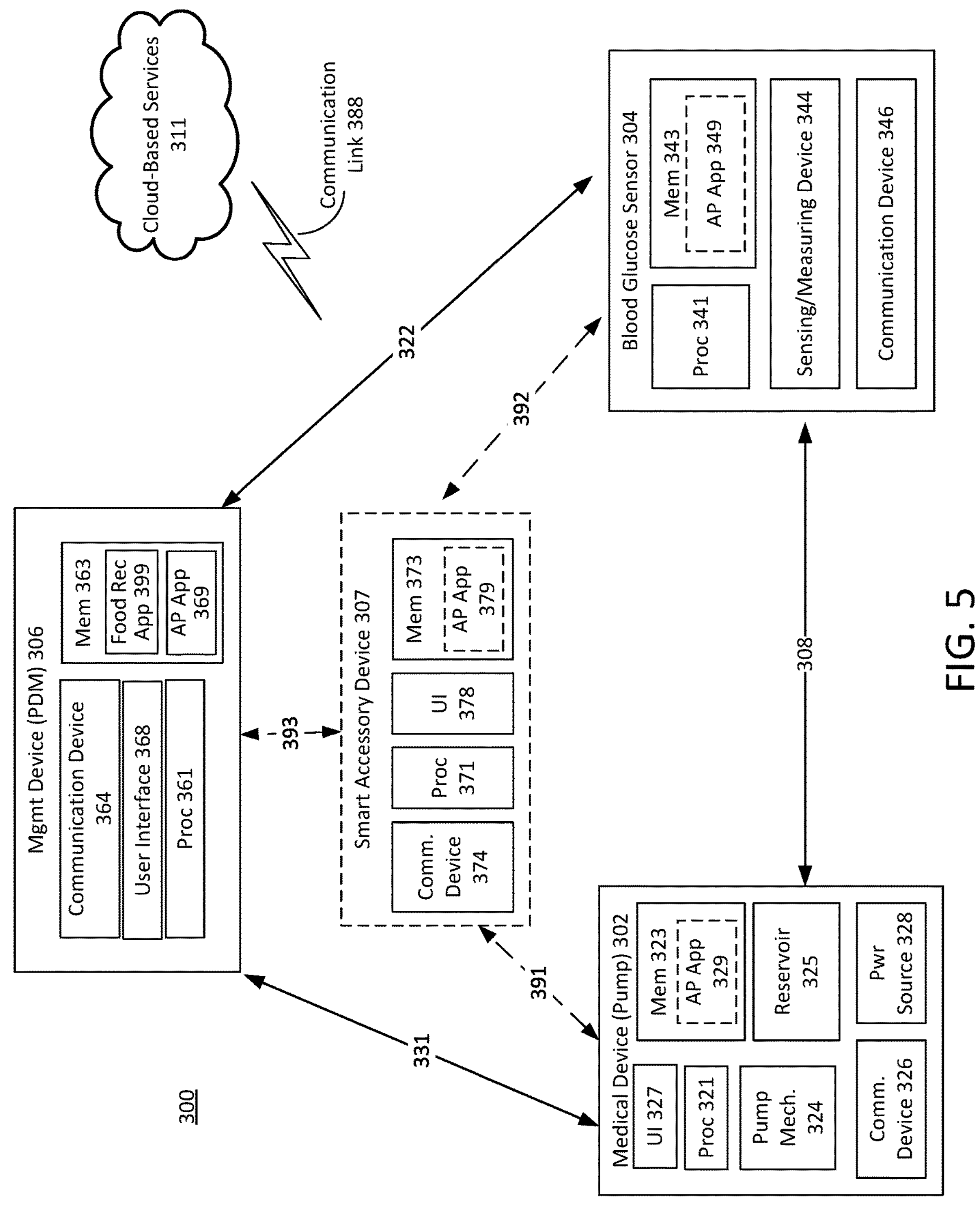
FIG. 5 illustrates a functional block diagram of drug delivery system suitable for implementing the example processes and techniques described herein.

It may be helpful to discuss an example of a drug delivery system that may implement the process example of FIGS. 1-4C. FIG. 5 illustrates an example of a drug delivery system 300.

The drug delivery system 300 may be operable to implement the process examples illustrated in FIGS. 1-4C by executing an AP application or algorithm that includes functionality to determine when to soften upper bounds of insulin delivery and how much to soften the upper bound; predict future blood glucose measurement values by calculating deviations between predicted blood glucose measurement values and additional blood glucose measurement values; determining a gain value for use with a model of predicting a user's blood glucose measurement values and determining future insulin dosages; determine safety constraints based on an evaluation of missing blood glucose measurement values; determine safety constraints based on an evaluation of a user's increased interaction with an automatic insulin delivery device; and calculate a bolus uncertainty metric to determine an amount of insulin to be provided in a bolus dosage in response to a bolus request.

The drug delivery system 300 may be an automated drug delivery system that may include a medical device (pump) 302 (also referred to as "a drug delivery device" or "a wearable drug delivery device"), a blood glucose sensor 304 (also referred to as "a continuous glucose monitor" or "a blood glucose measurement device"), and a management device (PDM) 306. The system 300, in an example, may also include a smart accessory device 307, which may be operable to communicate with the other components of system 300 either via a wired or wireless communication link, such as 391, 392 or 393.

In an example, the medical device 302 may be attached to the body of a user, such as a patient or diabetic, and may deliver any therapeutic agent, including any drug or medicine, such as insulin, morphine or the like, to the user. The medical device 302 may, for example, be a wearable device worn by the user. For example, the medical device 302 may be directly coupled to a user (e.g., directly attached to a body part and/or skin of the user via an adhesive or the like). In an example, a surface of the medical device 302 may include an adhesive (not shown) to facilitate attachment to a user.

The medical device 302 may include a number of components to facilitate automated delivery of a drug (also referred to as a therapeutic agent) to the user. The medical device 302 may be operable to store the drug (i.e., insulin) and to provide the drug to the user. The medical device 302 is often referred to as a pump, or an insulin pump, in reference to the operation of expelling insulin from the reservoir 325 for delivery to the user. While the examples refer to the reservoir 325 storing insulin, the reservoir 325 may be operable to store other drugs or therapeutic agents, such as glucagon, morphine, chemotherapy drugs, or the like, that are suitable for automated delivery.

In various examples, the medical device 302 may be an automated, wearable drug delivery device. For example, the medical device 302 may include a reservoir 325 for storing the drug (such as insulin), a needle or cannula (not shown) for delivering the drug into the body of the user (which may be done subcutaneously, intraperitoneally, or intravenously), and a pump mechanism (mech.) 324, or other drive mechanism, for transferring the drug from the reservoir 325, through a needle or cannula (not shown), and into the user. The pump mechanism 324 may be fluidly coupled to reservoir 325, and communicatively coupled to the medical device processor 321. For example, the pump mechanism 324 may be operable to deliver insulin based on actuation signals from the medical device processor 321, which may receive command signals from an AP application 369 (or the image-based bolus estimation application 399) of the PDM 306, or one of the AP applications 329, 349 or 379 when in control of the system 300. In a further example, the medical device processor 321 may be operable to receive a command signal from the PDM 306. The command signal including a recommended bolus dosage may be generated by either the image-based bolus estimation application 399 or the AP application 369. The processor 321 may be further operable to generate an actuation signal based on the recommended bolus dosage in the command signal. The processor 321 via a connection to inputs of the pump mechanism 324 may actuate the pump mechanism by applying the actuation signal to the input of the pump mechanism 324. An insulin dosage according to the recommended bolus dosage may be delivered to the user by the pump mechanism in response to the applied actuation signal.

The medical device 302 may also include a power source 328, such as a battery, a piezoelectric device, or the like, for supplying electrical power to the pump mechanism 324 and/or other components (such as the processor 321, memory 323, and the communication device 326) of the medical device 302. Although not shown, an electrical power supply for supplying electrical power may similarly be included in each of the sensor 304, the smart accessory device 307 and the management device (PDM) 306.

The blood glucose sensor 304 may be a device communicatively coupled to the processor 361 or 321 and may be operable to measure a blood glucose value at a predetermined time interval, such as every 5 minutes, or the like. The blood glucose sensor 304 may provide a number of blood glucose measurement values to the AP applications (e.g., 329, 349, 369, or 379) operating on the respective devices.

The medical device 302 may provide the insulin stored in reservoir 325 to the user based on information (e.g., blood glucose measurement values, predicted future blood glucose measurements, evaluations based on a user request for a bolus, an user interaction with PDM 306, medical device 302, sensor 304 or smart accessory device 307), evaluations of missing blood glucose measurements and the other information provided by the sensor 304, smart accessory device 307, and/or the management device (PDM) 306. For example, the medical device 302 may contain analog and/or digital circuitry that may be implemented as a processor 321 (or controller) for controlling the delivery of the drug or therapeutic agent. The circuitry used to implement the processor 321 may include discrete, specialized logic and/or components, an application-specific integrated circuit, a microcontroller or processor that executes software instructions, firmware, programming instructions or programming code (enabling, for example, the artificial pancreas application (AP App) 329 as well as the process examples of FIGS. 1-4C and 6) stored in memory 323, or any combination thereof. For example, the processor 321 may execute a control algorithm, such as an artificial pancreas application 329, and other programming code that may make the processor 321 operable to cause the pump to deliver doses of the drug or therapeutic agent to a user at predetermined intervals or as needed to bring blood glucose measurement values to a target blood glucose value. In an example, the AP application (App) 329 may include programming code that is operable upon execution by the processor 321 to provide the example processes for adjusting or modifying duration of insulin action settings, confidence values, insulin delivery settings, storing blood glucose measurement values in memory, or the like as described with reference to FIGS. 1-4C and 6A-E. The size and/or timing of the doses may be programmed, for example, into an artificial pancreas application 329 by the user or by a third party (such as a health care provider, medical device manufacturer, or the like) using a wired or wireless link, such as 331, between the medical device 302 and a management device 306 or other device, such as a computing device at a healthcare provider facility. In an example, the pump or medical device 302 is communicatively coupled to the processor 361 of the management device via the wireless link 331 or via a wireless link, such as 391 from smart accessory device 307 or 308 from the sensor 304. The pump mechanism 324 of the medical device 302 may be operable to receive an actuation signal from the processor 361, and in response to receiving a command signal or actuation signal, expel insulin from the reservoir 325 based on the evaluations and process steps performed in the process examples of FIGS. 1-4C and 6A-E.

In an operational example, the AP application 369 may be executing in the management device 306 and control delivery of insulin. For example, the AP application 369 may be operable to determine timing of an insulin dose and may output a command signal to the medical device 302 that actuates the pump mechanism 324 to deliver insulin dose based on the evaluations and process steps performed in the process examples of FIGS. 1-4C and 6A-E.

The other devices in the system 300, such as management device 306, smart accessory device 307 and sensor 304, may also be operable to perform various functions including controlling the medical device 302. For example, the management device 306 may include a communication device 364, a processor 361, and a management device memory 363. The management device memory 363 may store an instance of the AP application 369 that includes programming code, that when executed by the processor 361 provides the process examples described with reference to the examples of FIGS. 1-4C and 6A-E. In addition, the management device memory 363 may store an instance of image-based bolus estimation application 399 that is described in more detail with reference to FIGS. 6A-F, 7 and 8. The processor 361 may be operable to implement the image-based bolus estimation application 399 separate from the AP application 369 or in cooperation with the AP application 369. The management device memory 363 may also store programming code for providing the process examples described with reference to the examples of FIGS. 1-8.

The smart accessory device 307 may be, for example, an Apple Watch®, other wearable smart device, including eyeglasses, provided by other manufacturers, a global positioning system-enabled wearable, a wearable fitness device, smart clothing, or the like. Similar to the management device 306, the smart accessory device 307 may also be operable to perform various functions including controlling the medical device 302. For example, the smart accessory device 307 may include a communication device 374, a processor 371, and a memory 373. The memory 373 may store an instance of the AP application 379 that includes programming code for providing the process examples described with reference to the examples of FIGS. 1 and 2. The memory 373 may also as store programming code and be operable to store data related to the AP application 379. The sensor 304 of system 300 may be a continuous glucose monitor (CGM) as described above, that may include a processor 341, a memory 343, a sensing or measuring device 344, and a communication device 346. The memory 343 may, for example, store an instance of an AP application 349 as well as other programming code and be operable to store data related to the AP application 349 and process examples described with reference to FIGS. 1-4C, 6B and 6D. The AP application 349 may also include programming code for providing the process examples described with reference to the examples of FIGS. 1-8

Instructions for determining the delivery of the drug or therapeutic agent (e.g., as a bolus dosage) to the user (e.g., the size and/or timing of any doses of the drug or therapeutic agent) may originate locally by the medical device 302 or may originate remotely and be provided to the medical device 302. In an example of a local determination of drug or therapeutic agent delivery, programming instructions, such as an instance of the artificial pancreas application 329, stored in the memory 323 that is coupled to the medical device 302 may be used to make determinations by the medical device 302. In addition, the medical device 302 may be operable to communicate with the cloud-based services 311 via the communication device 326 and the communication link 388.

Alternatively, the remote instructions may be provided to the medical device 302 over a wired or wireless link (such as 331) by the management device (PDM) 306, which has a processor 361 that executes an instance of the artificial pancreas application 369, or the smart accessory device 307 (via communication link 391), which has a processor 371 that executes an instance of the artificial pancreas application 369 as well as other programming code for controlling various devices, such as the medical device 302, smart accessory device 307 and/or sensor 304. The medical device 302 may execute any received instructions (originating internally or from the management device 306) for the delivery of the drug or therapeutic agent to the user. In this way, the delivery of the drug or therapeutic agent to a user may be automated.

In various examples, the medical device 302 may communicate via a wireless link 331 with the management device 306. The management device 306 may be an electronic device such as, for example, a smart phone, a tablet, a dedicated diabetes therapy management device, or the like. The management device 306 may be a wearable wireless accessory device. The wireless links 308, 331, 322, 391, 392 and 393 may be any type of wireless link provided by any known wireless standard. As an example, the wireless links 308, 331, 322, 391, 392 and 393 may enable communications between the medical device 302, the management device 306 and sensor 304 based on, for example, Bluetooth®, Wi-Fi®, a near-field communication standard, a cellular standard, or any other wireless optical or radio-frequency protocol.

The sensor 304 may be a glucose sensor operable to measure blood glucose and output a blood glucose value or data that is representative of a blood glucose value. For example, the sensor 304 may be a glucose monitor or a continuous glucose monitor (CGM). The sensor 304 may include a processor 341, a memory 343, a sensing/measuring device 344, and communication device 346. The communication device 346 of sensor 304 may include one or more sensing elements, an electronic transmitter, receiver, and/or transceiver for communicating with the management device 306 over a wireless link 322 or with medical device 302 over the wireless link 308. The sensing/measuring device 344 may include one or more sensing elements, such as a glucose measurement, heart rate monitor, or the like. The processor 341 may include discrete, specialized logic and/or components, an application-specific integrated circuit, a microcontroller or processor that executes software instructions, firmware, programming instructions stored in memory (such as memory 343), or any combination thereof. For example, the memory 343 may store an instance of an AP application 349 that is executable by the processor 341.

Although the sensor 304 is depicted as separate from the medical device 302, in various examples, the sensor 304 and medical device 302 may be incorporated into the same unit. That is, in various examples, the sensor 304 may be a part of the medical device 302 and contained within the same housing of the medical device 302 (e.g., the sensor 304 may be positioned within or embedded within the medical device 302). Glucose monitoring data (e.g., measured blood glucose values) determined by the sensor 304 may be provided to the medical device 302, smart accessory device 307 and/or the management device 306 and may be used to perform the functions and deliver doses of insulin for automated delivery of insulin by the medical device 302 as described with reference to the examples of FIGS. 1-8.

The sensor 304 may also be coupled to the user by, for example, adhesive or the like and may provide information or data on one or more medical conditions and/or physical attributes of the user. The information or data provided by the sensor 304 may be used to adjust drug delivery operations of the medical device 302.

In an example, the management device 306 may be a computing device operable to manage a personal diabetes treatment plan via an AP application or an algorithm. The management device 306 may be used to program or adjust operation of the medical device 302 and/or the sensor 304. The management device 306 may be any portable electronic, computing device including, for example, a dedicated controller, such as processor 361, a smartphone, or a tablet. In an example, the management device (PDM) 306 may include a processor 361, a management device management device memory 363, and a communication device 364. The management device 306 may contain analog and/or digital circuitry that may be implemented as a processor 361 (or controller) for executing processes to manage a user's blood glucose levels and for controlling the delivery of the drug or therapeutic agent to the user. The processor 361 may also be operable to execute programming code stored in the management device management device memory 363. For example, the management device management device memory 363 may be operable to store an artificial pancreas (AP) application 369 that may be executed by the processor 361. The processor 361 may when executing the artificial pancreas application 369 may be operable to perform various functions, such as those described with respect to the examples in FIGS. 1-4C and 6. The communication device 364 may be a receiver, a transmitter, or a transceiver that operates according to one or more radio-frequency protocols. For example, the communication device 364 may include a cellular transceiver and a Bluetooth transceiver that enables the management device 306 to communicate with a data network via the cellular transceiver and with the sensor 304 and the medical device 302. The respective transceivers of communication device 364 may be operable to transmit signals containing information useable by or generated by the AP application or the like. The communication devices 326, 346 and 376 of respective medical device 302, sensor 304 and smart accessory device 307 may also be operable to transmit signals containing information useable by or generated by the AP application or the like.

The medical device 302 may communicate with the sensor 304 over a wireless link 308 and may communicate with the management device 306 over a wireless link 331. The sensor 304 and the management device 306 may communicate over a wireless link 322. The smart accessory device 307, when present, may communicate with the medical device 302, the sensor 304 and the management device 306 over wireless links 391, 392 and 393, respectively. The wireless links 308, 331, 322, 391, 392 and 393 may be any type of wireless link operating using known wireless standards or proprietary standards. As an example, the wireless links 308, 331, 322, 391, 392 and 393 may provide communication links based on Bluetooth®, Wi-Fi, a near-field communication standard, a cellular standard, or any other wireless protocol via the respective communication devices 326, 346 and 364. In some examples, the medical device 302 and/or the management device 306 may include a user interface 327, 378 and 368, respectively, such as a keypad, a touchscreen display, levers, buttons, a microphone, a speaker, a display, or the like, that is operable to allow a user to enter information and allow the management device to output information for presentation to the user.

In various examples, the drug delivery system 300 may implement the artificial pancreas (AP) algorithm (and/or provide AP functionality) to govern or control automated delivery of insulin to a user (e.g., to maintain euglycemia—a normal level of glucose in the blood). The AP application may be implemented by the medical device 302 and/or the sensor 304. The AP application may be used to determine the times and dosages of insulin delivery. In various examples, the AP application may determine the times and dosages for delivery based on information known about the user, such as the user's sex, age, weight, or height, and/or on information gathered about a physical attribute or condition of the user (e.g., from the sensor 304). For example, the AP application may determine an appropriate delivery of insulin based on glucose level monitoring of the user through the sensor 304. The AP application may also allow the user to adjust insulin delivery. For example, the AP application may allow the user to issue (e.g., via an input) commands to the medical device 302, such as a command to deliver an insulin bolus. In some examples, different functions of the AP application may be distributed among two or more of the management device 306, the medical device (pump) 302 or the sensor 304. In other examples, the different functions of the AP application may be performed by one device, such the management device 306, the medical device (pump) 302 or the sensor 304.

As described herein, the drug delivery system 300 or any component thereof, such as the medical device may be considered to provide AP functionality or to implement an AP application. Accordingly, references to the AP application (e.g., functionality, operations, or capabilities thereof) are made for convenience and may refer to and/or include operations and/or functionalities of the drug delivery system 300 or any constituent component thereof (e.g., the medical device 302 and/or the management device 306). The drug delivery system 300—for example, as an insulin delivery system implementing an AP application—may be considered to be a drug delivery system or an AP application-based delivery system that uses sensor inputs (e.g., data collected by the sensor 304).

In an example, one or more of the devices, 302, 304, 306 or 307 may be operable to communicate via a wireless communication link 388 with cloud-based services 311. The cloud-based services 311 may utilize servers and data storage (not shown). The communication link 388 may be a cellular link, a Wi-Fi link, a Bluetooth link, or a combination thereof, that is established between the respective devices 302, 304, 306 or 307 of system 300. The data storage provided by the cloud-based services 311 may store anonymized data, such as user weight, blood glucose measurements, age, meal carbohydrate information, or the like. In addition, the cloud-based services 311 may process the anonymized data from multiple users to provide generalized information related to the various parameters used by the AP application. For example, an age-based general target blood glucose value may be derived from the anonymized data, which may be helpful when a user first begins using a system such as 300. The cloud-based services 311 may also provide processing services for the system 300, such as performing the process 100 in the example of FIG. 2 or additional processes, such as that described below with reference to FIG. 3.

In an example, the device 302 includes a communication device 364, which as described above may be a receiver, a transmitter, or a transceiver that operates according to one or more radio-frequency protocols, such as Bluetooth, Wi-Fi, a near-field communication standard, a cellular standard, that may enable the respective device to communicate with the cloud-based services 311. For example, outputs from the sensor 304 or the medical device (pump) 302 may be transmitted to the cloud-based services 311 for storage or processing via the transceivers of communication device 364. Similarly, medical device 302, management device 306 and sensor 304 may be operable to communicate with the cloud-based services 311 via the communication link 388.

In an example, the respective receiver or transceiver of each respective device, 302, 306 or 307, may be operable to receive signals containing respective blood glucose measurement values of the number of blood glucose measurement values that may be transmitted by the sensor 304. The respective processor of each respective device 302, 306 or 307 may be operable to store each of the respective blood glucose measurement values in a respective memory, such as 323, 363 or 373. The respective blood glucose measurement values may be stored as data related to the artificial pancreas algorithm, such as 329, 349, 369 or 379. In a further example, the AP application operating on any of the management device 306, the smart accessory device 307, or sensor 304 may be operable to transmit, via a transceiver implemented by a respective communication device, 364, 374, 346, a control signal for receipt by a medical device. In the example, the control signal may indicate an amount of insulin to be expelled by the medical device 302. In yet a further example of processes that the components of system 300 may be operable to perform include providing a capability to assist a user with the approximation of the number of carbohydrates that may be in a user's meal by utilizing an image-based bolus estimation application 399.

Various operational scenarios and examples of processes performed by the system 300 are described herein. For example, the system 300 may be operable to implement the process examples of FIG. 1-4C, 6A, 6B and 6E.

The following examples are related to estimating a bolus amount in response to consumption of a meal using a model supplemented with visual image recognition. In the examples, the image-based bolus estimation application applies a model using visual image recognition to approximate carbohydrates contained in the food by obtaining an image of the food, an image of a food label, a computer-readable code associated with the food label, a manual input, a combination of food labels and food images directly. As explained with reference to the following examples, the visual image recognition may be utilized to provide information usable in the generation of a bolus dosage estimate or recommendation.

Figure 6A:
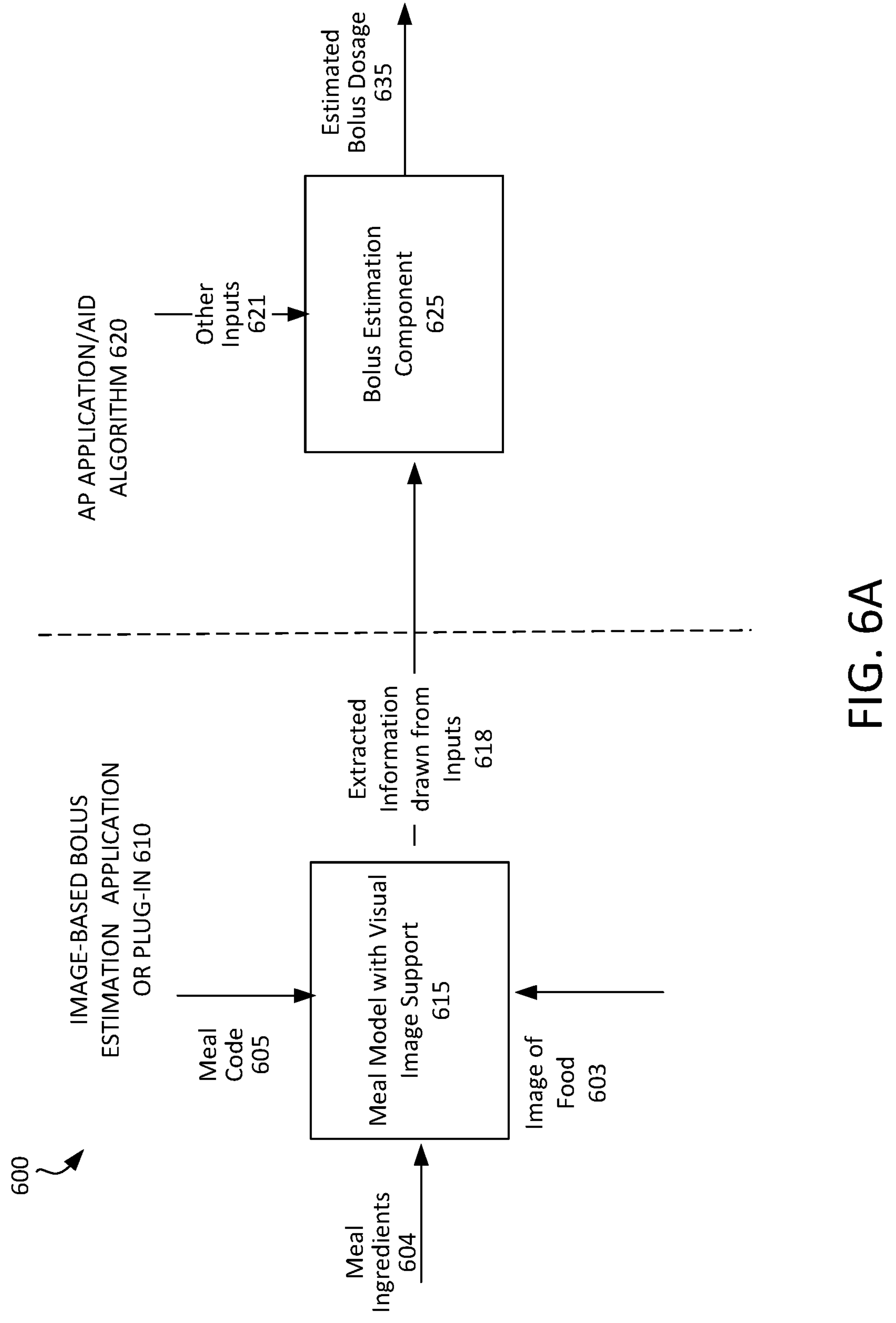
FIG. 6A shows a block diagram of an example of a meal compensation system that includes an image-based bolus estimation application and an AP application or AID algorithm.

FIG. 6A shows a block diagram of an example of a meal compensation system that includes an image-based bolus estimation application and an AP application or AID algorithm. The image-based bolus estimation application or plug-in 610 may cooperate with the AP application or AID algorithm 620 to provide an image recognition component that is configured to recognize food related items in an image. For the example, the image-based bolus estimation application or plug-in 610 of the meal compensation system 600 may employ a meal model with visual image support 615 that accepts a number of inputs. The number of inputs may include, for example, information from a code, such as a meal code 605, a list of meal ingredients 604, an image of food 603, a user input, or the like. The meal model with visual image support 615 may include a number of algorithms and functions that operate in cooperation to extract information related to a meal being consumed or about to be consumed. The meal model with visual image support 615 may also receive a meal code 605 and images of food 603 provided via a camera on a mobile device or PDM (shown in another example) that is executing the image-based bolus estimation application or plug-in 610. In addition, a processor of the mobile device or PDM may execute programming code to implement the meal model with visual image support 615 that uses the inputs, such as image of food 603, meal ingredients 604 and meal code 605 to extract information from the inputs. Although not shown, other inputs to the meal model with visual image support 615 may also be received from a user via a keypad or another input device, such as a microphone, a touchscreen display, or the like that is coupled to or integral to the mobile device or PDM. For example, inputs in addition to the inputted images may include text, verbal identifications of the foods being consumed, or numbers which may be used to supplement the processing performed using the meal model with visual image support 615. An example of a text or verbal identification may include a meal code 605.

Figure 6B:
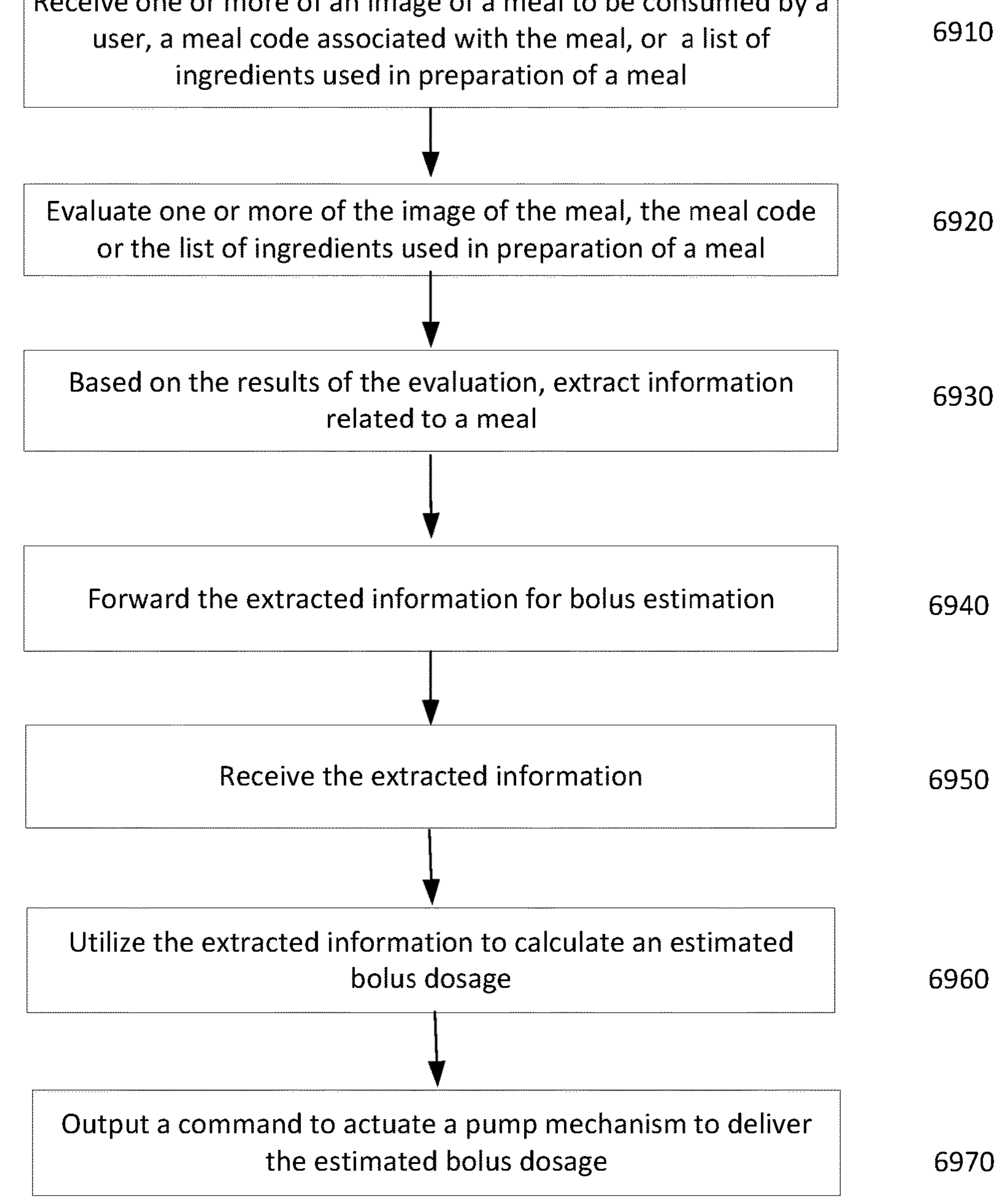

In an operational example, FIG. 6B illustrates a meal evaluation process that is operable to extract meal-related information from inputs received by an image-based bolus estimation application or plug-in, such as 610. As explained with reference to FIGS. 6A and 6B, the meal evaluation process 690 may enable the user to obtain food-related information from the meal code 605 which may, for example, allow a user to adjust the percentage of the actual meal consumed or adjust the percentage, type, or number of the raw materials or ingredients used in the preparation of the meal to accurately track the meal constituents. In a further example, the meal model with visual image support 615 may be operable to perform image recognition of an image of food 603 that was obtained by the image-based bolus estimation application or plug-in 610 via a user's device hosting the image-based bolus estimation application or plug-in 610.

In the example, an image-based bolus estimation application 610 may be a separate mobile computer application operable to interact with the AP application or AID algorithm 620 via, for example, an application program interface (API) of the AP application, or may be a plug-in to the AP application or AID algorithm 620. The image-based bolus estimation application 610 may, when executed by a processor, be operable to enable the processor to access a camera of a mobile device, such as PDM 306 or as shown and described in another example, such as that of FIG. 7 or 8, that may be operable to provide substantially the same functionality of a PDM.

The meal evaluation process 690 executed by the image-based bolus estimation application or plug-in 610 may be operable to receive one or more of: an image of a meal to be consumed by a user, a meal code associated with the meal, or a list of ingredients used in preparation of the meal (6910). For example, a food-related image may be obtained that includes at least one of a computer-readable data, image of a food, or image of a food label. At step 6910, a user may, for example, take a picture of their meal using a camera on their mobile device, which may be a smartphone or a PDM, such as 306 of FIG. 5, a web camera coupled to or integrated with a laptop computer, a camera of a wearable device, such as glasses, or the like. For example, an image-based bolus estimation application 610, which may be a plug-in to the AP application, may include programming code operable to provide image recognition and classification resources that may process the image of the meal in the received image. The image recognition and classification resources may be implemented as programming code that is included with the image-based bolus estimation application or plug-in 610 to the AP application or AID algorithm 620, may be provided by a cloud-based service, such as 311 of FIG. 5, or may be provided by a combination of both. The image recognition and classification resources may process the images provided by the camera of the mobile device or PDM, or the web camera to identify food, a type of the identified food, an estimated amount of food, and the like. A meal may include, for example, a drink consumed with, before and/or after the meal, dessert, a main course, appetizers or the like. In an example, the meal model with visual image support 615 may implement processing of the image data using one or more image processing techniques that may provide a recognition result or several probable recognition results.

In addition, or alternatively, at step 6910, the meal model with visual image support 615 may receive meal ingredients 604, for example, as a textual input from a user or as an image of recipe (e.g., a "screenshot" of the recipe for the meal about to be consumed). The meal model with visual image support 615 may be operable to perform optical character recognition (OCR) separately, or in combination with the performance of image recognition.

Also, at step 6910, the meal model with visual image support 615 may, in addition or alternatively, be operable to receive a meal code 605. A meal code 605 may be a computer-readable data code, examples of which may a QR code, a two-dimensional bar code, a data matrix code or other computer-readable code associated with a food label, a restaurant menu, food packaging, a food-related website, a food recipe, or the like. In the example, the computer-readable code associated with the food label may be included on packaged foods, or when a meal is prepared with a combination of foods associated with packaged discrete or semi-discrete ingredients that have an associated computer-readable code on the packaging.

Continuing with the operational example with regard to the meal code 605, the image-based bolus estimation application may be operable to access, via the meal model with visual image support 615, from the meal code 605 an address of a webpage (via a uniform resource locator (URL) embedded in the computer-readable code) or cause the launch of a mobile computer application that may have information related to the meal. For example, the meal model with visual image support 615 may interact with other applications and hardware, such as a cellular communication application and transceiver or data network application and transceiver (e.g., Wi-Fi), executing on a mobile device or PDM that enable information represented by the meal code 605 to be obtained. For example, the webpage may include nutritional information regarding the food to be consumed, serving size information, a restaurant where the food is sold, or the like. After accessing the webpage or the mobile computer application, the AP application may cause the presentation of information from the webpage on a display, such as a touchscreen display, of the mobile device or PDM.

At 6920, the recognition results of the image of food 603, the meal ingredients 604, the information pointed towards by the meal code 605, or a combination may be further processed using algorithms of the meal model with visual image support 615 that may be operable to evaluate and extract information, such as carbohydrate and other nutritional information of the meal as well as meal-related information, such as meal size or food categories (e.g., meat, vegetable, grain, dairy, or the like). In addition, at 6920, the meal ingredients 604 and meal code 605 may be evaluated for information related to the meal. The results of the evaluation may identify information related to the meal, such as the nutritional content, such as carbohydrate or caloric content, of the meal, the size of the meal, which may be based on the number of ounces of each category or type of food, or meal size category, such as small-medium-large size categories.

Upon evaluation of the one or more of the image of the meal, the meal code or the list of ingredients used in the preparation of the meal, the results of the evaluation may be processed to extract information usable by the meal model with visual image support 615 (6930). The extracted information may include carbohydrate information of each respective food recognized in the image of the food 603, carbohydrate information obtained from the meal ingredients 604 or the meal code 605, or the like. With the help of a depth sensor in the camera, the portion size can be a useful input to the bolus calculator. This information is also useful to categorize the meal as a small, a medium, or a large meal size. The image can also suggest a meal ratio with splits between carbohydrates, protein, and vegetables. Some users may have a meal ratio preference such as 30:30:40 or 40:30:30, or the like. In a further example, location information from the image or obtained from the device's GPS application may be used to determine if this is meal cooked at home or not (e.g., cooked at a restaurant or the like). Alternatively, a user may be asked via a prompt whether this is a home cooked meal if the location is home or is it a take-out meal. Additionally, the extracted information may also include information on other meal components, such as fat content or protein content, as well as general meal characteristics which may carry additional meal ingestion information, such as temperature (via visual cues such as steam; directly impacting timing of meal ingestion). The information can also be logged and be entered into a journal. The format of the extracted information may depend upon the AP application or AID algorithm 620 that interfaces with the image-based bolus estimation application or plug-in 610. The image-based bolus estimation application or plug-in 610 may be operable to process the inputted information (i.e., 603, 604 and 605) so the recognition results and/or extracted information meets the requirements of the AP application or AID algorithm 620.

The extracted information drawn from the inputs 618 may be forwarded by the image-based bolus estimation application or plug-in 610 to the AP application or AID algorithm 620 (6940). The AP application or AID algorithm 620 may receive the extracted information forwarded by the image-based bolus estimation application 610 via an API or another process (6950) from the image-based bolus estimation application or plug-in 620. In an example, the extracted information may include carbohydrate-related data that is obtained by processing the obtained food-related image.

At 6960, the bolus estimation component 625 executing as part of the AP application or AID algorithm 620 may be operable to utilize the extracted information to calculate an estimated bolus dosage, such as 635 of FIG. 6A, and control delivery of insulin. In addition, the bolus estimation component 625 may receive other inputs 621 to generate an estimated bolus dosage 635. The other inputs 621 may include several of the user's most recent blood glucose measurement values obtained from a sensor, such as 304 of FIG. 5, a blood glucose measurement value history, a rate of change of the user's blood glucose measurements (calculated over the last few hours or days), an indication of a user's amount of insulin onboard, or the like. Using the extracted information alone or the extracted information and information of the other inputs 621, the bolus estimation component 625 may generate an estimated bolus dosage 635 that is intended to compensate for the consumption of the meal. The estimated bolus dosage 635 may be a digital or analog signal that represents the dosage of insulin in units of insulin, or the like.

The estimated bolus dosage 635 calculated by the AP application or AID algorithm 620 may be used to further generate a command signal for commanding actuation of a pump mechanism in a medical device, such as 324 in device 302 of FIG. 5, to deliver an amount of insulin corresponding to the estimated bolus dosage 635. At the AP Application or AID algorithm 620, a command signal may be output to actuate a pump mechanism of a medical device to deliver an insulin dosage according to the recommended bolus dosage (6970).

Figure 6C:
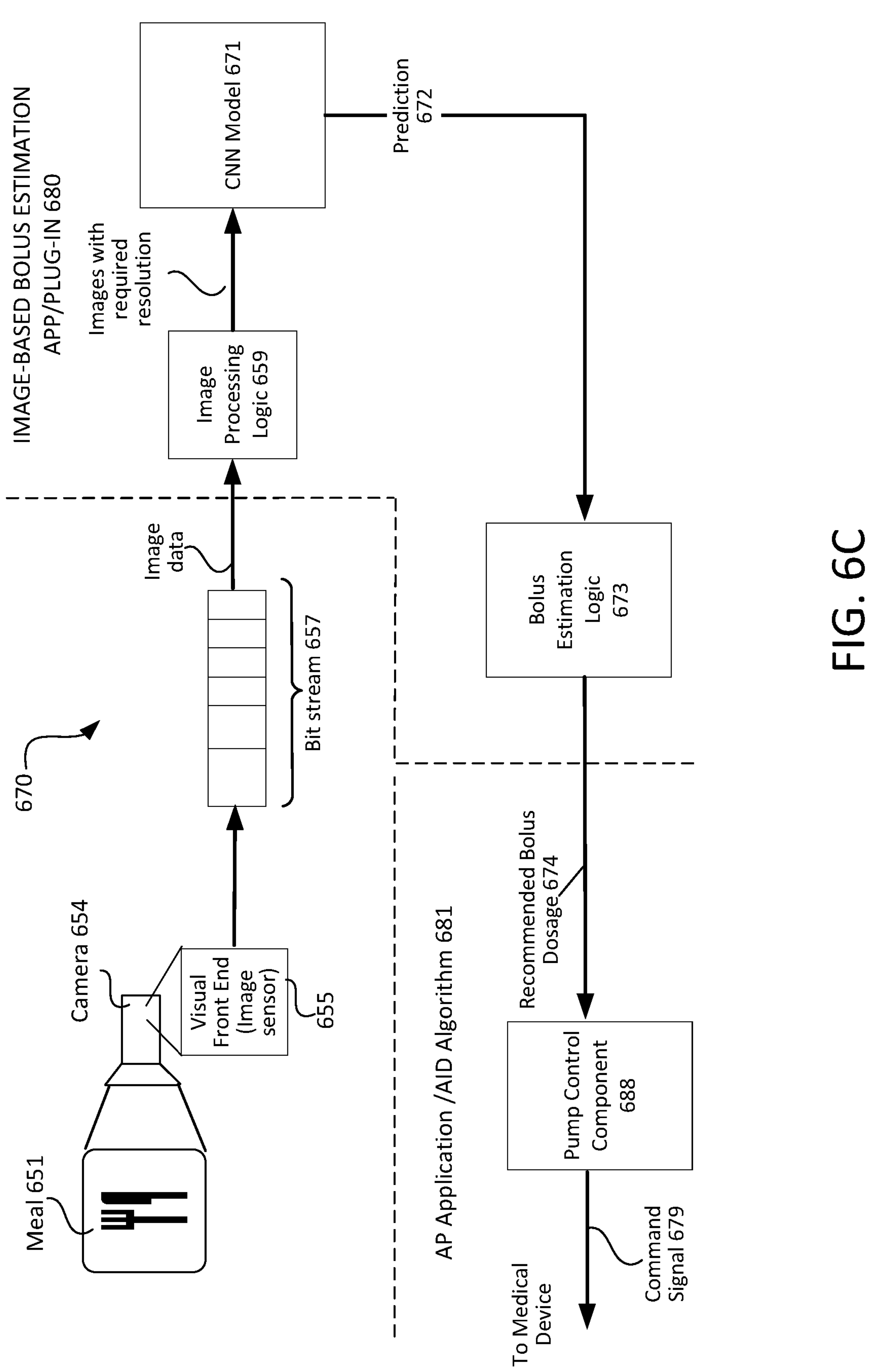
FIG. 6C illustrates an example of a convolutional neural network that may be implemented by the image-based bolus estimation application example of FIG. 6A.

An advantage of the present examples is an image recognition application that is operable to classify an image and provide that classification for estimating an insulin dosage for a specific user. The example of FIG. 6C illustrates a data flow example of a bolus estimation process that utilizes image classification predictions provided by a neural network model as an input for estimating an insulin dosage specific to the needs of a diabetic. FIG. 6C illustrates a data flow of a process 670 that includes functional block diagram representations of components of an image-based bolus estimation application. The image-based bolus estimation application/plug-in 680 may include an image processing pipeline that is operable to process image data, evaluate the processed image data to generate a classification prediction, and output a recommended bolus estimate.

An advantage of using images of a meal is the ability to later retrieve the image of the meal as well as the meal-related information. As a result, the user via a graphical user interface and through operations provided by the image-based bolus estimation application may use the images from the meals to track, store and perform search operations to go back in time to review foods consumed during a respective meal and view additional contemporaneous information, such as blood glucose measurements, insulin delivery, and user responses that correspond in time with the respective meal. For example, a user may be able to review an image of a meal and the user's blood glucose response to meals of a specific food composition, such as a large, medium-rare porterhouse steak, a piece of red velvet cake, or similar food that may not be frequently consumed.

As shown in the example of FIG. 6C, the image processing pipeline of the image-based bolus estimation application or plug-in 680 may include various components, such as a component that is operable to implement image processing logic 659, another component operable to implement a convolutional neural network model 671, and a further component operable to implement bolus estimation logic 673 that generates a bolus estimate. The image-based bolus estimation application or plug-in 680 enables extracting food-related information from an image for further enhancing the bolus dosage estimation.

In the example, the CNN model 671 may be a neural network that has been pre-trained using images of food acquired from the public domain that is operable to provide an image classification result (e.g., type or category of food) or recognition result (e.g., specific food, such as pasta, steak, broccoli or the like). In this example, the results of the image classification are referred to as a prediction 672 that is forwarded to the bolus estimate logic 673.

The image-based bolus estimation application or plug-in 680 is operable to communicate with a camera. The camera 654 in the example of FIG. 6C may be a body worn camera or a wearable device, such as Google Glass® or a Go Pro® camera, a handheld camera, such as a mobile device camera, a smartphone camera, or the like. The camera 654 may include a visual front end 655, which is an image sensor that outputs detected image data. For example, the bitstream 657 may be obtained from continuous image data obtained by the visual front end 655 (i.e., an image sensor) of the camera 654.

In the example, the visual image pipeline of the image-based bolus estimation application or plug-in 680 may include image processing logic 659 and a convolutional neural network (CNN) model 671. The image processing logic 659 may, if necessary, modify the image data in the bitstream 657 to place the image data in a format that meets the input requirements of the CNN model 671. For example, the CNN model 671 be operable to process image data having a required resolution, the image processing logic 659 may modify the resolution of the image data from the bitstream 657 to meet the resolution requirements of the CNN model 671. In an example, the modification of the resolution by the image processing logic 659 may be executed by application of image processing techniques, such as spatial domain or frequency domain enhancements, which increase or reduce image resolution of the image data.

The CNN model 671 may, for example, be a pretrained CNN model trained with food sources (e.g., image databases of images of food, such as the Pittsburgh fast-food image dataset, or the like). In some examples, the visual image pipeline may require a continuous image stream which detects a meal in approximately front of the user and identifies a start of the meal based on a change in food portion that is detected as time progresses. In this manner, the CNN model 671 may be operable to calculate the portion sizes consumed and multiple servings. In an example, the accuracy of the pre-trained CNN model 671 may be improved by receiving image data from a high number of image data sources. In addition, or alternatively, the CNN model 671 may be personalized to a limited set of food sources (e.g., meats, vegetables and drinks) generally consumed as regular meals.

The output of the CNN model 671 may be a prediction 672 of the food in the image data. For example, the prediction 672 may be a signal that includes a prediction of one or more different classifications of foods (e.g., a meat, a starch, a vegetable, a fruit, a candy, a flavored drink, water, or the like) that encompass the meal captured by the visual front end 655 as well as the predicted quantity of each classification of food. In an example, the meal 651 from which the image data was collected may include, for example, potatoes, beef or pork, and green beans. A prediction 672 based on the image data of the potatoes, beef or pork, and green beans may provide data indicating a starch, a meat and a vegetable, and respective estimates of portion sizes, such as 6 ounces of potatoes, 3 ounces of meat, 4 ounces of vegetables, or the like. Additionally, a processor, such as 361 of FIG. 5, may, in response to the prediction 672 output from the CNN model 671, provide a confirmation prompt on a user interface which may be used to verify the predicted food classification (e.g., meat, starch, vegetable, fruit, candy, dairy, flavored drink, water, or the like) and the quantity of the classified food (e.g., grams, ounces, milliliters, servings, or the like).

The bolus estimation logic 673 may be operable to evaluate a bolus dosage previously suggested by an AP application or AID algorithm based upon the prediction 672. For example, an AP application or AID algorithm may be operable to suggest and administer a pre-meal bolus based on past learned history of the user's meal patterns. The bolus estimate logic 673 may be operable to account for the amount of insulin in the administered pre-meal bolus and determine whether adjustments to future insulin deliveries are necessary if a food composition of the meal is determined to be different than an expected food composition of the meal indicated by the past learned history. For example, instead of a typical meal of starch, meat and vegetable, the user has a fast food meal of meat, a first starch (e.g., bread), a second starch (e.g., French fried potato) and a dairy food (e.g., chocolate milkshake). The output from the bolus estimation logic 673 may be a recommended bolus dosage 674 that accounts for the differences between the amount of insulin in the administered pre-meal bolus and an amount that compensates for the fast food meal.

Alternatively, or in addition, a pre-meal bolus may not be delivered by the AP application or AID algorithm, the bolus estimation logic 673 may be operable to evaluate the prediction 672 and output a recommended bolus dosage 674 that compensates (i.e., functions to maintain the user's blood glucose measurements with expected ranges above the hypoglycemic threshold and below the hyperglycemic threshold) for a meal composition determined by the CNN model 671. The AP application may utilize the prediction 672 as an input into a pump control component 688, that processes the prediction to generate a command signal 679 that is output to a medical device, such as 302 of FIG. 5.

An AP application or AID algorithm 681 may cause the delivery of a bolus containing insulin according to the recommended bolus dosage 674 by generating commands to instruct a medical device, such as medical device 302 of FIG. 5, or a pod. Alternatively, the AP application or AID algorithm 681 may use the recommended bolus dosage 674 as well as other data, such as most recent blood glucose measurements, to update a preset bolus dosage that is scheduled to be delivered contemporaneously with ingestion of a meal or in close temporal proximity to ingestion of the meal. For example, the preset bolus dosage may be 10 Units of insulin, but the AP application or AID algorithm 681 may update the preset bolus dosage by either reducing (e.g., to 8 Units of insulin) or increasing (e.g., to 18 Units of insulin) the preset bolus dosage based on the recommended bolus dosage 674 output from the image-based bolus estimation application or plug-in 680.

The image-based bolus estimation application or plug-in 680 may be further operable to provide the AP application or AID algorithm 681 with information usable for dynamic reconfiguration of algorithm settings and constants. For example, the algorithm settings related to particular meals may be reconfigured. In an example, the AP application or AID algorithm 681 may include safety constraint settings intended to prevent a user from administering dosages of insulin that may cause the user's blood glucose to fall outside a normal blood glucose measurement ranges and into a hypoglycemic or hyperglycemic range. The safety constraint settings may be related to the detected meal types identified and be set using various insulin decay curves (e.g., a time period during which the insulin is considered effective) that may be modified based on the detected meal content in the prediction 672. Further, the aggressiveness of the AP application or the AID algorithm 681 (e.g., how quickly a system tries to reduce the user's blood glucose to be within a blood glucose measurement range considered normal for the user) may also be modified according to the recommended bolus dosage 674, and/or, the prediction 672. For instance, images with significant proportions of pasta, bread, or other fast acting carbohydrates may benefit from an AP application or AID algorithm that is temporarily tuned to respond more aggressively to temporary but increased rates of change of a user's blood glucose measurements.

Figure 6D:
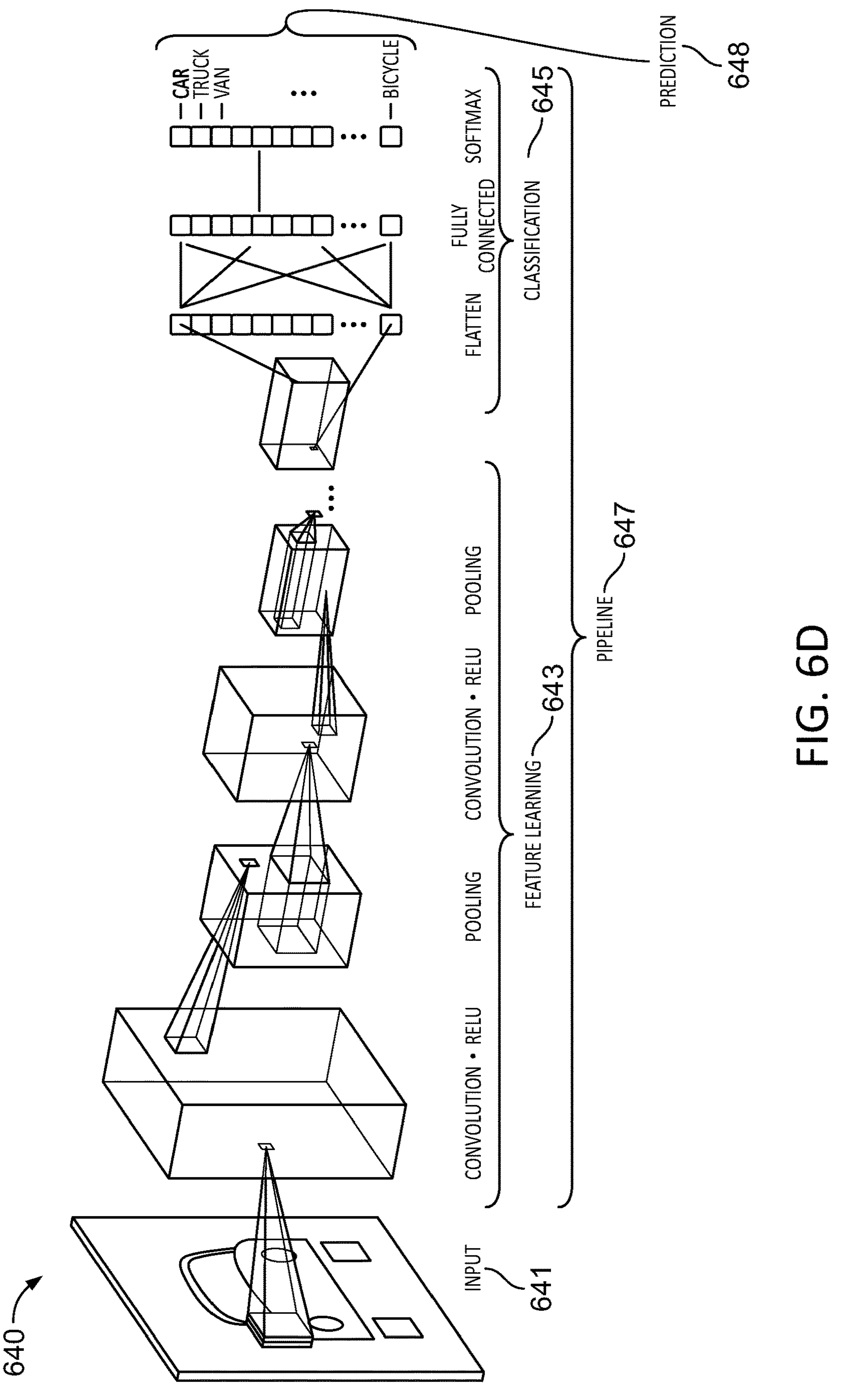
FIG. 6D illustrates a functional block diagram example of an image pipeline usable by in the convolutional neural network example of the image-based bolus estimation application described with reference to FIG. 6C.

In another example, the image recognition and classification resources, such as CNN model 671, may include programming that utilizes convolutional neural networks. The convolutional neural networks may be applied to classify a combination of food types and derive meal-related information such as the total carbohydrate content of the meal or other nutritional composition of the meal, meal size, date and time of the meal, or the like. Then convolutional neural network of CNN model 671 may be trained to utilize a database of images. Examples of such an image recognition service may be known in the art. FIG. 6D illustrates an example of a convolutional neural network that may be implemented by the example image-based bolus estimation application 680 of FIG. 6C.

In FIG. 6D, convolution neural networks (e.g., Convnets or CNNs), such as 640, may be built to be operable to provide image recognition, image classification, object detection, scene detection, and the like. A CNN, such as 640 may be pre-trained so values of the neural network are weighted to be optimally suited to detect types or categories of food, such as a steak, mashed potatoes, salad or the like. Or, as in the example of FIG. 6C, a vehicle. For example, weightings may be applied in the neural network that favor images of food, plates and utensils as compared to images of sunsets, boats, skateboards, people or other non-food related items. In the example of FIG. 6D, the example input image is an automobile, so the weightings of the neural network may be skewed in favor of elements of automobiles, such as edges, cylindrical shapes (i.e., wheels/tires) at the base of the image, and the like.

As shown in FIG. 6D, an input image of meal 651 may be input to the image-based bolus estimation application or plug-in 680. The input image may have a certain number of picture elements (i.e., pixels) arranged in a two dimensional pixel array, such as X pixels by Y pixels, where X and Y may be the same value or different values. The input image of a meal may include a number of pixels that each have individual pixels values. For example, each of the individual pixel in the X by Y pixel array may also have a specific value, such as 0-255 or 0-65535, or the like. The pixel values of the image may be input into the meal model. The image may, for example, be scanned "pixel by pixel" and a smaller filter may be applied to a sub-image of the same size, to extract features of the sub-image. As shown in FIG. 6D, various layers within the image pipeline 647 of the convolutional neural network 640 may extract other information from the inputted image data, and the "pre-trained" network generates an output with a probability of a recognized object. In such an example, the received image may be passed through the pipeline 647 (including the components: feature learning 643 and classification 645). The feature learning 643 and classification 645 components of the pipeline 647 may provide various operations such as filtering of the image for feature extraction from edges, curves, or the like, as well as the feature learning and classification. One or more feature learning operations may be applied during the feature learning 643. In the example, the feature learning 643 layer may include a repetitive implementation of convolution and activation functions, such as a rectified linear unit, a bipolar rectified linear unit, a parametric rectified linear unit, a Gaussian error linear unit, or the like. As shown in feature learning 643 layer, a first convolution with activation (i.e., RELU) operation may be applied to pixel values within a segment of the image, and the results of the first convolution and activation operation may be "pooled" in a sub-image (an image having smaller dimensions than a prior input image or sub-image) by a first pooling operation. The first convolution and activation operation and first pooling operation may be followed by a second convolution with activation (i.e., RELU) operation and a second pooling operation before application of a classification 645 layer. In the example of FIG. 6D, the feature learning 643 layer is shown with only two implementations of convolution and activation operations and pooling operations, however, more or less convolution and activation operations and pooling operations may be implemented depending upon the degree of granularity and/or the amount of available computing resources. For example, if the CNN processing is performed by a cloud-based service, a greater number of convolution and activation operations and pooling operations may be implemented than when a mobile device, such as a PDM 306, performs the image recognition because the cloud-based system may have access to computing resources with greater processing power. As shown in FIG. 6D, the pipeline 647 may provide an output 648 that includes a probability of a recognized object. For example, the output 648 may be a list of possible classifications of the input image 641 with respective probabilities of each being the actual object in the image 651. In a further example, the output 648 may be presented on a display device which enables a user to select via a user interface multiple objects detected from the input image 641 as parts of the meal (e.g., meat, potatoes and a drink). The recognized objects with the highest probabilities may be considered predicted objects and may be the prediction output 648.

Figure 6E:
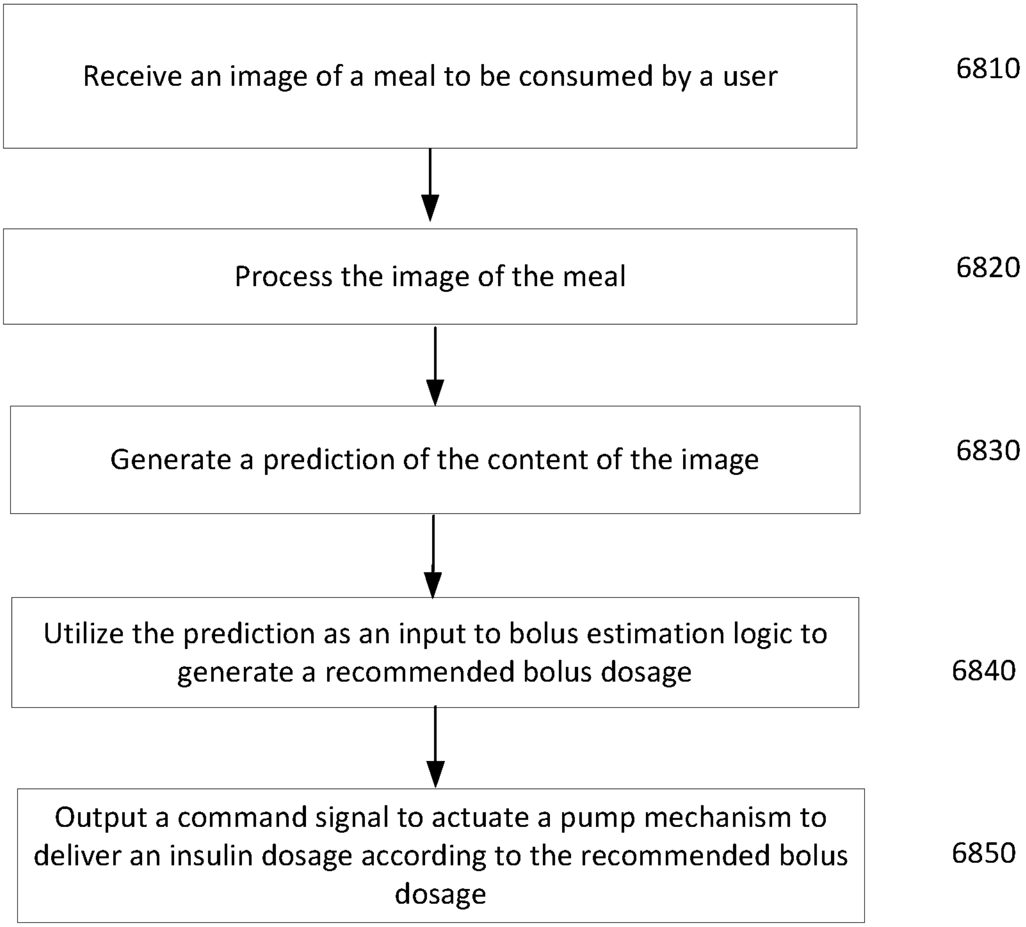
FIG. 6E is a flow chart of a meal evaluation and compensation process that is operable to extract meal-related information from inputs into an image-based bolus estimation application or plug-in that is operable to return a recommended bolus dosage.

FIG. 6E illustrates flow chart of an example process executed by the example components shown in the examples of FIGS. 6C and 6D. In the operational example of FIG. 6E explained with reference to the elements of FIGS. 6C and 6D, the process 6800 may begin with an image being obtained by a visual front end (i.e., image sensor) of a camera 654, which outputs the image as a bit stream 657 of image data that is received by the image-based bolus estimation application or plug-in 680 (6810).

At 6820, the image-based bolus estimation application or plug-in 680 may process the image of the meal. For example, the received image may be processed to place the resolution of the image at a resolution for further processing.

The CNN model 671 may include one or more components of the image pipeline 647 of FIG. 6D. As a final operation of the pipeline 647, a classification operation(s) may be applied to the output of the feature learning operations. For example, a final activation function may be applied, such as a softmax activation function, which provides probabilities of various outcomes. The CNN model 671 of the image-based bolus estimation application or plug-in 680 may generate a prediction 672 (6830).

The generated prediction may be provided to bolus estimation logic as an input for the generation of a recommended bolus dosage (6840). As shown in FIG. 6C, the prediction 672 is provided to the bolus estimation logic 673. The bolus estimation logic 673 may be operable to perform various functions, such as, evaluate the prediction 672 with respect to other inputs, such as previous insulin deliveries (including basal and/or bolus deliveries), a determined amount of insulin onboard (IOB), a latest or most recent blood glucose measurement value, a rate of change of blood glucose measurements over a predetermined period of time, blood glucose measurement history, or the like. Based on the prediction 672 and, if used, the other inputs, the bolus estimation logic 673 may calculate a recommended bolus dosage 674. The recommended bolus dosage 674 may be output by the image-based bolus estimation application or plug-in 680 to the AP Application or AID algorithm 681. At the AP Application or AID algorithm 681, a command signal may be output to actuate a pump mechanism of a medical device to deliver an insulin dosage according to the recommended bolus dosage (6850).

Figure 7:
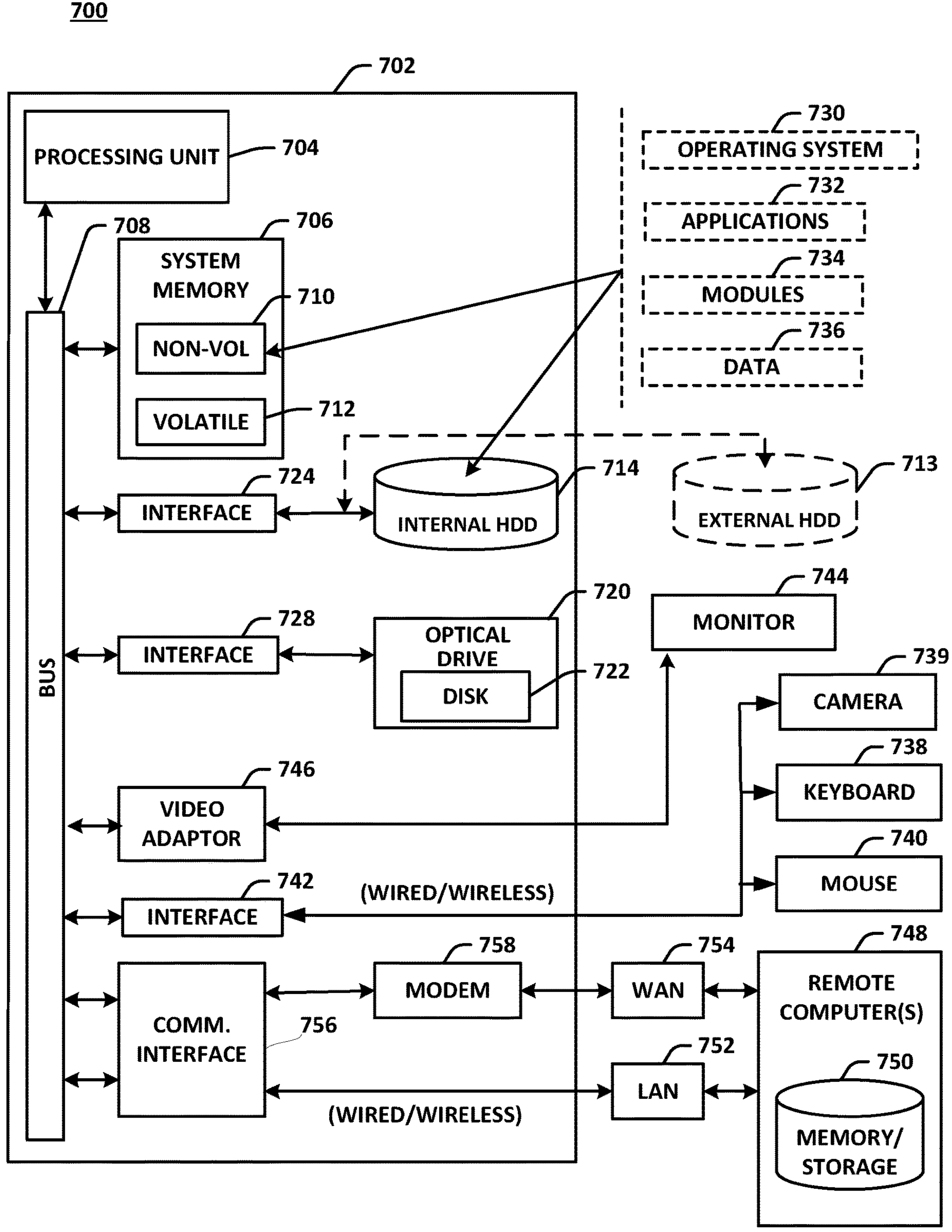
FIG. 7 illustrates a computer architecture suitable for operating as hardware and software components of implementing systems and processes such as those shown in the examples of FIGS. 1-6C.

The management device 306, medical device 302, smart accessory device 307 and sensor 304 of FIG. 5 may have hardware and software configurations that enable implementation of the processes described in the examples of FIGS. 1-6C. FIG. 7 illustrates an example of a computing architecture suitable for implementing various examples as previously described. In one example, the computing architecture 700 may include or be implemented as part of system 300 of FIG. 5.

As used in this application, the terms "system" and "component" are intended to refer to a computer-related entity, either hardware, a combination of hardware and software, software, or software in execution, examples of which are provided by the exemplary computing architecture 700 as well as the examples of FIGS. 5, 6A, 6C and 6D. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server or a processor and the server or the processor can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media (e.g., wired links and/or wireless links). The information can be implemented as signals allocated to various signal lines. In such allocations, each message is a signal. Further examples, however, may alternatively employ data messages. Such data messages may be sent across various connections. Exemplary connections include parallel interfaces, serial interfaces, and bus interfaces.

The computing architecture 700 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The examples, however, are not limited to implementation by the computing architecture 700.

As shown in FIG. 7, the computer architecture 700 includes a processing unit 704, a system memory 706 and a system bus 708. The processing unit 704 can be any of various commercially available processors. For example, the management device 306, smart accessory device 307 or the medical device 302 and components of any of the devices 302, 306 and 307, may incorporate one or more of the components of the computer architecture 700, such as the processing unit 704, the system memory 706 and so on. Other components, such as the keyboard 738 and the mouse 740, may be omitted in some examples.

The system bus 708 provides an interface for system components including, but not limited to, the system memory 706 to the processing unit 704. The system bus 708 can be any of several types of bus structures that may further interconnect to a memory bus (with or without a memory controller), a peripheral bus, and/or a local bus using any of a variety of commercially available bus architectures. Interface adapters may connect to the system bus 708 via slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The computing architecture 700 may include or implement various articles of manufacture. An article of manufacture may include a computer-readable storage medium to store logic. Examples of a computer-readable storage medium may include any tangible media capable of storing electronic data, including volatile memory or non-volatile memory, removable or non-removable memory, erasable or non-erasable memory, writeable or re-writeable memory, and so forth. Examples of logic may include executable computer program instructions implemented using any suitable type of code, such as source code, compiled code, interpreted code, executable code, static code, dynamic code, object-oriented code, visual code, and the like. Examples may also be at least partly implemented as instructions contained in or on a non-transitory computer-readable medium, which may be read and executed by one or more processors to enable performance of the operations described herein.

The system memory 706 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the example shown in FIG. 7, the system memory 706 can include non-volatile memory 710 and/or volatile memory 712. A basic input/output system (BIOS) can be stored in the non-volatile memory 710.

The computer 702 may include various types of computer-readable storage media in the form of one or more lower speed memory units, including an internal (or external) hard disk drive (HDD) 714 or 713, and an optical disk drive 720 to read from or write to a removable optical disk 722 (e.g., a CD-ROM or DVD). The HDD 714 and optical disk drive 720 can be connected to the system bus 708 by an HDD interface 724 and an optical drive interface 728, respectively. The HDD interface 724 for external drive implementations can include at least one or both of Universal Serial Bus (USB) and IEEE 1394 interface technologies. The drives and associated computer-readable media provide volatile and/or nonvolatile storage of data, data structures, computer-executable instructions, and so forth. For example, several program modules can be stored in the drives and memory units 710 and 712, including an operating system 730, one or more application programs 732 (such as an AP application, an image-based bolus estimation application and the like), other program modules 734, and program data 736. In one example, the one or more application programs 732, other program modules 734, and program data 736 can include, for example, the various applications (e.g., Bluetooth® transceiver, camera applications and the like) and/or components of the computer architecture 700.

A user can enter commands and information into the computer 702 through one or more wired/wireless input devices, for example, a camera 739, a keyboard 738 and a pointing device, such as a mouse 740. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, track pads, sensors, styluses, and the like. The camera 739, the keyboard 738 and mouse 740 as well as the other input devices are often connected to the processing unit 704 through an input device interface 742 that is coupled to the system bus 708 but can be connected by other interfaces such as a parallel port, IEEE 1394 serial port, a game port, a USB port, an IR interface, and so forth.

A monitor 744 or other type of display device is also connected to the system bus 708 via an interface, such as a video adaptor 746. The monitor 744 may be internal or external to the computer 702. In addition to the monitor 744, a computer typically includes other peripheral output devices, such as speakers, printers, and so forth, that are not shown for ease of illustration.

The computer 702 may operate in a networked environment using logical connections via wired and/or wireless communications to one or more remote computers, such as a remote computer 748. The remote computer 748 can be a workstation, a server computer, a router, a personal computer, portable computer, microprocessor-based entertainment appliance, a peer device or other common network node, and typically includes many or all the elements described relative to the computer 702, although, for purposes of brevity, only a memory/storage device 750 is illustrated. The logical connections depicted include wired/wireless connectivity to a local area network (LAN) 752 and/or larger networks, for example, a wide area network (WAN) 754. Such LAN and WAN networking environments are commonplace in offices and companies, and facilitate enterprise-wide computer networks, such as intranets, all of which may connect to a global communications network, for example, the Internet and cloud-based services, such as 311 of FIG. 3.

When used in a LAN networking environment, the computer 702 may be connected to the LAN 752 through a wired and/or wireless communication interface 756. The communication interface 756 can facilitate wired and/or wireless communications to the LAN 752, which may also include a wireless access point disposed thereon for communicating with the wireless functionality of the communication interface 756.

When used in a WAN networking environment, the computer 702 can include a modem 758, or is connected to a communications server on the WAN 754 or has other means for establishing communications over the WAN 754, such as by way of the Internet. The modem 758, which can be internal or external and a wire and/or wireless device, connects to the system bus 708 via the input device interface 742. In a networked environment, program modules depicted relative to the computer 702, or portions thereof, can be stored in the remote memory/storage device 750. It will be appreciated that the network connections shown in FIG. 7 (as well as those of FIG. 5) are exemplary and other means of establishing a communications link between the computers can be used.

The computer 702 is operable to communicate with wired and wireless devices or entities using the IEEE 802 family of standards, such as wireless devices operatively disposed in wireless communication (e.g., IEEE 802.11 over-the-air modulation techniques). This includes at least Wi-Fi (or Wireless Fidelity), WiMax, and Bluetooth® wireless technologies, among others. Thus, the communication can be a predefined structure as with a conventional network or simply an ad hoc communication between at least two devices. Wi-Fi networks use radio technologies called IEEE 802.118 (a, b, g, n, etc.) to provide secure, reliable, fast wireless connectivity. A Wi-Fi network can be used to connect computers to each other, to the Internet, and to wire networks (which may use IEEE 802.3-related media and functions).

The various elements of the devices as previously described with reference to FIGS. 1-6E may include various hardware elements, software elements, or a combination of both. Examples of hardware elements may include devices, logic devices, components, processors, microprocessors, circuits, processors, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), memory units, logic gates, registers, semiconductor device, chips, microchips, chip sets, and so forth. Examples of software elements may include software components, programs, applications, computer programs, application programs, system programs, software development programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof.

A mobile device may be operable to provide the image-based bolus estimation application and/or the AP application or the AID algorithm and techniques described herein may include a variety of different types of user interface elements. For example, FIG. 8 illustrates a block diagram illustration of an example of a mobile device usable for implementing the techniques and processes discussed with reference to the examples of FIGS. 1-6C.

The mobile device 811 may be a smart phone including a display device, such as a touch screen display 820. The touch screen display 820 may be coupled to the processor 812 and be operable to present screen content and receive inputs via touch sensors 822. Examples of touch screen type mobile devices, such as mobile device 811, may include (but are not limited to) a smart phone, personal digital assistant (PDA), tablet computer, smart watch, or another portable device. However, the structure and operation of mobile device 811 that utilizes a touch screen is provided by way of example; and the subject technology as described herein is not intended to be limited thereto. For purposes of this discussion, the example touch screen display 820 of the mobile device 811 may be operable to display content and receive user inputs as (or as part of) the user interface.

There are a variety of ways that a mobile device 811 may be operable to obtain information as to current location of the device. In our example, the mobile device 811 includes a global positioning satellite (GPS) receiver 832 and associated antenna 834. A rechargeable battery 829 may provide electrical power sufficient to power the various components of the mobile device 811. The mobile device 811 is also equipped with a camera 839 that is coupled to the processor 812 and controllable to collect images via an input to the touchscreen display 820. For example, the image-based bolus estimation application 847 may be operable to control the mobile device 811 to enable collection images of receipts from purchase transactions via the camera 839 and send the collected images to a best deal service (shown in other examples).

Figure 8:
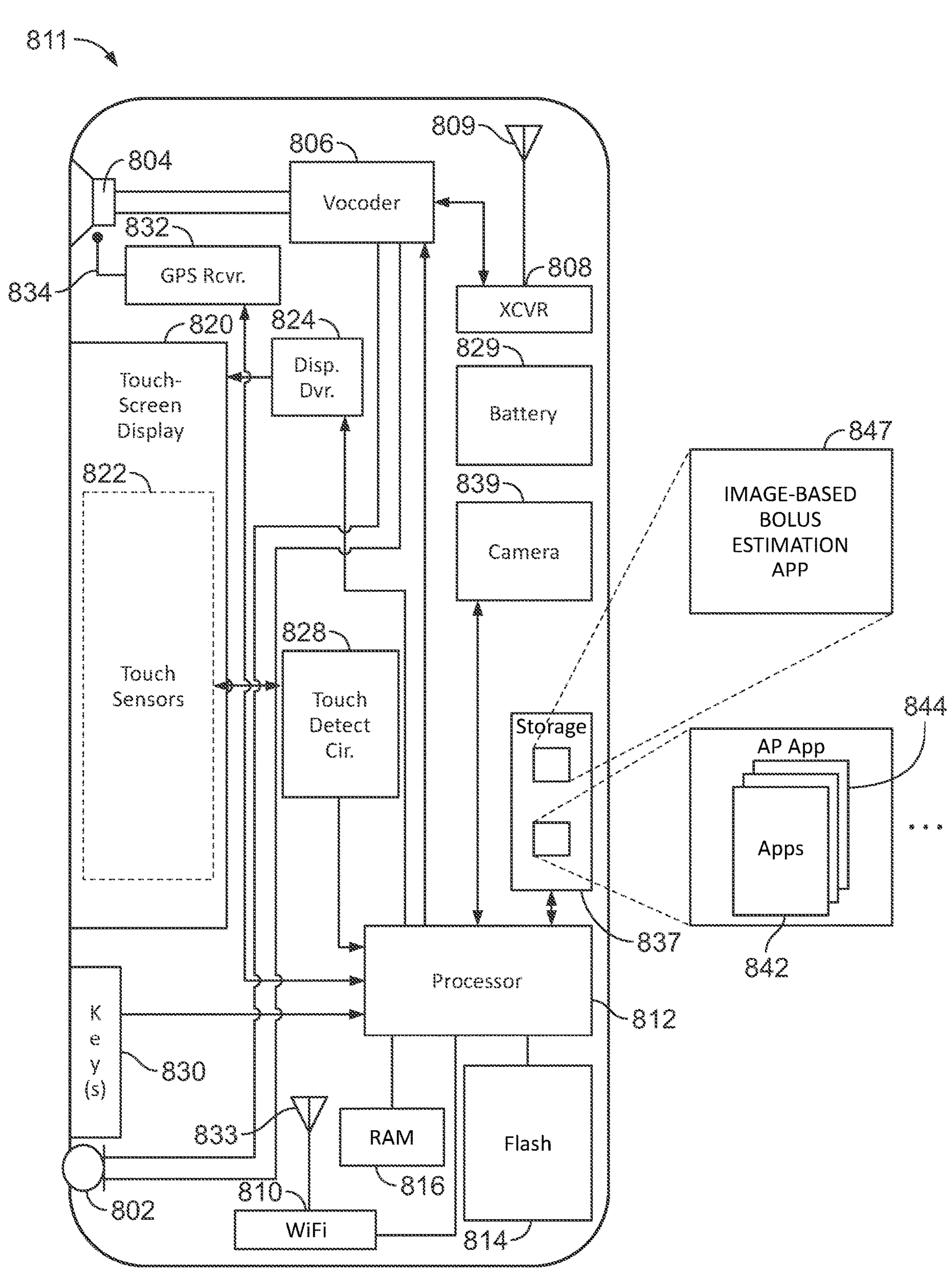
FIG. 8 illustrates an example of a mobile device usable for implementing the techniques and processes discussed with reference to the examples of FIGS. 1-6C.

For discussion purposes, in the smart phone example of a mobile device shown in FIG. 8, the user interface elements of mobile device 811 include a touch screen display 820 (also referred to herein as "touch screen 820" or "display 820"). For output purposes, the touch screen 820 includes a display screen, such as a liquid crystal display (LCD) or the like. For input purposes, touch screen display 820 includes a plurality of touch sensors 822. Other interface elements may include a keypad including one or more keys 830. For example, the keypad may be implemented in hardware as a T9 or QWERTY keyboard of mobile device 811 and keys 830 may correspond to the physical keys of such a keyboard. Alternatively, keys 830 (and keyboard) of mobile device 811 may be implemented as "soft keys" of a virtual keyboard graphically represented in an appropriate arrangement via touch screen display 820. The soft keys presented on the touch screen display 820 may allow the user of mobile device 811 to invoke the same user interface functions as with the physical hardware keys. In some implementations, the microphone 802 and speaker 804 may be used as additional user interface elements, for audio input and output, including with respect to some functions related to the processing related to engaging with the image-based bolus estimation application 847, as described herein.

For output, touch screen display 820 is a display device used to present information (e.g., text, video, graphics or other visible content) to the user of mobile device 811. Processor 812 controls visible display output on the LCD or other display element of the touch screen display 820 via a display driver 824, to present the various visible outputs to the device user. In general, touch screen display 820 and touch sensors 822 (and one or more keys 830, if included) are used to provide the textual and graphical user interface for the mobile device 811. Touch screen display 820 also enables the user to interact directly with the viewable, presented information provided in the display 820, typically by touching the surface of the screen display with a finger or an implement such as a stylus.

As shown in FIG. 8, the mobile device 811 also includes a touch detect circuit 828 coupled to touch sensors 822 for detecting the occurrence and relative location/position of each touch with respect to a content display area of touch screen display 820. In this example, touch detect circuit 828 is operable to provide processor 812 with touch-position information based on user input received via touch sensors 822. In some implementations, processor 812 is operable to correlate the touch position information to specific content being displayed within the content display area on touch screen display 820. The touch-position information captured by touch detect circuit 828 and provided to processor 812 may include, but is not limited to, coordinates identifying the location of each detected touch with respect to the display area of touch screen display 820 and a timestamp corresponding to each detected touch position.

In the example shown in FIG. 8, the mobile device 811 includes a microphone 802 for audio signal input and a speaker 804 for audio signal output. The microphone 802 and speaker 804 are communicatively coupled to a voice or audio encoder/decoder (vocoder) 806. For a voice telephone call, for example, the vocoder 806 provides two-way conversion between analog audio signals representing speech or other audio and digital samples at a compressed bit rate compatible with the digital protocol of wireless telephone network communications or voice over packet (e.g., Internet Protocol) communications. The vocoder, speaker and microphone may also be used as elements of the user interface during other operations of the device, including some types of transaction communications.

Also, as shown in FIG. 8, the mobile device 811 includes at least one transceiver (XCVR) 808, which may be a digital transceiver for digital wireless communications via a wide area wireless mobile communication network, although the mobile device 811 may include additional digital or analog transceivers (not shown). The transceiver 808 conforms to one or more of the various digital wireless communication standards utilized by modern mobile networks. Examples of such transceivers include (but are not limited to) transceivers operable to operate in accordance with Code Division Multiple Access (CDMA) and 3rd Generation Partnership Project (3GPP) network technologies including, for example and without limitation, 3GPP type 2 (or 3GPP2) and 3GPP Long Term Evolution (LTE), at times referred to as "4G." For example, a transceiver 808 provides two-way wireless communication of information including digitized audio signals, still image and/or video signals, web page information for display as well as web related inputs, and various types of mobile message communications to/from the mobile device 811. Transceiver 808 connects through radio frequency (RF) send-and-receive amplifiers (not separately shown) to an antenna 809. The transceiver 808 may also support various types of mobile messaging services, such as short message service (SMS), enhanced messaging service (EMS), and/or multimedia messaging service (MMS).

In an example, the transceiver 808 may be coupled to the processor 812 and be operable to exchange communications. The processor 812 of the mobile device 811 may be further operable to perform additional functions, including functions to establish, using the transceiver, a connection with a medical device, such as medical device 302 of FIG. 5, to exchange communications. Via the connection with the cloud-based services 311 of FIG. 5 via the image-based bolus estimation application 847, the mobile device 811 may be operable to enable collection images via the camera 839 and send the collected images to the image-based bolus estimation application 847, and the like. The processor upon execution of the image-based bolus estimation application 847 may implement the examples as discussed above with reference to FIGS. 1-6C.

The mobile device 811 may also include a Wi-Fi transceiver 810 and associated antenna 833. Although Wi-Fi is used here as the example, the transceiver 810 may take the form of any available two-way wireless local area network transceiver of a type that is compatible with one or more standard protocols of communication implemented in wireless local area networks, such as one of the Wi-Fi standards under IEEE 802.11 and/or WiMAX.

The mobile device 811 further includes a processor 812, which serves as a programmable controller for mobile device 811 by configuring mobile device 811 to perform various operations, for example, in accordance with instructions or programming executable by processor 812. A flash memory 814 may be used to store, for example, programming or instructions for execution by the processor 812. Depending on the type of device, the mobile device 811 stores and runs an operating system through which specific applications may be run on the device. Examples of operating systems include Android, Apple iOS, Microsoft Windows OS, Bada, Tizen, Symbian OS, Blackberry OS, or the like. Flash memory 814 may also be used to store mobile configuration settings for different mobile applications or services executable at mobile device 811 (using processor 812). Mobile device 811 may also include a non-volatile random-access memory (RAM) 816 for a working data processing memory. The RAM memory 816 or storage 837 may be coupled to the processor 812 and operable to store programming code executable by the 812 processor.

Alternatively, or in addition, applications may be stored in storage 837, which may be a solid-state memory storage or other memory device suitable for storing applications. In one example, the storage 837 may be a separate chip that includes tamperproof storage and execution memory and is operable to communicate with operating system. The storage 837 may, for example, store applications 842, which may be a map application, a messaging application as well as an instance of an image-based bolus estimation application 847 for processing image data, or store an instance of AP application 844 for processing a diabetes treatment program that includes generating commands for the delivery of insulin and communicating with one or more devices or processors of paired devices (such as medical device 302, smart accessory device 307 or sensor 304 of FIG. 5), and processes as described with reference to the examples of FIGS. 1-6C.

The logic implemented by the processor 812 of the mobile device 811 configures the processor 812 to control various functions as implemented by the mobile device 811. The logic for a processor may be implemented in a variety of ways, but in the presented examples, the processor logic is implemented by programming for execution by the processor 812.

The techniques described herein for providing functionality to determine content of food and provide a recommended bolus dosage. For example, the system 300 of FIG. 5 or any component thereof may be implemented in hardware, software, or any combination thereof. Software related implementations of the techniques described herein may include, but are not limited to, firmware, application specific software, or any other type of computer readable instructions that may be executed by one or more processors. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

In addition, or alternatively, while the examples may have been described with reference to a closed loop algorithmic implementation, variations of the disclosed examples may be implemented to enable open loop use. The open loop implementations allow for use of different modalities of delivery of insulin such as smart pen, syringe or the like. For example, the disclosed AP application and algorithms may be operable to perform various functions related to open loop operations, such as the generation of prompts presenting the recommended bolus dosage to a user via a user interface. Other open-loop actions may also be implemented by adjusting user settings or the like in an AP application or algorithm.

Some examples of the disclosed device may be implemented, for example, using a storage medium, a computer-readable medium, or an article of manufacture which may store an instruction or a set of instructions that, if executed by a machine (i.e., processor or microcontroller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosure were described above. It is, however, expressly noted that the present disclosure is not limited to those examples, but rather the intention is that additions and modifications to what was expressly described herein are also included within the scope of the disclosed examples. Moreover, it is to be understood that the features of the various examples described herein were not mutually exclusive and may exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

Program aspects of the technology may be thought of as "products" or "articles of manufacture" typically in the form of executable code and/or associated data that is carried on or embodied in a type of machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of examples has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

What is claimed is:

1. A system, comprising:

a processor;

a memory storing programming code, an artificial pancreas application, and operable to store data related to the artificial pancreas application, wherein the programming code and the artificial pancreas application are executable by the processor; and a transceiver operable to receive and transmit signals containing information usable by or generated by the artificial pancreas application when executed by the processor, wherein the processor when executing the artificial pancreas application is configured to:

receive blood glucose measurements over a period of time;

generate predicted glucose values using a glucose prediction model;

compare the predicted glucose values from the glucose prediction model to measured blood glucose values of the received blood glucose measurements;

identify deviations between the predicted blood glucose values and additional blood glucose measurements;

evaluate the identified deviations with respect to a blood glucose deviation threshold;

determine a quantity of the identified deviations that exceed the blood glucose deviation threshold;

based on the result of the determination, recalculate error parameters of the glucose prediction model;

update glucose and insulin dynamics coefficients of the glucose prediction model using the recalculated error parameters to provide new glucose and insulin dynamics coefficients;

receive subsequent blood glucose measurements over a subsequent period of time;

using the new glucose and insulin dynamics coefficients and the received subsequent blood glucose measurements in an updated glucose prediction model, obtain predictions of future glucose measurements;

calculate a future insulin dosage based on the obtained predictions of future glucose measurements; and cause delivery of the calculated future insulin dosage to a user.

2. The system of claim 1, further comprises:

a blood glucose sensor communicatively coupled to the processor wherein the blood glucose sensor is operable to:

measure a blood glucose value at a predetermined time interval; and provide the measured blood glucose value to the processor and the artificial pancreas application.

3. The system of claim 1, further comprises:

a drug delivery device communicatively coupled to the processor, wherein the drug delivery device includes a pump mechanism and a medical device processor, wherein the medical device processor is operable to:

receive an instruction to deliver the calculated future insulin dosage; and actuate the pump mechanism in response to the received instruction.

4. The system of claim 1, wherein the processor when executing the programming code is further configured, prior to comparing the predicted glucose values from the glucose prediction model to the measured blood glucose values, to:

obtain an amount of insulin delivered in each respective insulin delivery for past insulin deliveries over the period of time; and use the obtained amount of insulin delivered in each respective insulin delivery for past insulin deliveries over the period of time as inputs to the glucose prediction model.

5. The system of claim 1, wherein the processor when executing the programming code is further configured, when generated predicted glucose values using the glucose prediction model, to:

obtain a raw rate of change of raw blood glucose measurement values over the period of time;

obtain past insulin on board determinations over the period of time; and input the raw rate of change of raw blood glucose measurement values and the past insulin on board determinations into the glucose prediction model.

6. The system of claim 1, wherein the processor when executing the programming code is further configured, when recalculating the error parameters of the glucose prediction model, to:

obtain current glucose measurement values from the blood glucose measurements received over the period of time;

evaluate past predicted glucose measurements and current glucose measurement values to obtain an estimated error between the past predicted glucose measurements and the current glucose measurement values; and use the estimated error in the recalculating the error parameters of the glucose prediction model.

7. The system of claim 1, wherein the processor when executing the programming code is further configured, when updating the glucose and the insulin dynamics coefficients, to:

use a history horizon parameter for which the error may be assessed, an actual prediction horizon parameter for which the updated glucose prediction model may predict into the future, and a bias value, which is a tuning parameter that can be scaled against the history horizon parameter and the actual prediction horizon parameter to modify how rapidly dynamics coefficients of the updated glucose prediction model are adjusted.

* * * * *